(12) United States Patent
Raines et al.

(10) Patent No.: US 9,809,586 B2
(45) Date of Patent: Nov. 7, 2017

(54) INHIBITORS OF COLLAGEN PROLYL 4-HYDROXYLASE

(71) Applicant: WISCONSIN ALUMNI RESEARCH FOUNDATION, Madison, WI (US)

(72) Inventors: Ronald T. Raines, Madison, WI (US); James Vasta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/082,372

(22) Filed: Mar. 28, 2016

(65) Prior Publication Data

US 2016/0280701 A1 Sep. 29, 2016

Related U.S. Application Data

(60) Provisional application No. 62/139,685, filed on Mar. 28, 2015.

(51) Int. Cl.
| | |
|---|---|
| *A61K 31/4025* | (2006.01) |
| *A61K 31/4155* | (2006.01) |
| *A61K 31/4178* | (2006.01) |
| *A61K 31/421* | (2006.01) |
| *A61K 31/426* | (2006.01) |
| *A61K 31/444* | (2006.01) |
| *A61K 31/497* | (2006.01) |
| *A61K 31/501* | (2006.01) |
| *C07D 401/04* | (2006.01) |
| *C07D 413/04* | (2006.01) |
| *C07D 417/04* | (2006.01) |
| *C07D 213/80* | (2006.01) |

(52) U.S. Cl.
CPC ......... *C07D 417/04* (2013.01); *C07D 213/80* (2013.01); *C07D 401/04* (2013.01); *C07D 413/04* (2013.01)

(58) Field of Classification Search
CPC ............ A61K 31/4025; A61K 31/4155; A61K 31/4178; A61K 31/421; A61K 31/426; A61K 31/444; A61K 31/497; A61K 31/501; C07D 401/04; C07D 413/04; C07D 417/04
USPC ..... 514/252.03, 255.06, 340, 341, 342, 343; 544/238, 405; 546/270.4, 271.4, 274.1, 546/275.4, 279.1
See application file for complete search history.

(56) References Cited

U.S. PATENT DOCUMENTS

| 4,904,675 A | 2/1990 | Winter-Mihaly et al. |
| 5,614,520 A | 3/1997 | Kondo et al. |
| 2013/0065918 A1 | 3/2013 | Brenneman et al. |

OTHER PUBLICATIONS

Berg, R. A.; Prockop, D. J. Biochem. Biophys. Res. Comm. 1973, 52, 115.
Cunliffe, C. J. et al. J. Med. Chem. 1992, 35, 2652-2658.
Dowell, R. I.; Hadley, E. M. J. Med. Chem. 1992, 35, 800.
Dowell, R.I; Hadley E.M. Eur. J. Med. Chem. 1993, 28, 513-516.
Duric, S.; Tzschucke, C. C. Org. Lett. 2011, 13, 2310.
Ford, P. C., DeForest, P. R., Gaunder, R., and Taube, H. (1968)Synthesis and properties of pentaamminepyridineruthenium(II) and related pentaammineruthenium complexes of aromatic nitrogen heterocycles, 1968, J. Am. Chem. Soc. 90, 1187-1194.
Franklin, T. J.; Morris, W. P.; Edwards, P. N.; Large, M. S.; Stephenson, R. Biochem. J. 2001, 353, 333.
Gilkes et al. 'Collagen Prolyl Hydroxylases are Essential for Breast Cancer Metastasis', Molecular and Cellular Pathobiology, Cancer research, Mar. 2013, vol. 73(11), pp. 3285-3296.
Gorres, K. L.; Raines, R. T. Crit. Rev. Biochem. Mol. 2010, 45, 106.
Hales et al. 'Novel inhibitors of prolyl 4-hydroxylase. 5. The intriguing structure-activity relationships seen with 2,2'-bipyridine and its 5,5'-dicarboxylic acid derivatives', J. Med. Chem., 1993, vol. 36 (24), pp. 3853-3858.
International Search Report from PCT/US2016/24522 which corresponds to the above-referenced application, dated Jun. 30, 2016.
Krumholz, P. "Ferrous mono-α,α'-dipyridyl," 1949, J. Am. Chem. Soc. 71, 3654-3656.
Myllyharju, J. Ann. Med. 2008, 40, 402.

(Continued)

*Primary Examiner* — Brenda Coleman
(74) *Attorney, Agent, or Firm* — Lathrop Gage LLP

(57) ABSTRACT

Biheteroaryl dicarboxylates and esters, and salts thereof which are useful as modulators of CP4H activity and more particularly as inhibitors of CP4H. Compounds of formula:

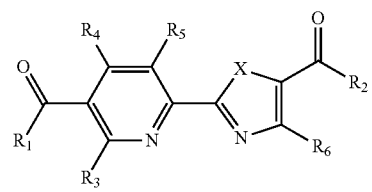

and salts thereof
where:
X is S, O, NH, or NR, where R is an alkyl group having 1-3 carbon atoms;
$R_1$ and $R_2$ independently are —$OR_7$, or —$NHSO_2R_8$, where $R_7$ is selected from:
hydrogen, alkyl, alkenyl, alkoxyalkyl, —R'—CO—R", —R'—CO—O—R", —CO—R", —R'—O—CO—R", —R'—CO—NR", —CO—NR", or —R'—O—CO—NR", and $R_8$ is selected from hydrogen, alkyl, aryl, arylalkyl;
$R_3$, $R_4$ and $R_6$ independently are hydrogen, alkyl, alkoxy, alkenyl, alkenoxy, haloalkyl, haloalkenyl, halogen, hydroxyl, hydroxyalkyl, hydroxyalkenyl, aryl, aryloxy, arylalkyl or arylalkyloxy; $R_5$ is hydrogen, halogen, alkyl having 1-3 carbon atoms, or alkoxy having 1-3 carbon atoms; —R'— is a divalent straight chain or branched alkylene, and —R" is an alkyl, alkenyl, arylalkyl, or aryl group. Methods for inhibition of CP4H in vivo and in vitro.

21 Claims, 14 Drawing Sheets

(56) References Cited

OTHER PUBLICATIONS

Myllylä, R.; Tuderman, L.; Kivirikko, K. I. Eur. J. Biochem. 1977, 80, 349.
Rose, N. R.; Mcdonough, M. A.; King, O. N. F.; Kawamura, A.; Schofield, C. J. Chem. Soc. Rev. 2011, 40, 4364.
Sasaki, T.; Majamaa, K.; Uitto, J. J. Biol. Chem. 1987, 262, 9397.
Tucker, H.; Thomas, D. F. J. Med. Chem. 1992, 35, 804.
Vasta, J. et al. "Selective Inhibition of Prolyl 4-Hydroxylases by Bipyridenedicarboxylates," Biorg.Med. Chem. May 23, 2015,(13), 3081-3090.
Vasta, J.D., Anderson, K.A., Deck, K.M., Nizzi, C. P. Eisenstein, R.S. and Raines, R.T. "Selective Inhibition of Collagen Prolyl 4-Hydroxylase in Human Cells," ACS Chemical Biol. Nov. 2016, 11, 193-199.
Wang, J.; Buss, J. L.; Chen, G.; Ponka, P.; Pantopoulos, K. FEBS Lett. 2002, 529, 309.

INHIBITORS OF COLLAGEN PROLYL 4-HYDROXYLASE

CROSS-REFERENCE TO RELATED APPLICATIONS

The present invention claims the benefit of U.S. provisional application 62/139,685, filed Mar. 28, 2015, which is incorporated by reference herein in its entirety.

STATEMENT REGARD GOVERNMENT SUPPORT

This invention was made with government support under AR044276 awarded by the National Institutes of Health. The government has certain rights in the invention.

BACKGROUND OF THE INVENTION

Collagen is the principle component of bone, connective tissues, and the extracellular matrix in animals.[1] The overproduction of collagen is associated with a variety of diseases, including fibrotic diseases[2] and cancers.[3-7] The stability of collagen relies on posttranslational modifications that occur throughout the secretory pathway.[8] The most prevalent of these modifications is the hydroxylation of collagen strands by collagen prolyl 4-hydroxylases (CP4Hs), which are Fe(II)- and α-ketoglutarate (AKG)-dependent dioxygenases (FAKGDs) located in the lumen of the endoplasmic reticulum.[9] Catalysis by CP4Hs convert (2S)-proline (Pro) residues in protocollagen strands into (2S,4R)-4-hydroxyproline (Hyp) residues (FIG. 1A), which are essential for the conformational stability of mature collagen triple helices.[10] Importantly, CP4Hs are validated targets for treating both fibrotic diseases[11] and metastatic cancer, particularly breast cancer.[6]

Like all enzymes of the FAKGD superfamily, catalysis by CP4Hs requires Fe(II), and the cosubstrates AKG and dioxygen.[12,39,40] The Fe(II) is bound by a conserved His-X-Asp/Glu . . . Xn . . . His motif, and AKG chelates to enzyme-bound Fe(II) using its C-1 carboxylate and C-2 keto groups, while the C-5 carboxylate group forms hydrogen bonds and engages in Coulombic interactions with a basic residue (typically arginine or lysine). All FAKGDs are believed to effect catalysis through a similar two-stage mechanism in which AKG is first oxidatively decarboxlated to generate a highly reactive Fe(IV)=O species (ferryl ion), which effects hydroxylation via a radical rebound process.[12,39,40]

In vertebrates, CP4Hs are known to exist as $\alpha_2\beta_2$ tetramers. In these tetramers, the α-subunit contains the catalytic and substrate-binding domains, and the β-subunit is protein disulfide isomerase, which is a multifunctional protein that is responsible for maintaining the α-subunit in a soluble and active conformation.[9] Three isoforms of the α-subunit, α(I), α(II), and α(III), have been identified in humans.[9] All α-subunit isoforms form tetramers with the β-subunit, which are referred to herein as the CP4H1, CP4H2, and CP4H3 holoenzymes. As the most prevalent of the isoforms, CP4H1 has been extensively characterized. Whereas the structure of the tetrameric complex is unknown, those of the individual domains of the α(I)-subunit have provided insight into the manner in which CP4Hs interact with the protocollagen substrate, as well as the means by which the α(I)-subunits dimerize to facilitate formation of the tetramer.[13-16]

The development of CP4H inhibitors has been of interest since the mid 1970s. Like many FAKGDs, human CP4Hs are inhibited by simple metal chelators, such as 2,2'-bipyridine (bipy), as well as AKG mimics[18], such as N-oxalyl glycine (NOG), pyridine-2,4-dicarboxylic acid (24PDC), and pyridine-2,5-dicarboxylic acid (25PDC), and 3,4-dihydroxybenzoic acid (DHB)[17], as well as by simple metal chelators, such as 2,2'-bipyridine (bipy; FIG. 1B). These compounds suffer from low potency in cellular assays, insufficient selectivity for CP4H, and intolerable cytotoxicity or intolerable cytotoxicity.[19,20] Still, the ethyl ester of DHB (that is, EDHB) is often used as a cellular "P4H" inhibitor,[22,31] even though DHB is not selective for CP4H compared to other FAKGDs, requires high dosing, and leads to an iron-deficient phenotype.[22]

The most potent inhibitors of human CP4Hs identified to date are bipyridinedicarboxylic acids (bipyDCs; FIG. 1B). Two bipyDCs have high potency: 2,2'-bipyridine-4,5'-dicarboxylic acid (bipy45'DC)[38] and 2,2'-bipyridine-5,5'-dicarboxylic acid (bipy55'DC).[21] Both of these bipyDCs inhibit humanCP4H competitively with respect to AKG and bind selectively to human CP4H1 compared to PHD2, another human P4H.[38] An intrinsic property of bipyDCs limits their utility in a biological context. Like bipy itself, bipyDCs form tight complexes with free iron,[38] which is the dominant metal in life.

With high potency and selectivity for human CP4H, the bipyDCs represent an intriguing class of compounds for the development of antifibrotic or antimetastatic therapeutics. However, these compounds possess a variety of undesirable chemical properties that have limited their development thus far. First, the bipyDCs as a class are not cell permeable, requiring the preparation of suitable cell permeable prodrugs. Second, similar to their parent bipy, the bipyDCs are capable of binding and forming complexes with free iron[38] and likely other biologically relevant metals.

Thus, there is a need in the art for inhibitors of CP4H and particularly those that have high potency and selectivity for CP4H compared to other P4Hs. There is a need in the art for selective inhibitors of human CP4H. There is also a need for such inhibitors which exhibit reduced iron binding while retaining inhibitor activity and/or which are cell permeable. Inhibitors of prolyl 4-hydroxylase have been reported.[19, 21, 32-34] Each of these references is incorporated by reference herein for descriptions of synthesis and structure of inhibitors, methods for synthesis of certain esters useful as prodrugs and assessment of inhibition. Compounds specifically disclosed in these references can if necessary be excluded from the claims herein.

U.S. Pat. Nos. 5,658,933 and 5,620,995 report substituted heterocyclic carboxyamide esters as ester prodrugs of prolyl hydroxylase inhibitors. U.S. Pat. No. 6,093,730 reports substituted isoquinoline-3-carboxamides as prolyl-4-hydroxylase inhibitors. These patents are incorporated by reference herein for descriptions of synthesis and structure of inhibitors and assessment of inhibition. Compounds specifically disclosed in these references can if necessary be excluded from the claims herein.

SUMMARY OF THE INVENTION

The invention provides biheteroaryl dicarboxylates and esters, and salts thereof which are useful generally as modulators of CP4H activity, more particularly as inhibitors of CP4H, or further as chemical genetic probes for the study of CP4H function and/or as synthetic intermediates for the preparation of such modulators, inhibitors and/or chemical genetic probes.

In an embodiment, the invention provides compounds of formula I:

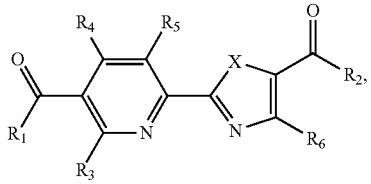

(I)

and salts thereof
where:
X is S, O, NH, or NR,
 where R is an alkyl group having 1-3 carbon atoms;
$R_1$ and $R_2$ independently are —$OR_7$, or —$NHSO_2R_8$,
 where $R_7$ is selected from:
 hydrogen, alkyl, alkenyl, alkoxyalkyl, —R'—CO—R", —R'—CO—O—R", —CO—R", —R'—O—CO—R", —R'—CO—NR", —CO—NR", or —R'—O—CO—NR", and
 $R_8$ is selected from hydrogen, alkyl, aryl, arylalkyl;
$R_3$, $R_4$ and $R_6$ independently are hydrogen, alkyl, alkoxy, alkenyl, alkenoxy, haloalkyl, haloalkenyl, halogen, hydroxyl, hydroxyalkyl, hydroxyalkenyl, aryl, aryloxy, arylalkyl or arylalkyloxy;
$R_5$ is hydrogen, halogen, alkyl having 1-3 carbon atoms, or alkoxy having 1-3 carbon atoms;
—R'— is a divalent straight chain or branched alkylene, and
—R" is an alkyl, alkenyl, arylalkyl, or aryl group.

Alkyl, alkoxy, alkenyl, alkenyloxy, alkylene, arylalkyl, arylalkoxy, aryl or aryloxy groups are unsubstituted or are optionally substituted as defined herein below. In specific embodiments, these groups are substituted with one or more halo, hydroxyl, alkyl, alkoxy, haloalkyl, haloalkoxy, hydroxyalkyl, or hydroxyalkoxy groups. Alkyl groups of substituent groups preferably have 1-3 carbon atoms. Halogens include fluorine, chlorine, bromine and iodine. A specific halogen is fluorine. Another specific halogen is chlorine. Haloalkyl and haloalkoxy groups can be monohalogenated through perhalogenated. A specific haloalkyl group is trifluoromethyl. A specific haloalkoxy group is trifluoromethoxy. Hydroxyalkyl and hydroxyalkoxy groups can contain one or more hydroxyl groups, but more specifically contain 1, 2 or 3 hydroxyl groups.

In specific embodiments, X is S.
In specific embodiments, X is O.
In specific embodiments, X is NH.
In specific embodiments, X is $NCH_3$.
In specific embodiments of formula I, $R_3$, $R_4$, and $R_6$ are hydrogen, halogen or alkyl groups having 1-3 carbon atoms.
In specific embodiments of formula I, $R_3$, $R_4$, and $R_6$ are hydrogen, halogen, phenyl, benzyl or phenethyl groups, where phenyl, benzyl and phenethyl groups are unsubstituted or substituted with one or more non-hydrogen substituents. Specific substituents for phenyl, benzyl and phenethyl groups are halogens, hydroxyl groups, alkyl groups having 1-3 carbon atoms or alkoxy groups having 1-3 carbon atoms.
In specific embodiments of formula I, $R_3$, $R_4$, and $R_6$ are hydrogen or alkyl groups having 1-3 carbon atoms.
In specific embodiments of formula I, $R_3$, $R_4$, and $R_6$ are hydrogens.
In specific embodiments of formula I, $R_5$ is hydrogen, methyl or methoxy.
In specific embodiments of formula I, $R_5$ is methyl or methoxy.
In specific embodiments of formula I, $R_5$ is methyl.
In specific embodiments of formula I, $R_5$ is hydrogen.
In specific embodiments of formula I, $R_3$, $R_4$, and $R_6$ are hydrogen, halogen, alkyl having 1-3 carbon atoms or alkoxy having 1-3 carbon atoms and $R_5$ is hydrogen.
In specific embodiments of formula I, $R_1$ and $R_2$ are independently —$OR_7$ groups where $R_7$ is hydrogen or an alkyl group having 1-8 carbon atoms.
In specific embodiments of formula I, $R_1$ and $R_2$ are independently —$OR_7$ groups where $R_7$ is an alkyl group having 1-8 carbon atoms.
In specific embodiments of formula I, $R_1$ and $R_2$ are independently —$OR_7$ groups where $R_7$ is an alkyl group having 1-3 carbon atoms.
In specific embodiments of formula I, $R_1$ and $R_2$ are —$OR_7$ groups where $R_7$ is a methyl group. In specific embodiments of formula I, $R_1$ and $R_2$ are methoxy groups, $R_5$ is hydrogen and $R_3$, $R_4$ and $R_6$ are hydrogen, halogen, hydroxyl, methyl, or methoxy. In specific embodiments of formula I, $R_1$ and $R_2$ are methoxy groups, and $R_3$, $R_4$, $R_5$ and $R_6$ are hydrogen, halogen, hydroxyl, methyl, or methoxy.
In specific embodiments of formula I, $R_1$ and $R_2$ are ethyl groups. In specific embodiments of formula I, $R_1$ and $R_2$ are ethoxy groups, $R_5$ is hydrogen and $R_3$, $R_4$ and $R_6$ are hydrogen, halogen, hydroxyl, methyl, or methoxy. In specific embodiments of formula I, $R_1$ and $R_2$ are ethoxy groups, and $R_3$, $R_4$, $R_5$ and $R_6$ are hydrogen, halogen, hydroxyl, methyl, or methoxy.
In specific embodiments of formula I, $R_1$ and $R_2$ are —O—$(CH_2)_n$—O—CO—R" groups, where n is 1-3 and R" is an alkyl having 1-6 carbon atoms. In specific embodiments, $R_1$ and $R_2$ are —O—$(CH_2)_n$—O—CO—R" groups, where n is 1-3 and R" is an alkyl having 1-4 carbon atoms. In specific embodiments, $R_1$ and $R_2$ are —O—$(CH_2)_n$—O—CO—R" groups, where n is 1 or 2 and R" is an alkyl having 1-6 carbon atoms. In specific embodiments, $R_1$ and $R_2$ are —O—$(CH_2)$—O—CO—R' groups where R" is an alkyl having 1-4 carbon atoms. In specific embodiments, $R_1$ and $R_2$ are —O—$(CH_2)$—O—CO—R" groups, where R' is a methyl, ethyl, n-propyl or iso-propyl, n-butyl, iso-butyl, sec-butyl or t-butyl group. In specific embodiments, $R_1$ and $R_2$ are —$(CH_2)$—O—CO—R" groups, where R" is t-butyl.
In specific embodiments of formula I, $R_1$ and $R_2$ are —O—$(CH_2)_n$—O—CO—O—R" groups, where n is 1-3 and R" is an alkyl having 1-6 carbon atoms. In specific embodiments, $R_1$ and $R_2$ are —O—$(CH_2)_n$—O—CO—O—R" groups, where n is 1-3 and R" is an alkyl having 1-4 carbon atoms. In specific embodiments, $R_1$ and $R_2$ are —O—$(CH_2)_n$—O—CO—O—R" groups, where n is 1 or 2 and R" is an alkyl having 1-6 carbon atoms. In specific embodiments, $R_1$ and $R_2$ are —O—$(CH_2)$—O—CO—O—R" groups, where R" is an alkyl having 1-4 carbon atoms. In specific embodiments, $R_1$ and $R_2$ are —O—$(CH_2)_n$—O—CO—O—R" groups, where R" is a methyl, ethyl, n-propyl or iso-propyl, n-butyl, iso-butyl, sec-butyl or t-butyl group. In specific embodiments, $R_1$ and $R_2$ are —O—$(CH_2)$—O—CO—O—R" groups, where R" is iso-propyl.
In specific embodiments of formula I, one of $R_1$ or $R_2$ is a —$NHSO_2R_8$ group. In specific embodiments, $R_1$ is a —$NHSO_2R_8$ group and $R_2$ is a —$OR_7$ group. In specific embodiments, $R_2$ is a —$NHSO_2R_8$ group and $R_1$ is a —$OR_7$ group. In specific embodiments, $R_7$ is hydrogen. In specific embodiments, $R_7$ is an alkyl group having 1-8 carbon atoms. In specific embodiments, $R_8$ is hydrogen. In specific embodiments, $R_8$ is an alkyl group having 1-6 carbon atoms. In specific embodiments, $R_8$ is an alkyl group having 1-3 carbon atoms. In specific embodiments, $R_8$ is an unsubstituted phenyl group. In specific embodiments, $R_8$ is an unsubstituted benzyl group. In specific embodiments, $R_8$ is an unsubstituted phenethyl group. In specific embodiments, $R_8$ is a substituted phenyl, benzyl or phenethyl group, having 1, 2 or 3 non-hydrogen substituents, which include among others halogen, hydroxyl, alkyl or alkoxy groups.

In specific embodiments of formula I, $R_1$ and $R_2$ are —$OR_7$ groups where $R_7$ is an alkyl or an alkoxyalkyl. In specific embodiments of formula I, $R_7$ is an unsubstituted alkyl or an alkyl group substituted with one or more halogens. In specific embodiments of formula I, $R_7$ is an alkoxyalkyl group having a total of 2-8 carbon atoms. One or more carbons of the alkoxyalkyl group can be substituted with one or more halogens.

In an embodiment, the invention provides methods for inhibition of CP4H by contacting the CP4H with a compound of formula I or a salt thereof. In more specific embodiments, the method employs a compound of formula I where X is S. In more specific embodiments, the method employs a compound of formula I where X is O. In more specific embodiments, the method employs a compound of formula I where X is NH. In more specific embodiments, the method employs a compound of formula I where X is $NCH_3$. In specific embodiments where X is O or NH or $NCH_3$, $R_1$ and $R_2$ are —$OR_7$, where $R_7$ is an alkyl group having 1-6 carbon atoms, or an alkyl group having 2-6 carbon atoms, or a alkyl group having 1-3 carbon atoms, or a alkyl group having 1-3 carbon atoms.

The invention is also directed to pharmaceutical compositions comprising a therapeutically effective amount of one or more of the compounds of formula I or salts thereof and a pharmaceutically acceptable carrier. Such pharmaceutical compositions are useful for inhibition of CP4H in an individual in need of such inhibition. Compounds of formula I and pharmaceutical compositions comprising them are useful as antifibrotic agents. Compounds of formula I and pharmaceutical compositions comprising them are useful for treatment of fibrotic diseases and disorders. Compounds of formula I and pharmaceutical compositions comprising them are useful for treatment of fibrotic liver disease, idiopathic fibrosis, pulmonary fibrosis, renal fibrosis, cardiac fibrosis, and fibrosis associated with scleroderma or rheumatoid arthritis. Compounds of formula I and pharmaceutical compositions comprising them are useful for treatment of diseases and disorders involving undesirable collage deposition.

The invention is also directed to cellular inhibitors of CP4H which are useful as research reagents in experiments in cultured cells which can be used for inhibition at concentrations that do not cause iron deficiency.

Other embodiments and aspects of the invention will be apparent on review of the detailed description, examples and figures that follow.

BRIEF DESCRIPTIONS OF THE DRAWINGS

Figure 3A:
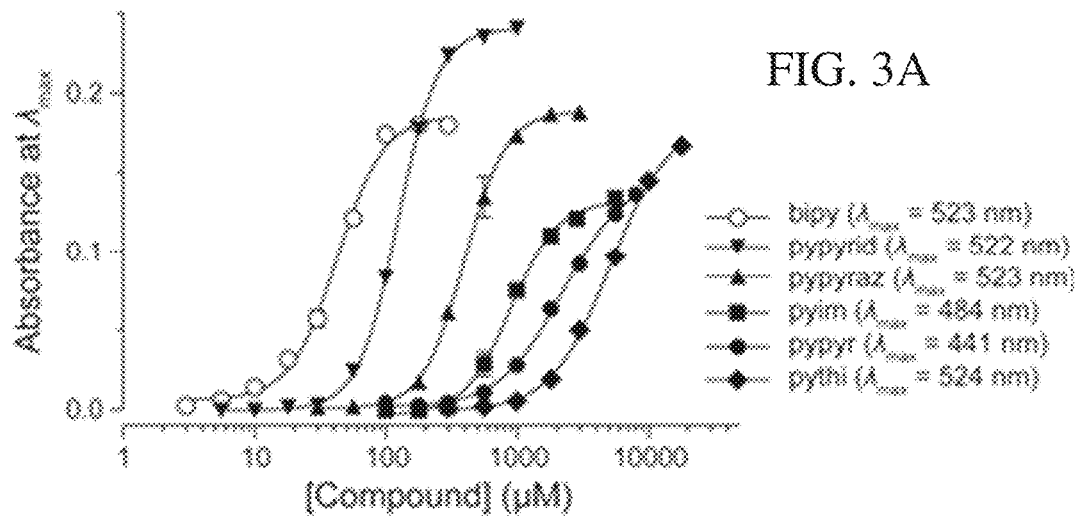

FIG. 3A is a graph of ligand titrations to form iron complexes for biheteroaryl compounds as indicated. Absorbance at $\lambda$max is measured as a function of compound concentration. $R^2 > 0.99$ for all curve fits. The titration curve for bipy was reproduced from Vasta et al., 2015[38]. Titration experiments are described in the Examples.

Figure 3B:
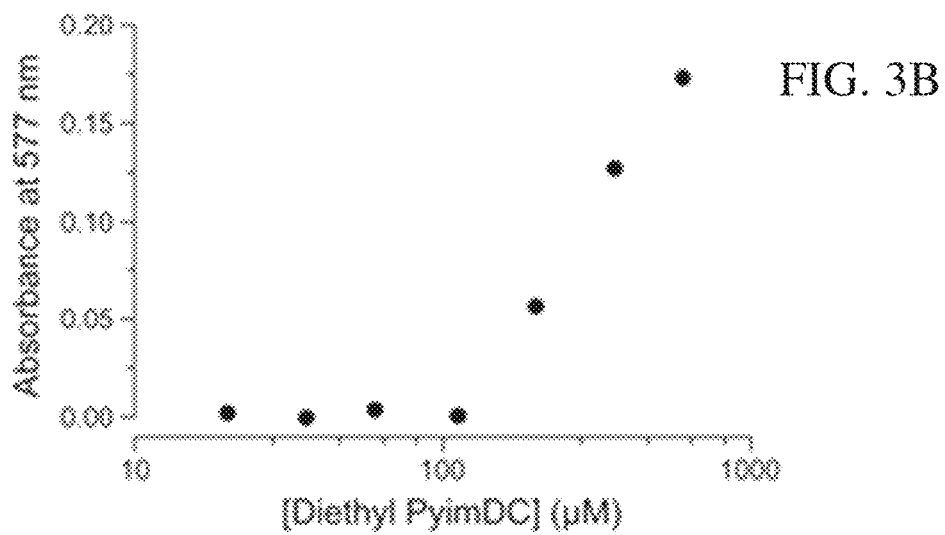

FIG. 3B is a graph of ligand titrations to form iron complexes for diethyl pyimDC. Fe(II) (20 µM) could not be saturated over the range that diethyl pyimDC remained soluble under the assay conditions. Thus, $Fe_{20}$-$EC_{50} > 600$ µM, which was the highest concentration tested.

Figure 4:
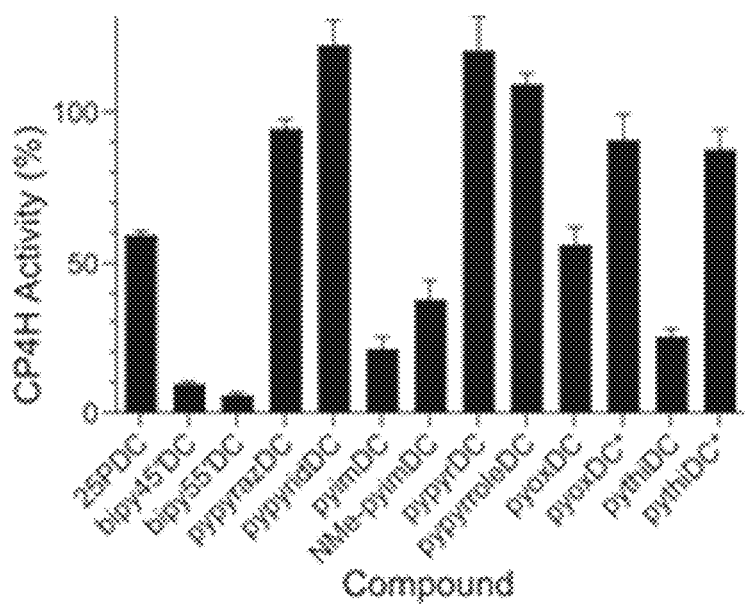

FIG. 4 illustrates the results of a screen for inhibition of human CP4H1. Compounds (10 µM) were screened for inhibition of the catalytic activity of human CP4H1 as described in The Examples. Relative activity values are the mean (±SD) of three replicates. Data for 25PDC, bipy45'DC, and bipy55'DC are from Vasta et al, 2015[38].

Figures 5A, 5B:
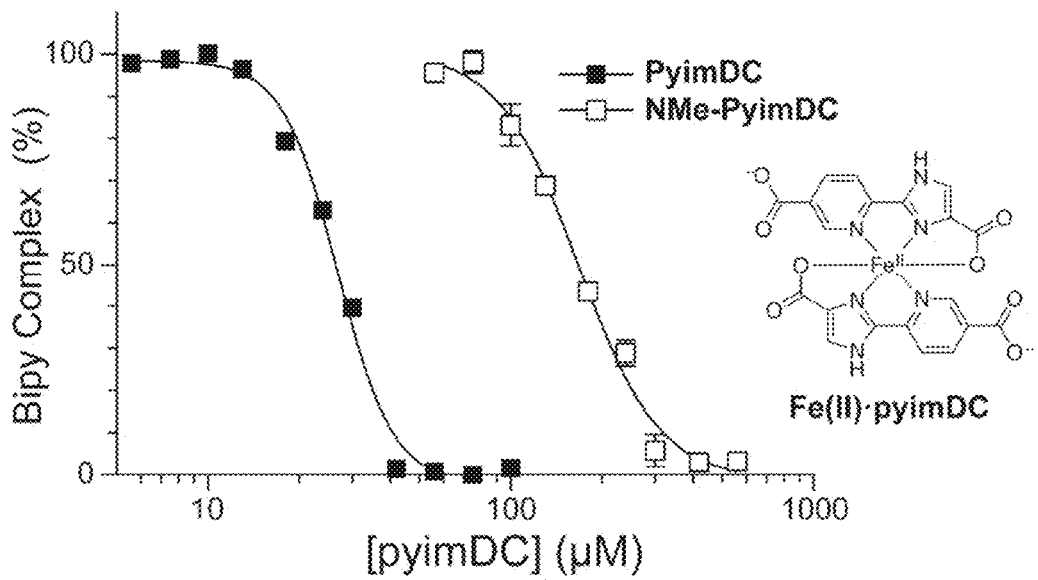

FIG. 5A is a graph illustrating competitive iron-binding by pyimDC with bipy. High concentrations of pyimDC can compete with bipy for complexation with Fe(II), as determined with the assay described in the Examples. These data are consistent with pyimDC forming the depicted 2:1 complex with iron. This phenomenon was dose-dependent and confined to the diacids (not the corresponding esters).

FIG. 5B is a table illustrating structures of NMe-PyinDC, PyimDC and its corresponding methyl and ethyl diesters and providing $EC_{50}$ for complex if observed.

Figure 6A:
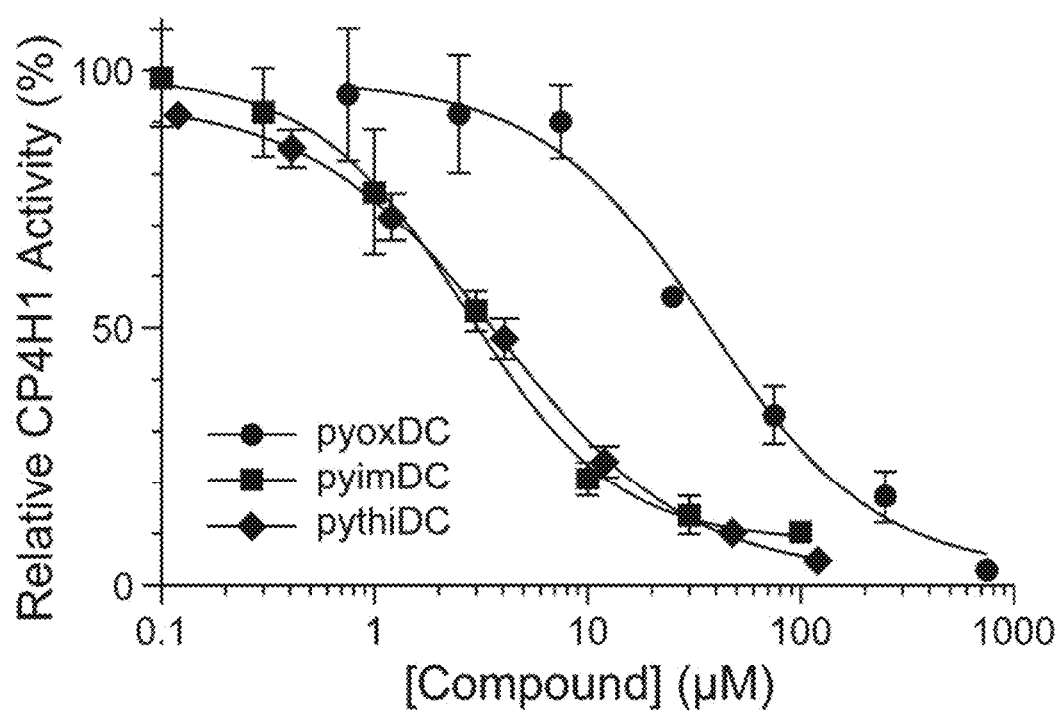

FIG. 6A is a graph showing biheteroaryl dicarboxylates as inhibitors of human CP4H1. Individual points represent the mean (±SD) of three independent experiments. Data were fitted to a dose-response equation to determine IC50 values: pyimDC, (2.6±0.1) µM; pyoxDC, (33±8) µM; pythiDC, (4.0±0.2) µM.

Figure 6B:
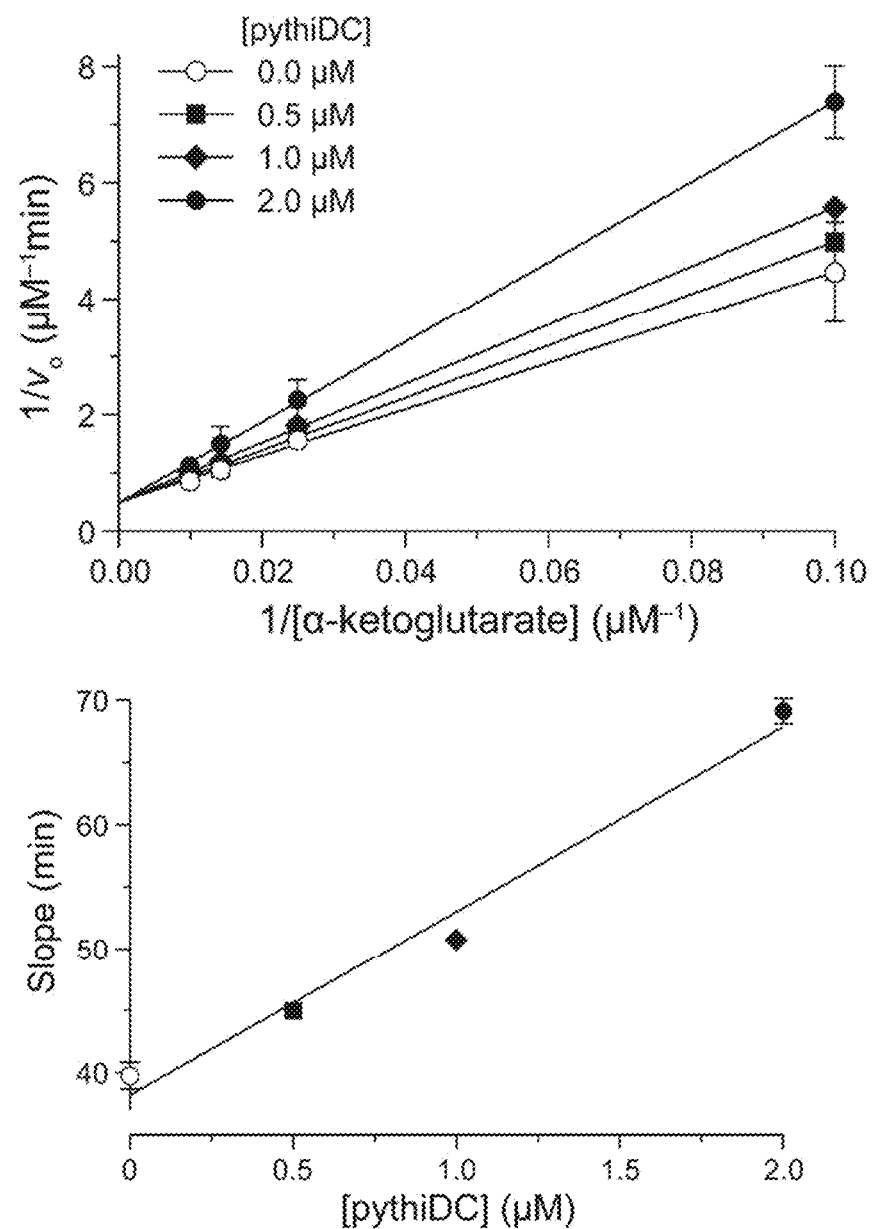

FIG. 6B illustrates Lineweaver-Burke analysis of inhibition by pythiDC. The rate of the reaction catalyzed by CP4H1 with increasing α-ketoglutarate concentration (10-100 µM) was determined in the presence of a fixed concentration of pythiDC (0.0, 0.5, 1.0, or 2.0 µM). Individual points represent the mean (±SE) of two independent experiments (top graph). Data were fitted by linear regression to determine a Ki value of (0.39±0.04) µM for competitive inhibition (bottom graph).

Figure 7:
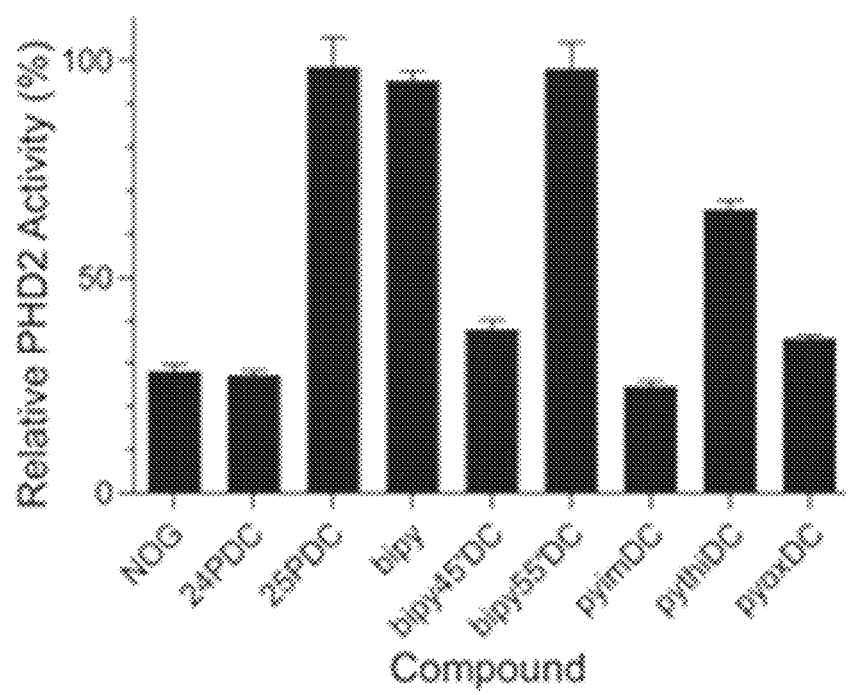

FIG. 7 illustrates the results of a screen for inhibition of human PHD2. Compounds (10 µM) were screened for inhibition of the catalytic activity of human PHD2 as described in The Examples. Relative activity values are the mean (±SD) of three replicates. Data for NOG, 24PDC, 25PDC, bipy, bipy45'DC, and bipy55'DC are from Vasta et al.[38]

Figure 8A:
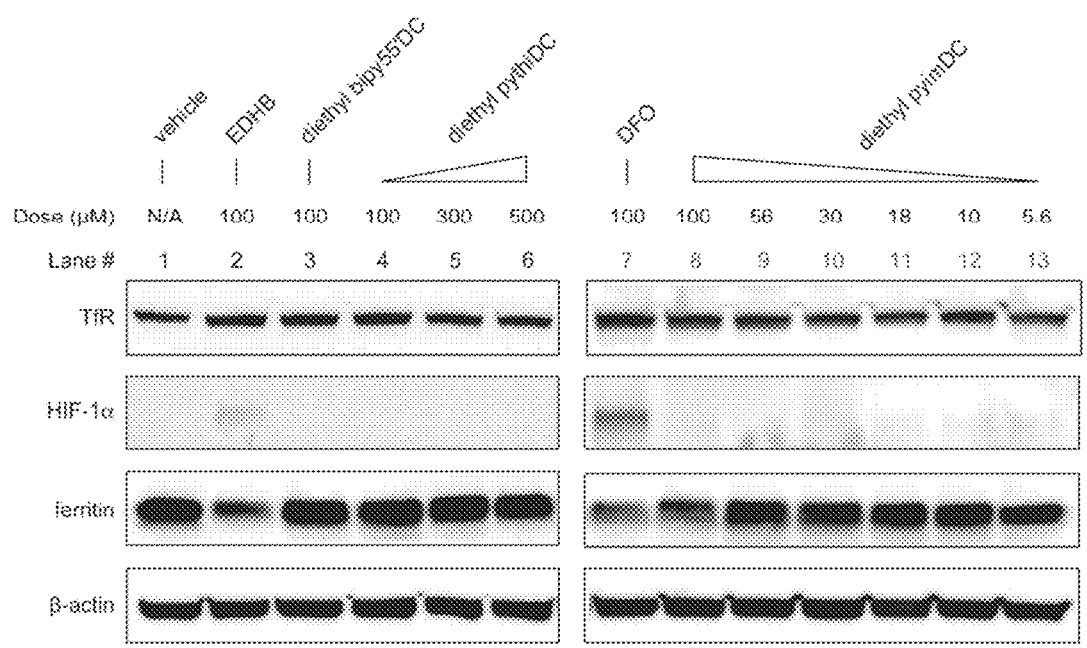

FIG. 8A illustrates the effect of esterified biheteroaryl compounds on iron metabolism. MDA-MB-231 breast cancer cells were treated with deferoxamine (DFO), ethyl dihydroxybenzoate (EDHB), biheteroaryl compounds, or vehicle (DMSO) and then analyzed with immunoblots (*, p<0.05). Blots are representative of at least three replicates.

Figure 8B:
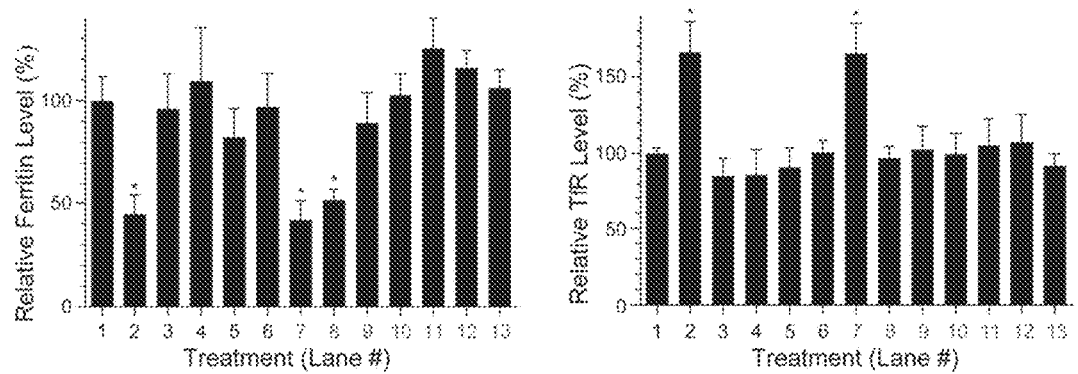

FIG. 8B are densitometric quantitations (n≥3) corresponding to the blots in FIG. 8A and normalized to β-actin. The dose of EDHB (500 µM) is known to diminish collagen secretion significantly.[6] Relative ferritin levels are shown in the left graph. Relative TfR levels are shown in the right graph.

Figure 8C:
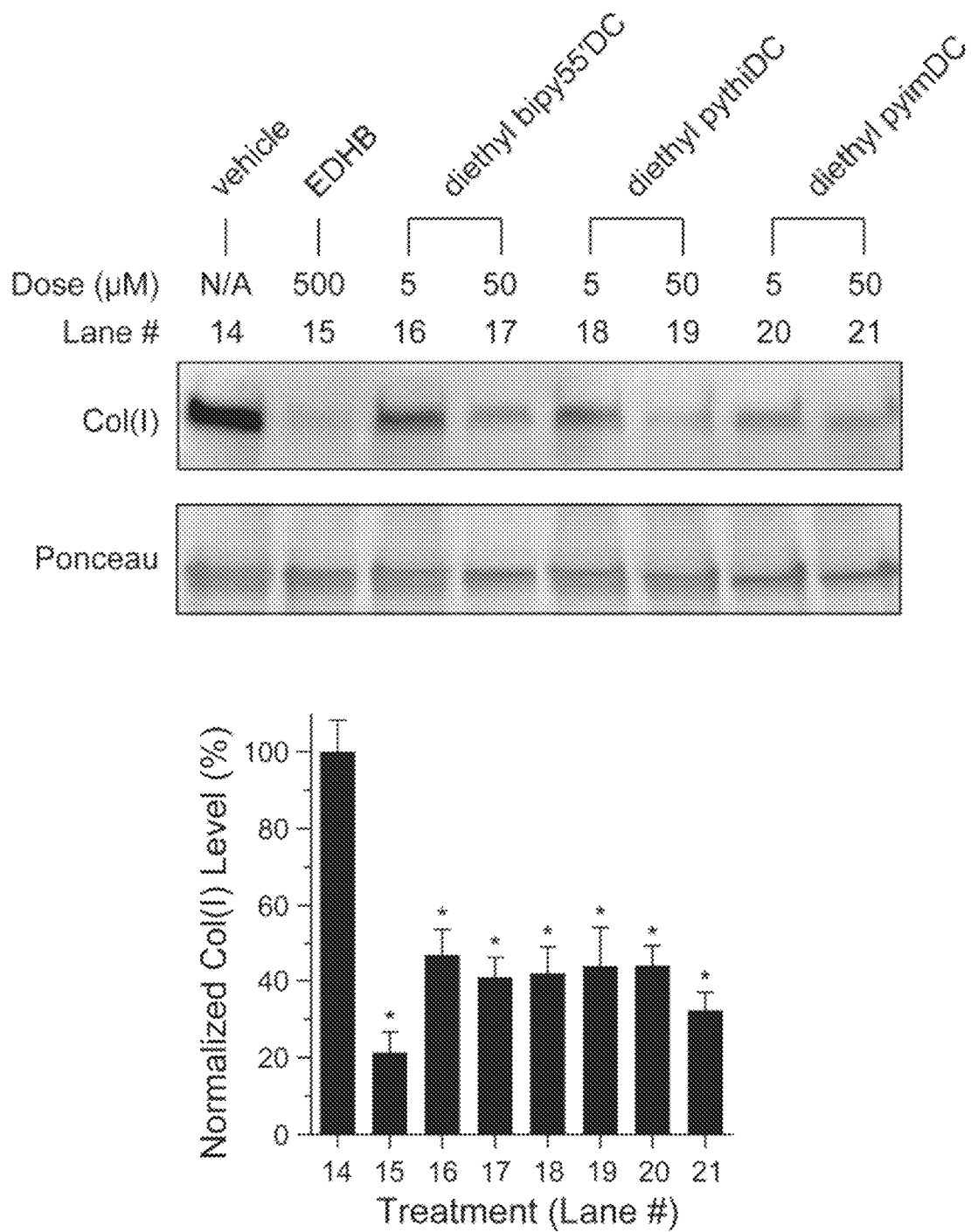

FIG. 8C illustrates the effect of esterified biheteroaryl compounds on collagen secretion into conditioned media. Blots (top) are representative of at least five replicates and densitomeric quantitations (bottom) are normalized to total protein using the Ponceau S-stained blot.

Figure 9A:
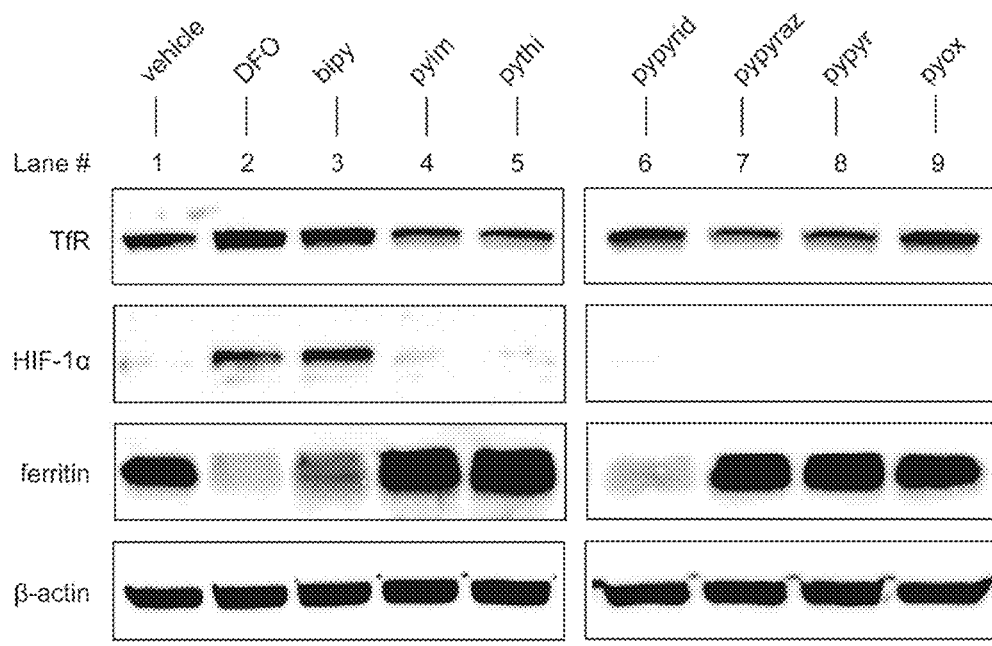

FIG. 9A illustrates the effect of biheteroaryl compounds on iron metabolism in human breast cancer cells. (a) MDA-MB-231 breast cancer cells were treated with deferoxamine (DFO), biheteroaryl compounds, or vehicle (DMSO) as described in the Examples, and analyzed with an immunoblot (*, p<0.05).

Figure 9B:
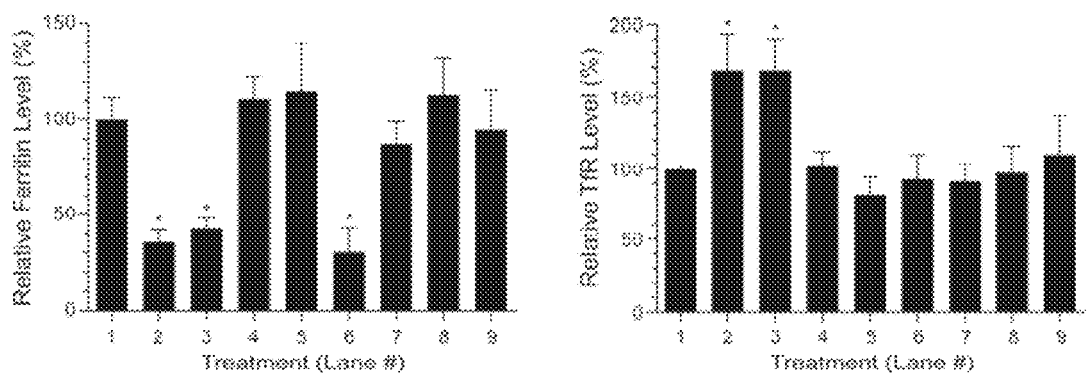

FIG. 9B are densitometric quantitations corresponding to the blots in FIG. 9A. Relative ferritin levels are shown in the left graph. Relative TfR levels are shown in the right graph.

Figure 10:
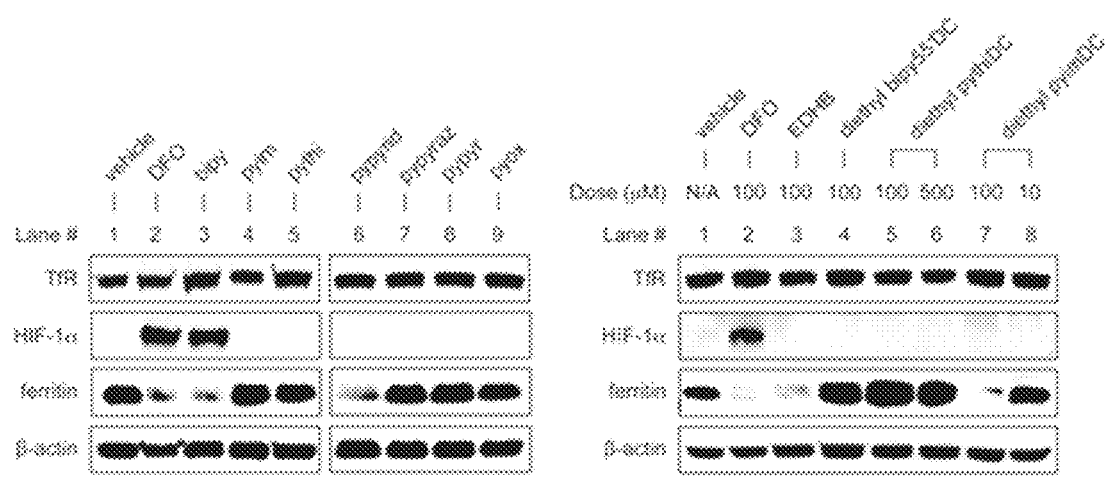

FIG. 10 illustrates the effect of biheteroaryl compounds and their diethyl esters on iron metabolism in human embryonic kidney cells. In the image on the left, HEK293T cells were treated with biheteroaryl compounds (100 μM), deferoxamine (DFO, 100 μM), or vehicle (DMSO) as described in the Examples, and analyzed with an immunoblot. In the image on the right HEK293T cells were treated with esterified biheteroaryl compounds, deferoxamine (DFO), ethyl dihydroxybenzoate (EDHB), or vehicle (DMSO), and analyzed with an immunoblot.

Figure 11:
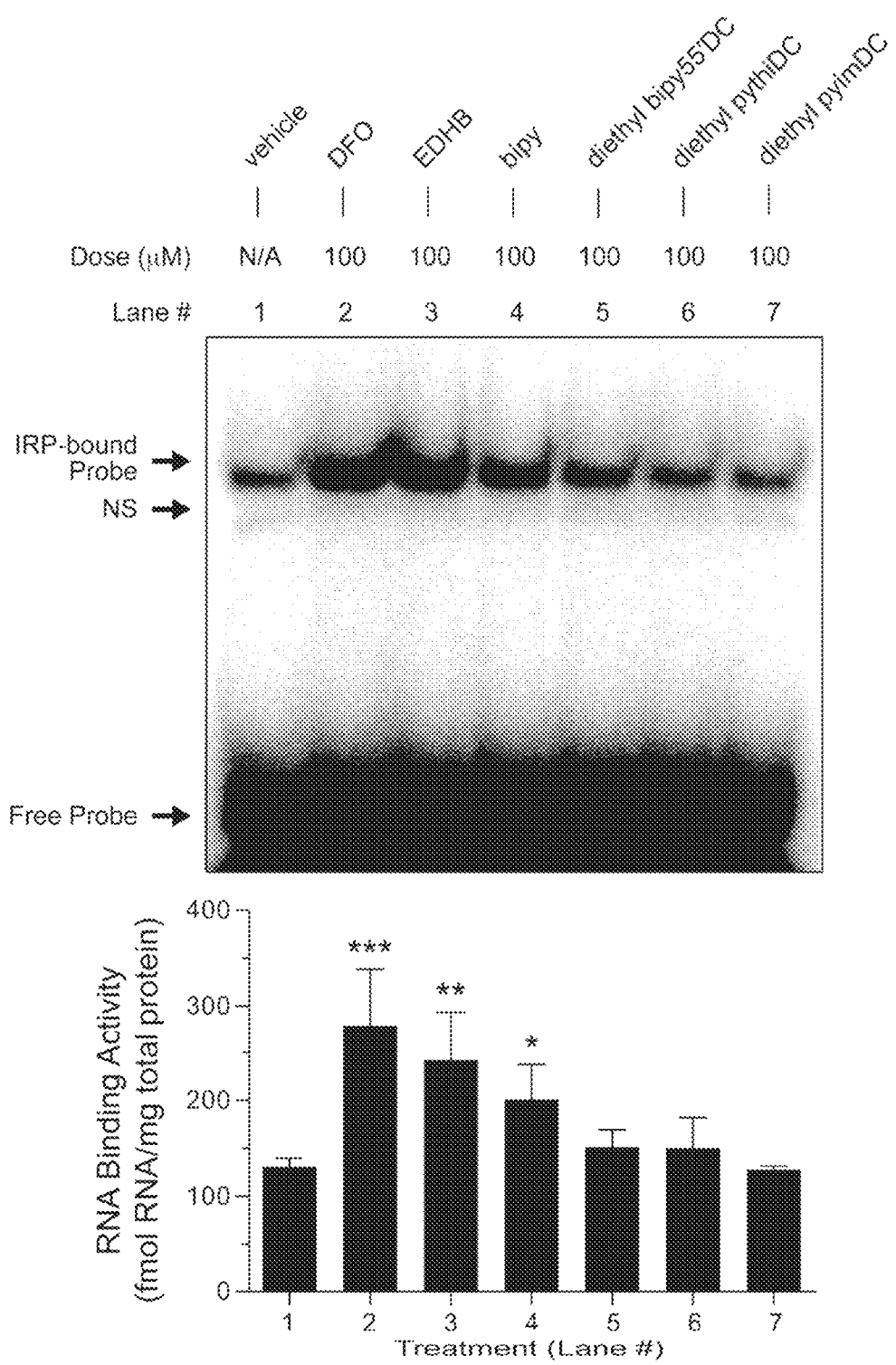

FIG. 11 illustrates the effect of esterified biheteroaryl compounds on IRE Binding by IRPs in Human Breast Cancer Cells. MDA-MB-231 cells were treated with esterified biheteroaryl compounds, deferoxamine (DFO), ethyl dihydroxybenzoate (EDHB), or vehicle (DMSO) as described in the Examples, and analyzed by an electrophoretic mobility shift assay (EMSA) using a $^{32}$P-labeled RNA ligand for IRPs. The top graph is an EMSA assay representative of 3 replicates. The bottom graph is densitometric quantitations of the EMSAs represented in the top graph. Quantitations (n=3) were obtained by densitometry and derived from the digital light units using a calibration curve obtained by scintillation counting and normalized to total protein and total RNA. Under these conditions, IRP1- and IRP2-bound RNA comigrate in the band labeled "IRP-bound Probe". *p<0.05, p<0.01, *p<0.001.

Figure 12:
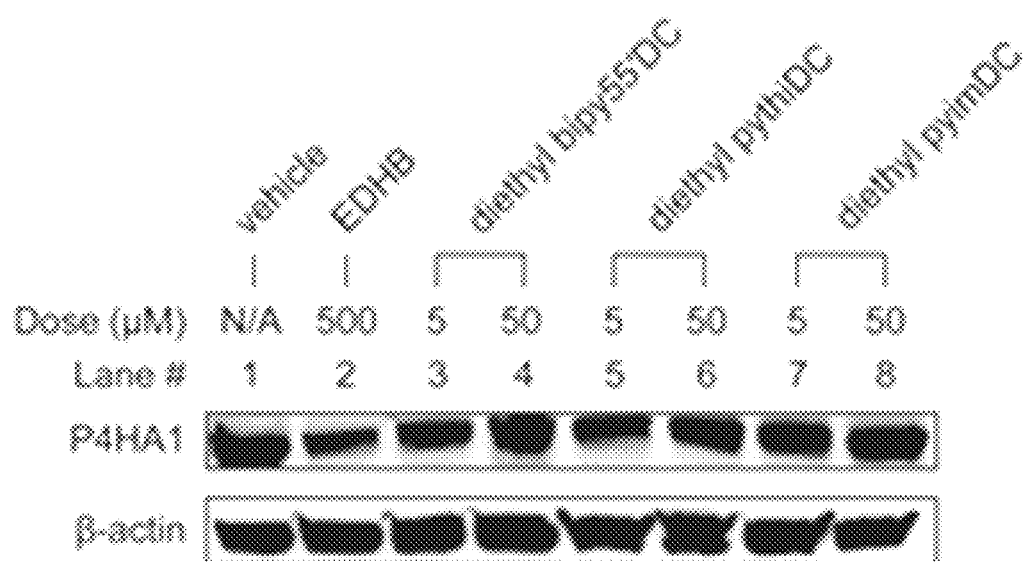

FIG. 12 illustrates the effect of esterified biheteroaryl compounds on P4HA1 levels in human breast cancer cells. MDA-MB-231 cells were treated with esterified biheteroaryl compounds, deferoxamine (DFO), ethyl dihydroxybenzoate (EDHB), or vehicle (DMSO) as described in the Examples, and then analyzed with an immunoblot. Blots are representative of at least 2 replicates.

DETAILED DESCRIPTION OF THE INVENTION

The invention is based at least in part on the preparation and investigation of certain biheterocyclic compounds of formula X:

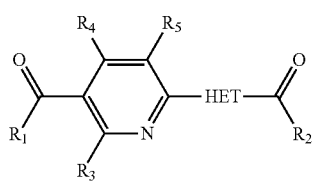

where $R_1$-$R_5$ are as defined for formula I and HET is selected from:

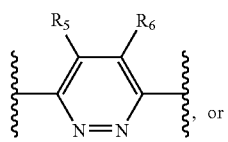

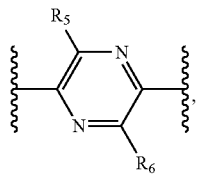

where $R_5$ is hydrogen, halogen, alkyl having 1-3 carbon atoms, or alkoxy having 1-3 carbon atoms and $R_6$ is as defined for formula I;

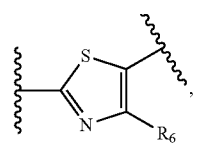

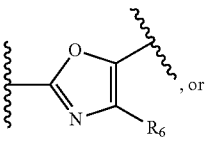

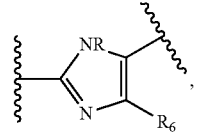

where $R_6$ is as defined for formula I and R is hydrogen or an alkyl having 1-3 carbons atoms and is specifically hydrogen or is specifically methyl;

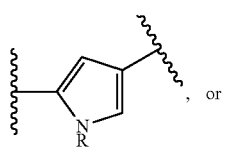

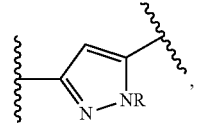

where R is hydrogen or an alkyl group. R is more specifically hydrogen or methyl.

Certain compounds of formula X modulate the activity of collagen prolyl 4-hydroxylases.

Certain compounds of formula X modulate the activity of human collagen prolyl 4-hydroxylase.

Certain compounds of formula X inhibit the activity of collagen prolyl 4-hydroxylases. Certain compounds of formula X inhibit the activity of human collagen prolyl 4-hydroxylase. Certain compounds of formula X increase the activity of collagen prolyl 4-hydroxylases. Certain compounds of formula X increase the activity of human collagen prolyl 4-hydroxylase.

Compounds of formula X wherein HET is A1, C1 or C2 are of particular interest. Compounds of formula X where HET is B1, B2 or B3 are of particular interest.

In specific embodiments of formula X, HET is A1.
In specific embodiments of formula X, HET is A2.
In specific embodiments of formula X, HET is B1.
In specific embodiments of formula X, HET is B2.
In specific embodiments of formula X, HET is B3.
In specific embodiments of formula X, HET is C1.
In specific embodiments of formula X, HET is C2.

In specific embodiments, X is NR, where R is an alkyl group having 1-3 carbon atoms or more specifically R is methyl. Y is C and Z is N. In more specific embodiments, R is methyl.

In specific embodiments of formula X, and for each embodiment of HET, $R_3$, $R_4$, and $R_6$ are hydrogen, halogen or alkyl groups having 1-3 carbon atoms.

In specific embodiments of formula X, and for each embodiment of HET, $R_3$, $R_4$, and $R_6$ are hydrogen, halogen, phenyl or benzyl groups, where phenyl and benzyl groups are unsubstituted or substituted with one or more non-hydrogen substituents. Specific substituents for phenyl and benzyl groups are halogens, hydroxyl groups, alkyl groups having 1-3 carbon atoms or alkoxy groups having 1-3 carbon atoms.

In specific embodiments of formula X, and for each embodiment of HET, $R_3$, $R_4$, and $R_6$ are hydrogen or alkyl groups having 1-3 carbon atoms.

In specific embodiments of formula X, and for each embodiment of HET, $R_3$, $R_4$, and $R_6$ are hydrogens.

In specific embodiments of formula X, and for each embodiment of HET, $R_5$ is hydrogen, methyl or methoxy.

In specific embodiments of formula X, and for each embodiment of HET, $R_5$ is methyl or methoxy.

In specific embodiments of formula X, and for each embodiment of HET, $R_5$ is methyl.

In specific embodiments of formula X, and for each embodiment of HET, $R_5$ is hydrogen.

In specific embodiments of formula X, and for each embodiment of HET, $R_3$, $R_4$, and $R_6$ are hydrogen, halogen, alkyl having 1-3 carbon atoms or alkoxy having 1-3 carbon atoms and $R_5$ is hydrogen.

In specific embodiments of formula X, and for each embodiment of HET, $R_1$ and $R_2$ are independently —$OR_7$ groups where $R_7$ is hydrogen or an alkyl group having 1-8 carbon atoms.

In specific embodiments of formula X, and for each embodiment of HET, $R_1$ and $R_2$ are independently —$OR_7$ groups where $R_7$ is an alkyl group having 1-8 carbon atoms.

In specific embodiments of formula X, and for each embodiment of HET, $R_1$ and $R_2$ are independently —$OR_7$ groups where $R_7$ is an alkyl group having 1-3 carbon atoms.

In specific embodiments of formula X, and for each embodiment of HET, $R_1$ and $R_2$ are —$OR_7$ groups where $R_7$ is a methyl group. In specific embodiments of formula X, and for each embodiment of HET, $R_1$ and $R_2$ are methoxy groups, $R_5$ is hydrogen and $R_3$, $R_4$ and $R_6$ are hydrogen, halogen, hydroxyl, methyl, or methoxy. In specific embodiments of formula X, and for each embodiment of HET, $R_1$ and $R_2$ are methoxy groups, and $R_3$, $R_4$, $R_5$ and $R_6$ are hydrogen, halogen, hydroxyl, methyl, or methoxy.

In specific embodiments of formula X, and for each embodiment of HET, $R_1$ and $R_2$ are ethyl groups. In specific embodiments of formula X, and for each embodiment of HET, $R_1$ and $R_2$ are ethoxy groups, $R_5$ is hydrogen and $R_3$, $R_4$ and $R_6$ are hydrogen, halogen, hydroxyl, methyl, or methoxy. In specific embodiments of formula X, and for each embodiment of HET, $R_1$ and $R_2$ are ethoxy groups, and $R_3$, $R_4$, $R_5$ and $R_6$ are hydrogen, halogen, hydroxyl, methyl, or methoxy. In specific embodiments of formula X, and for each embodiment of HET, $R_1$ and $R_2$ are —O—$(CH_2)$n-O—CO—R" groups where n is 1-3 and R" is an alkyl having 1-6 carbon atoms. In specific embodiments, $R_1$ and $R_2$ are —O—$(CH_2)$n-O—CO—R" groups where n is 1-3 and R" is an alkyl having 1-4 carbon atoms. In specific embodiments, $R_1$ and $R_2$ are —O—$(CH_2)$n-O—CO—R" groups where n is 1 or 2 and R" is an alkyl having 1-6 carbon atoms. In specific embodiments, $R_1$ and $R_2$ are —O—$(CH_2)$—O—CO—R' groups where R" is an alkyl having 1-4 carbon atoms. In specific embodiments, $R_1$ and $R_2$ are —O—$(CH_2)$—O—CO—R" groups where R' is a methyl, ethyl, n-propyl or iso-propyl, n-butyl, iso-butyl, sec-butyl or t-butyl group. In specific embodiments, $R_1$ and $R_2$ are —$(CH_2)$—O—CO—R" groups where R" is t-butyl.

In specific embodiments of formula X, and for each embodiment of HET, $R_1$ and $R_2$ are —O—$(CH_2)$n-O—CO—O—R" groups where n is 1-3 and R" is an alkyl having 1-6 carbon atoms. In specific embodiments, $R_1$ and $R_2$ are —O—$(CH_2)$n-O—CO—O—R" groups where n is 1-3 and R" is an alkyl having 1-4 carbon atoms. In specific embodiments, $R_1$ and $R_2$ are —O—$(CH_2)$n-O—CO—O—R" groups where n is 1 or 2 and R" is an alkyl having 1-6 carbon atoms. In specific embodiments, $R_1$ and $R_2$ are —O—$(CH_2)$—O—CO—O—R" groups where R" is an alkyl having 1-4 carbon atoms. In specific embodiments, $R_1$ and $R_2$ are —O—$(CH_2)$n-O—CO—O—R" groups where R" is a methyl, ethyl, n-propyl or iso-propyl, n-butyl, iso-butyl, sec-butyl or t-butyl group. In specific embodiments, $R_1$ and $R_2$ are —O—$(CH_2)$—O—CO—O—R" groups where R' is iso-propyl.

In specific embodiments of formula X, and for each embodiment of HET, one of $R_1$ or $R_2$ is a —$NHSO_2R_8$ group. In specific embodiments, $R_1$ is a —$NHSO_2R_8$ and $R_2$ is a —$OR_7$ group. In specific embodiments, $R_2$ is a —$NHSO_2R_8$ and $R_1$ is a hydrogen or a —$OR_7$ group. In specific embodiments, $R_7$ is hydrogen. In specific embodiments, $R_7$ is an alkyl group having 1-8 carbon atoms. In specific embodiments, $R_8$ is hydrogen. In specific embodiments, $R_8$ is an alkyl group having 1-6 carbon atoms. In specific embodiments, $R_8$ is an alkyl group having 1-3 carbon atoms. In specific embodiments, $R_8$ is an unsubstituted phenyl group. In specific embodiments, $R_8$ is an unsubstituted benzyl group. In specific embodiments, $R_8$ is an unsubstituted phenethyl group.

In specific embodiments of formula X, and for each embodiment of HET, $R_1$ and $R_2$ are —$OR_7$ groups where $R_7$ is alkyl or alkoxyalkyl.

In an embodiment, the invention provides methods for modulation of CP4H by contacting the CP4H with a compound of formula X or a salt thereof. In more specific embodiments, the method employs a compound of formula X where Het is A1, B1, B2, B3, C1 or C2.

The terms alkyl or alkyl group refer to a monoradical of a straight-chain or branched saturated hydrocarbon. Alkyl groups include straight-chain and branched alkyl groups. Unless otherwise indicated alkyl groups have 1-12 carbon atoms (C1-C12 alkyl groups) and preferred are those that contain 1-8 carbon atoms (C1-C8 alkyl groups), more preferred are those that contain 1-6 carbon atoms (C1-C6 alkyl groups) and yet more preferred are those that contain 1-3 carbon atoms (C1-C3 alkyl groups). Alkyl groups are optionally substituted with one or more non-hydrogen substituents as described herein. Specific substituted alkyl groups include haloalkyl groups and hydroxyalkyl groups.

Exemplary alkyl groups include methyl, ethyl, n-propyl, iso-propyl, n-butyl, s-butyl, t-butyl, n-pentyl, branched-pentyl, n-hexyl, branched hexyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alky groups. Substituted alkyl groups include alkyl groups substituted with one or more hydroxyl groups. Particular hydroxyalkyl groups are those having 1, 2, 3 or 4 hydroxyl groups and particularly those having one hydroxyl group. The term alkyl group further includes cycloalkyl groups which are those alkyl groups which have 1 ring or which are bicyclic or tricyclic. In specific embodiments, cycloalkyl groups have one ring having 5-8 carbon atoms and preferably have one 5- or 6-carbon ring. Alkyl groups can be unsubstituted. Alkyl groups can be other than cycloalkyl groups.

An alkoxy group is an alkyl group, as broadly discussed above, linked to oxygen (—O—$R_{alkyl}$). The term alkoxyalkyl refers to a group having two or more alkylene or alkyl moieties each linked through oxygen atoms, e.g., -alkylene-O-alkyl, -alkylene-O-alkylene-O-alkyl, etc. or more generically —O-(alkylene-O)n-alkyl, where n is an integer from 1 to 20. Alkylene groups can contain 1-12 carbon atoms or more specifically 1-6 carbon atoms or more specifically 1-3 carbon atoms. Alkyl groups can contain 1-12 carbon atoms, 1-6 carbon atoms or 1-3 carbon atoms. Alkoxyalkyl groups can contain 1-22 carbon atoms and 1-10, 1-6 or 1-3 oxygen atoms. Such groups can also be designated ether groups. The alkylene moiety can be straight-chain or branched. The alkyl group can be straight-chain or branched. Specific alkoxyalkyl groups include: —$(CH_2—O)_n$—$CH_3$, where n is 1-6 or 1-3, —$(CH_2CH_2—O)_n$—$CH_3$, where n is 1-6 or 1-3, or —$(CH_2CH_2CH_2—O)_n$—$CH_3$, where n is 1-6 or 1-3, —$(CH_2)$n-O—$(CH_2—CH(Ra)—CH_2)$—O—$(CH_2)_m$—$CH_3$, where n is 1-6, m is 1-6 and Ra is an alkyl having 1-4 carbon atoms.

The terms alkenyl or alkenyl group refer to a monoradical of a straight-chain or branched hydrocarbon having one or more double bonds. Unless otherwise indicated alkenyl groups have 2-12 carbon atoms (C2-C12 alkenyl groups) and preferred are those that contain 2-8 carbon atoms (C1-C8 alkenyl groups), more preferred are those that contain 2-6 carbon atoms (C2-C6 alkyl groups) and yet more preferred are those that contain 2-3 carbon atoms (C2-C3 alkyl groups). Alkenyl groups are optionally substituted with one or more non-hydrogen substituents as described herein. Specific substituted alkenyl groups include haloalkenyl groups and hydroxyalkenyl groups. Exemplary alkenyl groups include ethenyl, n-propenyl, iso-propenyl, n-butenyl, s-butenyl, n-pentenyl, branched-pentenyl, n-hexenyl, branched hexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups. Substituted alkenyl groups include alkenyl groups substituted with one or more hydroxyl groups. Particular hydroxyalkenyl groups are those having 1, 2, 3 or 4 hydroxyl groups and particularly those having one hydroxyl group. The term alkenyl group further includes cycloalkenyl groups which are those alkenyl groups which have 1 ring or which are bicyclic or tricyclic. In specific embodiments, cycloalkenyl groups have one ring having 5-8 carbon atoms and preferably have one 5- or 6-carbon ring. Specific alkenyl groups are those having one double bond. Specific alkenyl groups are those having 2 double bonds. Alkenyl groups can be unsubstituted. Alkenyl groups can be other than cycloalkyl groups. Alkenyl groups include those having formula —CH=CH—Rc, where Rc is H or a straight chain or branched alkyl group having 1-10 carbon atoms. Alkenyl groups include those having formula —$(CH_2)_n$CH=CH—Rc, where n is 1-10 and Rc is H or a straight chain or branched alkyl group having 1-10 carbon atoms. Alkenyl groups include those having formula —$(CH_2)$n-CH=CH—$(CH_2)$m-H, where m and n are integers the sum of which is 10. Alkenyl groups include those having formula —$(C(Ra)_2)$n-CRa=CRa—$(C(Ra)_2)$m-Rb, where each Ra is hydrogen or an alkyl group and Rb is a hydrogen or an alkyl group and the total number of carbons is 4-12. Alkenyloxy refers to an alkenyl group linked through oxygen (—O—$R_{alkenyl}$).

Alkylene refers to divalent moieties derived formally from alkyl groups as described above by removal of an additional hydrogen e.g., —$(CH_2)_a$—, where a is 1-20. Alkylene moieties are optionally branched or substituted, e.g., —$(CH_2)_a$—$CH(CH_3)$—$(CH_2)_b$—, where the sum of a+b is 1 to 20. Alkylene groups can have 1-20, 1-10, 1-6 or 1-3 carbon atoms. Alkylene groups can have 1, 2, 3, 4, 5 or 6 carbon atoms.

Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted as described herein. Aryl groups include heteroaryl groups having 1-3 heteroatoms in the one or more 5- or 6-member rings. Heteroatoms include O, S and N. Aryl groups include those having only carbons in the rings. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Specific aryl groups are unsubstituted and substituted phenyl groups. Specific aryl rings include unsubstituted or substituted naphthyl groups. Specific aryl groups are halogenated phenyl groups.

An aryloxy group is an aryl group, as broadly discussed above, linked to oxygen (—O—$R_{aryl}$).

Arylalkyl groups are alkyl groups substituted with an aryl group. Specific arylalkyl groups are benzyl (—$CH_2$-phenyl) or phenethyl (—$CH_2$—$CH_2$-phenyl). Arylalkoxy groups are arylalkyl groups linked to oxygen (—O—$R_{arylalkyl}$)

Groups (e.g., alkyl, alkylene, aryl, arylalkyl, alkenyl, phenyl and benzyl) herein are optionally substituted most generally, for example, with one or more oxo group, thioxo group, halogen, nitro, cyano, cyanate, azido, thiocyano, isocyano, isothiocyano, sulfhydryl, hydroxyl, alkyl, alkoxy, alkylthio, —$COR_S$, —COH, —$OCOR_S$, —OCOH, —CO—$OR_S$, —CO—OH, —CO—O—CO—$R_S$, —$CON(R_S)_2$, —$CONHR_S$, —$CONH_2$, —$NR_S$—$COR_S$, —$NHCOR_S$, —$NHR_S$, —$N(R_S)_2$, —O—$SO_2$—$R_S$, —$SO_2$—$R_S$, —$SO_2$—$NHR_S$, —$SO_2$—$N(R_S)_2$, —$NR_S$—$SO_2$—$R_S$, —NH—$SO_2$—

R$_S$, —NR$_S$CO—N(R$_S$)$_2$, or —NH—CO—NHR$_S$, where each R independently is an alkyl group, particularly an alkyl group having 1-6 or 1-3 carbon atoms.

In specific embodiments, optional substitution is substitution with 1-12 non-hydrogen substituents. In specific embodiments, optional substitution is substitution with 1-6 non-hydrogen substituents. In specific embodiments, optional substitution is substitution with 1-3 non-hydrogen substituents. In specific embodiments, optional substituents contain 6 or fewer carbon atoms. In specific embodiments, optional substitution is substitution by one or more halogen, hydroxy group, cyano group, oxo group, thioxo group, unsubstituted C1-C6 alkyl group or an unsubstituted aryl group. The term oxo group and thioxo group refer to substitution of a carbon atom with a =O or a =S to form respectively —CO— (carbonyl) or —CS— (thiocarbonyl) groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Compounds of the invention of formula X and I are synthesized by methods as described herein or as described in references 19, 21, 32-34 or in U.S. Pat. Nos. 5,620,995, 5,658,933 or 6,093,730 or by routine adaptation of such methods in view of methods that are well known in the art by routine choice of starting material or reagents. Such starting materials and reagents are commercially available or can be prepared by art-known methods.

Compounds of the invention which are esters of corresponding mono- or di-carboxylic acids are believed to be cleaved in vivo in organisms or in cells to form the corresponding carboxylic acid or salts thereof.

In an embodiment, the invention provides methods for modulating the activity of collagen prolyl 4-hydoxylase activity in vitro and in vivo. Modulation of collagen prolyl 4-hydoxylase activity facilitates modulation of the biosysnthesis of collagen. Thus, the invention provides a method for modulating the biosynthesis of collagen. CP4H activity is modulated by contact thereof with one or more compounds of formula X. In an embodiment, in vivo inhibition is inhibition in cells In an embodiment, the invention provides methods for inhibiting the activity of collagen prolyl 4-hydoxylase activity in vitro and in vivo. Inhibition of collagen prolyl 4-hydoxylase activity facilitates modulation of the biosysnthesis of collagen. Thus, the invention provides a method for inhibiting the biosynthesis of collagen. CP4H activity is inhibited by contact thereof with one or more compounds of formula X.

In an embodiment, the invention provides methods for treating or preventing fibrotic diseases or disorders and the symptoms associated therewith. Fibrosis can affect any organ or tissue in the body and include fibroses of the lung, liver, skin and atherosclerosis. Fibrotic diseases and disorders also include scleroderma and scarring after burns, or other injuries or after surgery. Fibrotic diseases also include fibroproliferative disorders, including liver cirrhosis, pulmonary fibrosis, and systemic sclerosis, among others. Collagen is deposited during fibrosis. Inhibition of collagen prolyl 4-hydroxylase results in inhibition of collagen biosynthesis, which reduces undesired collagen deposition.

Gilkes et al.[6] reports that the presence of hypoxia and fibrosis within the primary tumor are two major risk factors for metastasis of human breast cancer. They report further that hypoxia-inducible factor 1 activates the transcription of genes encoding collagen prolyl hydroxylases. These genes function for collagen deposition by breast cancer cells. They report that expression of collagen prolyl hydroxylases promotes cancer cell alignment along collagen fibers, resulting in enhanced invasion and metastasis to lymph nodes and lungs. They report that ethyl 3,4-dihydroxybenzoate, a prolyl hydroxylase inhibitor, decreases tumor fibrosis and metastasis in a mouse model of breast cancer. Thus, the present invention provides inhibitors of CP4H, for use in treatment of cancer, in particular breast cancer, for preventing or inhibiting metastasis of breast cancer. More specifically, the invention provides compounds of formula I for such treatment. Pharmaceutical compositions comprising one or more compounds of formula I in an amount effective for inhibition of CP4H in vivo for such treatment are provided. The compounds, compositions and methods of this invention can be combined if desired with art-known methods of treatment of cancer, particularly breast cancer.

The invention provides pharmaceutical compositions comprising a pharmaceutically effective amount of one or more compounds and/or salts of formula I and a pharmaceutically acceptable carrier or excipient. The compounds and salts thereof of the invention can be used to prepare medicaments for the treatment and prevention of fibrotic diseases and disorders and the symptoms associated therewith.

The term "pharmaceutically effective amount" refers to an amount effective for treatment of a fibrotic disease or disorder in an individual (human or other mammal) in need of such treatment either by administration of a single compound or salt of formula I or in combination with other agents. The pharmaceutically effective amount of a given compound when administered as the only active ingredient may differ from its pharmaceutically effective amount when administered with other active ingredients. It will be appreciated that the pharmaceutically effective amount of a compound may differ from that of a salt of the same compound. Treating includes the alleviation of symptoms of a particular disorder in a patient or a measurable improvement of a parameter associated with a particular disorder. Treating includes treatment to prevent, delay or decrease undesired deposition of collagen. The term "prophylactically effective amount" refers to an amount of a compound or salt of the invention effective in preventing such deposition in an individual. The term "CP4H inhibitory effective amount" is that amount of a compound effective for inhibiting a given collagen prolyl 4-hydoxylase. The amount effective in vivo in an organism or in a cell may be different. The term "collagen inhibitory effective amount" is that amount of a compound that is effective for inhibiting collagen biosynthesis.

In general, the compounds and salts of formula I of the invention can be employed for treatment as is known in the art for other collagen prolyl 4-hydoxylase inhibitors as described in one or more of the patent documents cited herein and as is known in the art.

As used herein, the term "individual" includes reference to a mammal, including a human. Compounds of the invention of formula I can be administered in the form of pharmaceutically acceptable salts which include the following non-limiting examples: alkali metal salts, such as those of lithium, potassium and sodium; alkali earth metal salts, such as those of barium, calcium and magnesium; transition metal salts, such as those of zinc; and other metal salts, such as those of aluminum, sodium hydrogen phosphate and disodium phosphate; salts of nitrates, borates, methanesulfonates, benzene sulfonates, toluenesulfonates, salts of mineral acids, such as those of hydrochlorides, hydrobromides, hydroiodides and sulfates; salts of organic acids, such as those of acetates, trifuoroacetates, maleates, oxalates, lactates, malates, tartrates, citrates, benzoates, salicylates, ascorbates, succinates, butyrates, valerates and fumarates. amine salts, such as those of N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris (hydroxymethyl)-aminomethane.

Pharmaceutically acceptable salts can be derived from inorganic or organic acids or can be derived from inorganic or organic bases as is known in the art. Basic amino acids useful for salt formation include arginine, lysine and ornithine. Acidic amino acids useful for salt formation include aspartic acid and glutamic acid. Compound of the invention can be administered in the form of pharmaceutically acceptable esters which include, among others, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids and boronic acids.

Compounds and salts of the invention in the form of pharmaceutical compositions or dosage forms the invention can be administered by any known route that is appropriate for the individual being treated and for the treatment or prophylaxis that is desired. Specifically administration can be orally or non-orally in the form of, for example, granules, powders, tablets, capsules, syrup, suppositories, injections, emulsions, elixir, suspensions or solutions, by mixing these effective components, individually or simultaneously, with pharmaceutically acceptable carriers, excipients, binders, diluents or the like.

A solid formulation for oral administration can comprise one or more of the compounds or salts of the invention alone or in appropriate combination with other active ingredients. Solid formulations can be in the form of powders, granules, tablets, pills and capsules. In these cases, the instant compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, flavoring agent and/or a perfuming agent. Tablets and pills can also be prepared with enteric coating. Standard methods of formulation can be applied to preparation of formulations of the compounds and salts of the invention.

Non-oral administration includes subcutaneous injection, intravenous injection, intramuscular injections, intraperitoneal injection or instillation. Injectable preparations, for example, sterile injectable aqueous suspensions or oil suspensions can be prepared by known methods.

The instant pharmaceutical compositions may be formulated as known in the art for nasal aerosol or inhalation and may be prepared as solutions in saline, and benzyl alcohol or other suitable preservatives, absorption promoters, fluorocarbons, or solubilizing or dispersing agents. Rectal suppositories can be prepared by mixing the drug with a suitable vehicle, for example, cocoa butter and polyethylene glycol, which is in the solid state at ordinary temperatures, in the liquid state at temperatures in intestinal tubes and melts to release the drug. Examples of liquid preparations for oral administration include pharmaceutically acceptable emulsions, syrups, elixirs, suspensions and solutions, which may contain an inactive diluent, for example, pharmaceutically acceptable water.

The pharmaceutical composition can be formulated for topical administration, for example, with a suitable ointment containing one or more of the compounds or salts of the invention suspended or dissolved in a carrier, which include mineral oil, liquid petroleum, white petroleum, propylene glycol, polyoxyethylene polyoxypropylene compound, emulsifying wax and pharmaceutically acceptable water. In addition, topical formulations can be formulated with a lotion or cream containing the active compound suspended or dissolved in a carrier. Suitable carriers include mineral oil, sorbitan monostearate, polysorbate 60, cetyl esters wax, cetearyl alcohol, 2-octyldodecanol, benzyl alcohol and pharmaceutically acceptable water.

As is understood in the art, dosages of the instant compounds are dependent on age, body weight, general health conditions, sex, diet, dose interval, administration routes, excretion rate, combinations of drugs and conditions of the diseases treated. While taking these and other necessary factors into consideration, generally, dosage levels of between about 10 pg per day to about 5000 mg per day, preferably between about 100 mg per day to about 1000 mg per day of the compound are useful in the prevention and treatment of fibrotic diseases or disorders. Typically, the pharmaceutical compositions of this invention will be administered from about 1 to about 5 times per day or alternatively, as a continuous infusion. Such administration can be used as a chronic or acute therapy.

The amount of active ingredient that may be combined with the carrier or excipient materials to produce a single dosage form will vary depending upon the patient/individual treated and the particular mode of administration. A typical preparation will contain from about 5% to about 95% active compound (W/W). Preferably, such preparations contain from about 20% to about 80% active compound. While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs. While taking these and other necessary factors into consideration, for example, a typical preparation will contain from about 0.05% to about 95% active compound (W/W). Preferably, such preparations contain from about 10% to about 80% active compound. The desired unit dose of the composition of this invention is administered once or multiple times daily.

In an embodiment, compounds of the invention include pharmaceutically acceptable salts or solvates thereof of formula X and particularly of formula I, which retain the physiologic activity of the corresponding free base or acid. The salts and free base or acid forms of the compounds of the invention may be different in some physical properties, such as, solubility. See: for example, S. M. Berge, et al., "Pharmaceutical Salts," J. Pharm. Sci., 66: 1-19 (1977), which is incorporated by reference herein for teachings with respect to salts and solvates thereof. The compounds of the present invention or pharmaceutically acceptable salts thereof can form solvates, such as hydrates, or alcoholates. Methods are known in the art for making solvates and particularly hydrates of compounds and salts. Salts of the invention can be in the form of solvates and particularly in the form of hydrates.

In an embodiment, the compounds of any one of Formula I and salts and solvates thereof can be used in manufacture of a medicament for the treatment of fibrotic disorders or disorders including any disorder that is associated with undesirable collage deposition. In an embodiment, the invention provides use of one or more of the compounds of formula I as an antifibrotic agent. The term "solvate" as used herein is a combination, or physical association of a compound with a solvent molecule. A specific solvate is a hydrate. Solvates can include those where the molar ratio of solvent to compound ranges, for example from ½ to 10 or more typically ½ to 4 and can include a disolvate, monosolvate or hemisolvate, among others. This physical association can involve varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. In a specific embodiment, solvates are isolatable with one or more molecules of solvent incorporated into the crystal lattice of a crystalline solid.

Compounds of the invention may be present as solvated forms with a pharmaceutically acceptable solvent, such as water, methanol, ethanol, and the like, and it is intended that the invention includes both solvated and unsolvated forms of compounds of the invention. Solvates typically can function as pharmacological equivalents. Solvates typically do not significantly alter the physiological activity or toxicity of the compounds. Preparation of solvates is known in the art. See, for example, M. Caira et al., J. Pharmaceut. Sci., 93(3):601-611 (2004), E. C. van Tonder et al., AAPS Pharm. Sci. Tech., 5(1): Article 12 (2004), and A. L. Bingham et al., Chem. Commun.: 603-604 (2001). A typical, non-limiting, process of preparing a solvate would involve dissolving a compound of the invention in a desired solvent, which may be water, an organic solvent or a mixture thereof at temperatures above about 20.degree. C., e.g. at room temperature or heating to a temperature above room temperature if appropriate to dissolve the solid, followed by cooling the solution at a rate sufficient to form crystals, and isolating crystals by known methods. Well-known analytical methods, such as infrared spectroscopy, can be used to confirm the presence of the solvent in a crystal of the solvate. More generally, a compound of the invention can be recrystallized from an appropriate solvent (e.g., water) to obtain a solvate (e.g., a hydrate).

Compounds of the invention may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Salts of the invention include "pharmaceutically acceptable salts" which refers to those salts which retain the biological effectiveness and properties of the free bases or free acids, and which are not biologically or otherwise undesirable. Pharmaceutically acceptable salts comprise pharmaceutically-acceptable anions and/or cations.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

With respect to the various compounds of the invention, the atoms therein may have various isotopic forms, e.g., isotopes of hydrogen include deuterium and tritium. All isotopic variants of compounds of the invention are included within the invention and particularly included at deuterium and 13C isotopic variants. It will be appreciated that such isotopic variants may be useful for carrying out various chemical and biological analyses, investigations of reaction mechanisms and the like. Methods for making isotopic variants are known in the art.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately.

When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein. Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

With high potency and selectivity for human CP4H, the bipyDCs represent a class of compounds for the development of antifibrotic or antimetastatic therapeutics. However, these compounds possess a variety of undesirable chemical properties that have limited their development thus far. First, the bipyDCs as a class are not cell permeable, requiring the preparation of suitable cell permeable prodrugs. Second, similar to their parent bipy, the bipyDCs are capable of binding and forming complexes with free iron[38] and likely other biologically relevant metals. The present work initially focused on possible improvements of these compounds. Vasta et al. 2016[58] and the supplemental information for this paper provide additional experimental details including HPLC data, NMR and complex absorbtion spectra, Job's plots and pH titration curves. This reference and the supplemental information are each incorporated by reference herein in its entirety for such details.

To address the cell permeability problem, in silico calculations were performed, which indicated that the diethyl ester analogues of the bipyDCs would have acceptable Log P values (Table 1) for use in cell culture experiments.

TABLE 1

Estimated LogP and Topological Polar Surface Area (TPSA) Values*

| Compound | Est. LogP | TPSA |
|---|---|---|
| Bipy | 1.442 | 25.8 |
| Bipy44'DC | 1.167 | 100.4 |
| Diethyl Bipy44'DC | 2.439 | 78.4 |
| Bipy45'DC | 0.881 | 100.4 |
| Diethyl Bipy45'DC | 2.153 | 78.4 |
| Bipy55'DC | 0.595 | 100.4 |
| Diethyl Bipy55'DC | 1.867 | 78.4 |
| Pypyrid | 0.737 | 38.7 |
| Pypyraz | 0.759 | 38.7 |
| Pyim | 0.897 | 41.6 |
| Pypyr | 0.846 | 41.6 |
| Pythi | 1.642 | 25.8 |
| Pyox | 1.000 | 38.9 |
| PyimDC | 0.285 | 116.2 |
| Diethyl PyimDC | 1.557 | 94.2 |
| PythiDC | 1.029 | 100.4 |
| Diethyl PythiDC | 2.301 | 78.4 |

*Values were estimated using the molecular properties calculator available at http://www.molinspriation.com The extent to which the iron binding properties of these compounds is biologically detrimental was assessed as reported in Vasta et al., 2015[38] A set of bipyDC diethyl esters was prepared and the effect of these compounds on iron metabolism in human cells was investigated factor HIF-1α, all of which give distinct phenotypes depending on the iron status of the cell.[22] In both 231s and HEKs, treatment with bipy and diethyl bipy44'DC (also a known CP4H inhibitor) at 100 µM caused a distinct iron deficient phenotype similar to the deferroxamine (DFO) control. Even in view of their similarity to diethyl bipy44'DC, it was noted that diethyl bipy45'DC and diethyl bipy55'DC did not cause iron deficiency at this moderate concentration. However, the iron-affinity of bipy45'DC and bipy55'DC was found to be only marginally weaker than that of bipy44'DC and the parent bipy. In an attempt to examine these prodrugs at higher concentrations, marked precipitation/crystallization of the compounds was observed above 100 µM (with associated cell death), preventing determination of the concentration at which the iron binding properties of bipy45'DC and bipy55'DC would become problematic. Given the inherent iron binding ability of bipy45'DC and bipy55'DC and the similarity of these compounds to bipy and bipy44'DC, we considered that the iron-binding properties of these compounds would be biologically detrimental. See Vasta et al.[38], which is incorporated by reference herein, for details of the experiments discussed above.

With the above results in mind, we considered that the bipy scaffold itself was problematic and proceeded to assess alternative biheteroaryl scaffolds for potent and selective inhibition of human CP4H, but with improved solubility and iron binding properties. In this effort, one of pyridine rings of bipy was replaced with another 5- or 6-membered aromatic ring containing an alkaloid nitrogen. Specifically, replacement of one pyridine with various 5-membered ring heterocycles was assessed.

Figure 1A:
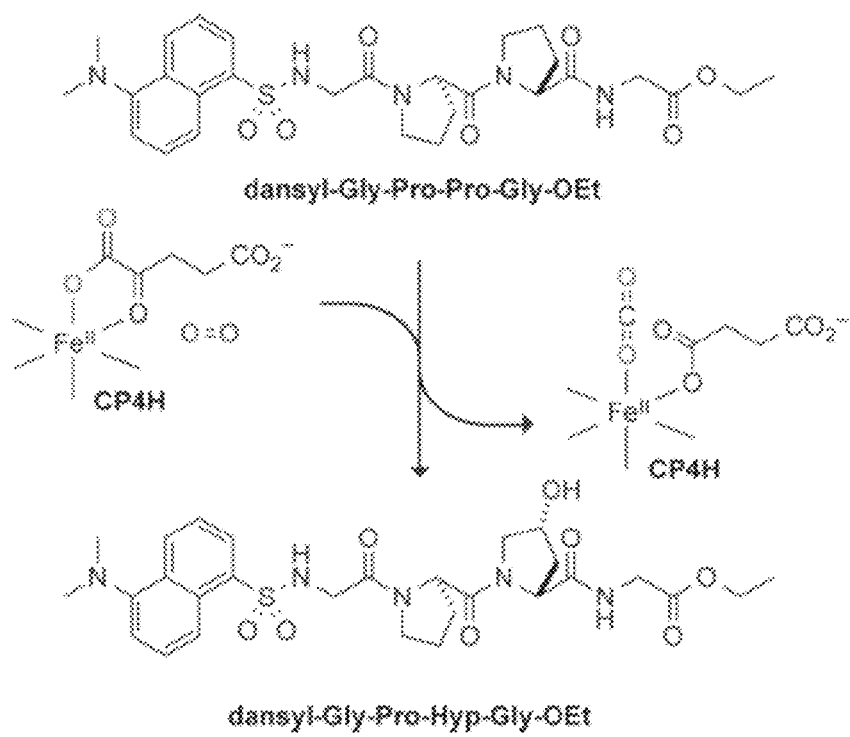
FIG. 1A illustrates the reaction catalyzed by collagen prolyl 4-hydroxylase (CP4H) and its inhibition. In an Fe(II)- and AKG-dependent reaction, CP4Hs catalyze the hydroxylation of Pro residues in collagenous peptides to form Hyp residues.
Figure 1B:
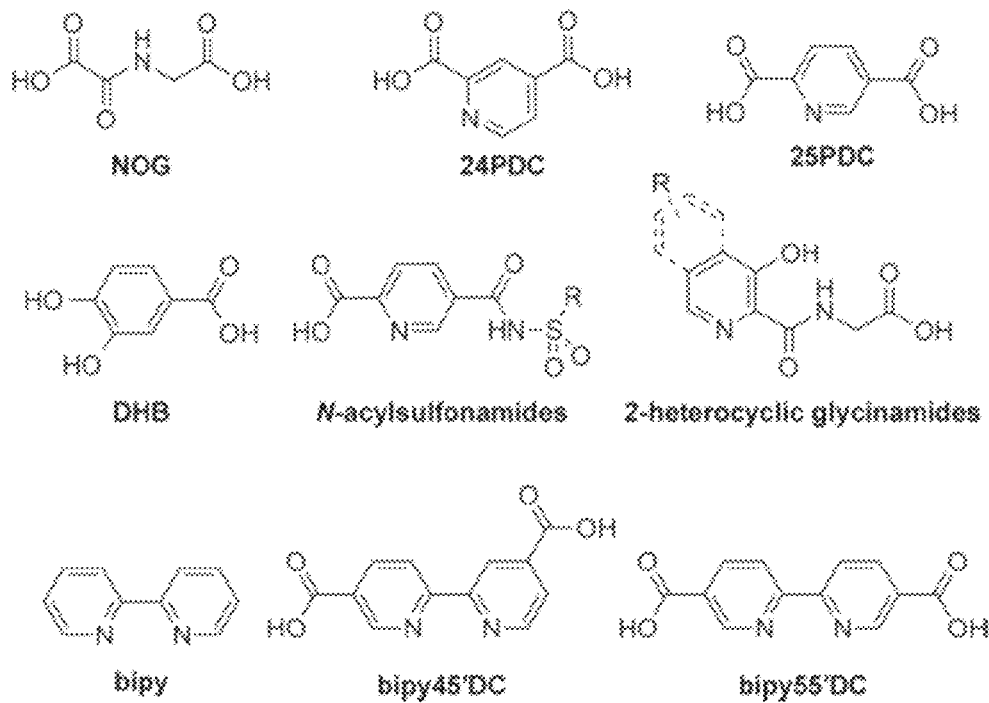
FIG. 1B shows chemical structures of examples of previously reported human CP4H inhibitors.
Figure 2:
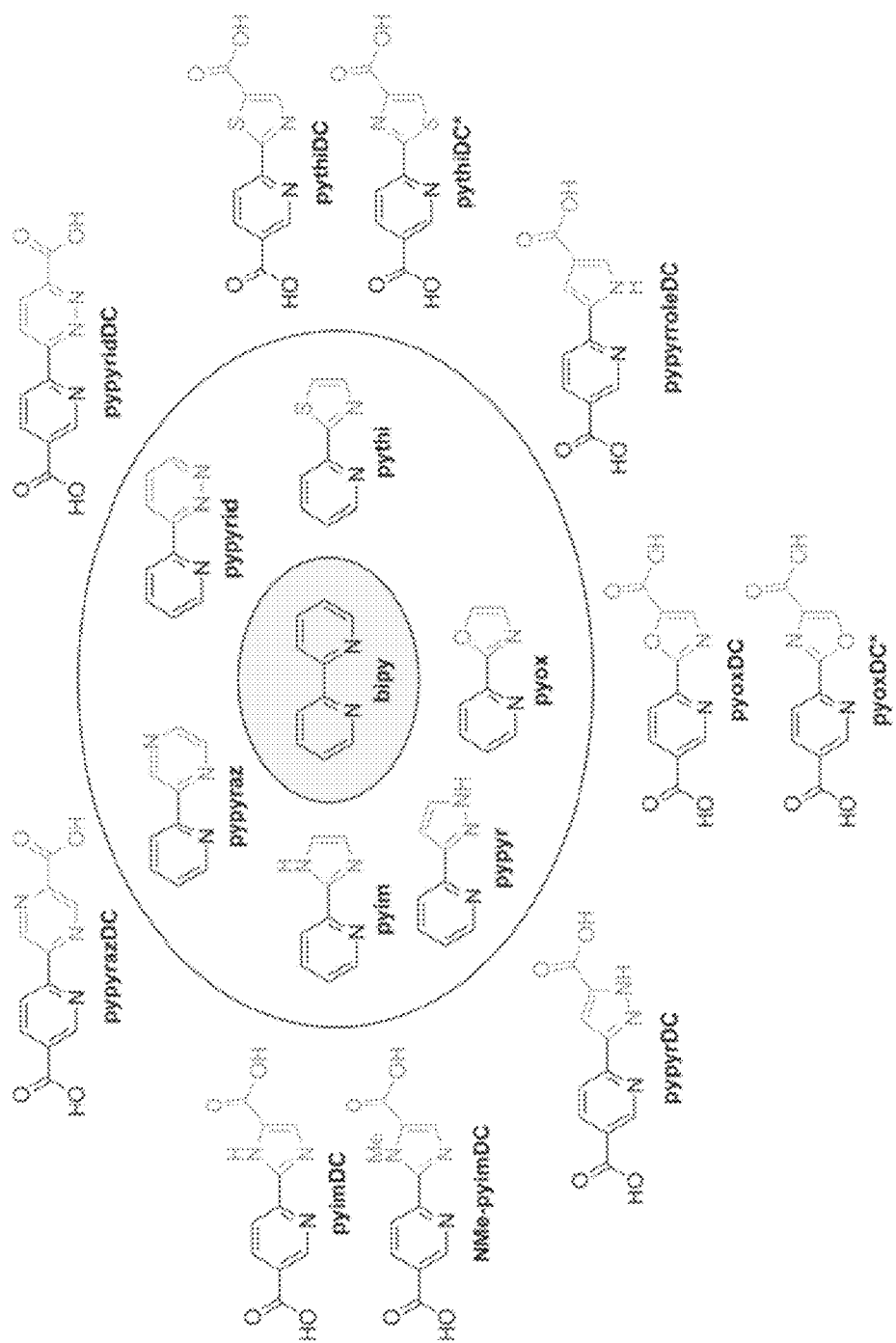
FIG. 2 shows structures of biheteroaryl compounds used in this work.

A library of biheteroaryl compounds (FIG. 2) was prepared and evaluated them as iron chelators in vitro. The library was assembled either from commercial vendors (pypyr and pyim) or by synthesis using palladium-catalyzed cross-coupling reactions (pypyraz, pypyrid, pyox, and pythi). To evaluate the iron affinity of these compounds in vitro, titration experiments were performed to determine the half-maximal concentration required to form a complex with 20 µM Fe(II) at pH 7.0. The ensuing $Fe_{20}$-$EC_{50}$ parameter provides a metric for iron affinity.[25] With the exception of pyox, all members of the library were observed to form distinct colored $Fe(ligand)_3^{2+}$ complexes under these conditions (see the Examples).

Because human CP4Hs are validated therapeutic targets for breast cancer, the MDA-MB-231 breast cancer cell line (231s) was used as a primary model system,[6] with additional analyses in human embryonic kidney cells (HEKs). To probe iron metabolism, immunoblots were performed for ferritin, the transferrin receptor (TfR), and the transcription The $Fe_{20}$-$EC_{50}$ values of the biheteroaryl compounds varied by more than 2 orders of magnitude (FIGS. 3A and 3B; Table 2). All, however, were significantly greater than that of bipy or bipyDCs.[38] The $Fe_{20}$-$EC_{50}$ value appeared to rely on both the ring size and $pK_a$ of the conjugate acid of the alternative heterocycle, as scaffolds with five-membered rings were substantially weaker chelators than were those with six membered rings, and the $pK_a$ value correlated positively with iron affinity.

TABLE 2

Iron Binding by bipy and Biheteroaryl Compounds

| Compound | Heteroaryl $pK_a^a$ (ref.) | $pK_a^b$ | Fe(II) complex $\lambda_{max}^c$ | Stoichiometry (Ligand/Fe)$^d$ | $Fe_{20}$-$EC_{50}^e$ |
|---|---|---|---|---|---|
| bipy | 5.2 (48) | 4.3 | 523 | 3:1 | 43 ± 2 |
| pypyrid | 2.3 (49) | <3 | 522 | 3:1 | 124 ± 1 |
| pypyraz | 0.8 (50) | <3 | 523 | 3:1 | 400 ± 7 |

TABLE 2-continued

Iron Binding by bipy and Biheteroaryl Compounds

| Compound | Heteroaryl $pK_a^a$ (ref.) | $pK_a^b$ | Fe(II) complex $\lambda_{max}^c$ | Stoichiometry (Ligand/Fe)$^d$ | $Fe_{20}$-$EC_{50}^e$ |
|---|---|---|---|---|---|
| pyim | 7.1 (51) | 5.4 | 484 | 3:1 | 900 ± 30 |
| pypyr | 2.5 (52) | 4.1 | 441 | ND$^f$ | 2250 ± 100 |
| pythi | 2.5 (53) | <3 | 524 | 3:1 | 5100 ± 100 |
| pyox | 0.8 (54) | <3 | NO$^g$ | NO$^g$ | >18,000 |

$^a$$pK_a$ value of the conjugate acid of pyridine (bipy) or the nonpyridyl ring.
$^b$$pK_a$ value of the conjugate acid as estimated by titration of the entire compound; bipy, ref 55.
$^c$Determined using spectrophotometry (see The Examples).
$^d$Determined by Job's method.[56,57]
$^e$Determined by titration of 20 µM FeSO4; bipy, ref 38. Values are the mean (±SE) of three replicates.
$^f$Not determined due to prohibitive competing absorbance from iron.
$^g$Not observed.

In view of the observation of the low affinity of the biheteroaryl compounds for free iron, a library of biheteroaryl dicarboxylates (FIG. 2) were prepared and interrogated as both iron chelators and inhibitors of human CP4H. With the exceptions of pyimDC (which was synthesized via a classical route to substituted imidazoles[58]) and pypyrDC (which was synthesized by a 1,3-dipolar cycloaddition of a 2-ethynylpyridine with ethyl diazoacetate[59]), all of the biheteroaryl dicarboxylates were synthesized by either palladium-catalyzed direct arylation of an appropriate heterocycle (pypyrazDC, pypyridDC, pyoxDC, pyoxDC*, pythiDC, or pythiDC*) with a functionalized 2-bromopyridine[24-28] or palladium-catalyzed oxidative crosscoupling (pypyrroleDC) between a functionalized pyridine N-oxide and an N-protected pyrrole.[29] Typically, direct arylation using methyl- or ethyl-protected carboxylate esters allowed synthesis of the target compounds in two to four steps with an acceptable yield. For pyoxDC and pythiDC, cross-coupling yields using the typical inner-sphere base pivalic acid (PivOH) were prohibitively low (<5%, data not shown). The addition of 1-adamantanecarboxylic acid rather than PivOH improved yields markedly (see The Examples).

Iron chelation by the biheteroaryl dicarboxylates was examined in a manner similar to that for the parent scaffolds. Complex formation could not be detected by spectrophotometry for any of the biheteroaryl dicarboxylates at concentrations up to 1 mM, suggesting that the affinity of these compounds for free iron would be negligible in a biological context. Previously, various bipyDCs were reported to have $Fe_{20}$-$EC_{50}$ values that are similar to that of bipy itself.[38] So the finding that biheteroaryl dicarboxylates investigated herein have an $Fe_{20}$-$EC_{50}$ value >1 mM represents an improvement of at least an order of magnitude.

The biheteroaryl dicarboxylates were then assessed as inhibitors of human CP4H1. To separate any inhibitory effect that derives from iron sequestration rather than enzymic binding, previously described assay conditions (10 µM compound and 50 µM FeSO4) in which potent chelators like bipy do not cause inhibition[38] were used. In an initial screen (FIG. 4), some biheteroaryl dicarboxylates showed little or no inhibition of human CP4H1, consistent with the inability of their heteroatoms to participate in an enzymic interaction. (Both pypyridDC and pypyrDC even showed modest activation under these conditions.) However, pyimDC, pyoxDC, and pythiDC were found to be inhibitors of human CP4H1, with pyimDC and pythiDC demonstrating potency only a bit weaker than that of the bipyDCs.

In contrast, regioisomers pythiDC* and pyoxDC* did not show significant inhibition, suggesting that proper regiochemistry is important for inhibition.

Unlike oxazole or thiazole, imidazole exists as two tautomers, one with a proton on N1 (as in the depiction of pyimDC in FIG. 2) and another with a proton on N3. Although complex formation was not observe between pyimDC and free iron by spectrophotometry, it was found that pyimDC was able to deter the formation of the Fe(bipy)$_3^{2+}$ complex in a dose-dependent manner (FIG. 5A and the Table in FIG. 5B). Moreover, competition required a free carboxylate on the imidazole ring. These data are consistent with the formation of a Fe(pyimDC)$_2$ complex with N1 bound to iron.

To eliminate this mode of binding, NMe-pyimDC (FIG. 2), that is methylated on N1. NMe-pyimDC was also able to deter the formation of the Fe(bipy)$_3^{2+}$ complex, but only at high concentrations (Table in FIG. 5B). NMe-pyimDC was found to be an inhibitor of human CP4H in vitro, but that its potency is less than that of pyimDC (FIG. 4). In subsequent dose-response experiments, the inhibition curves for pyimDC, pythiDC, and pyoxDC were found to be sigmoidal, yielding IC$_{50}$ values in the low-micromolar range (FIG. 6A). The potencies of pyimDC and pythiDC were approximately 10-fold greater than that of pyoxDC. A Lineweaver-Burke analysis of inhibition of CP4H by pythiDC demonstrated competitive inhibition with respect to the AKG cosubstrate (FIG. 6B).

Like bipy45'DC and bipy55'DC,[21,38] pyimDC, pyoxDC, and pythiDC could bind in the AKG binding pocket and use their second carboxyl group to form additional interactions with residues in the active site of CP4H. If so, then the biheteroaryl dicarboxylates should exhibit structure-activity relationships similar to those of bipy45'DC and bipy55'DC for the inhibition of PHD2, another P4H enzyme that has been characterized extensively. PyimDC, pythiDC, and pyoxDC inhibit human PHD2 only weakly (FIG. 7), with pythiDC displaying especially low potency.

Next pyimDC and pythiDC were assessed for use in cellulo. First, the effect of these compounds on iron metabolism in human cells was determined. Because human CP4Hs are validated therapeutic targets for breast cancer, the MDA-MB-231 human breast cancer cell line as a primary model system.[6]

Additional analyses were performed in human embryonic kidney. (HEK) cells. Iron metabolism was assessed with immunoblots for ferritin, the transferrin receptor (TFR), and the transcription factor HIF-1α, all of which are known to give distinct phenotypes depending on the status of iron in a human cell.[22]

More specifically, levels of ferritin and TFR are regulated by iron regulatory proteins 1 and 2 (IRPs), which have irondependent RNA-binding activity that modulates the expression of target genes at the level of mRNA translation or stability.[44, 45]

The stability of HIF-1α is dependent on the prolyl 4-hydroxylase activity of PHD2, which is an activity that is inherently sensitive to the iron status of the cell. Thus, iron-deficient cells exhibit ferritin levels that are lower and TFR and HIF-1α levels that are higher than those of untreated cells.

The esterification of carboxyl groups is a common strategy to generate effective prodrugs.[46,47] Ethyl dihydroxybenzoate (EDHB), an AKG mimic that is commonly used as a "P4H" inhibitor in cell culture models, served as our benchmark.[22,31] Calculations suggested that the diethyl esters of pyimDC and pythiDC would have log P values conducive to cellular uptake (Table 1). Moreover, the iron affinity of these diethyl esters remained sufficiently low (FIGS. 3A and 3B). Cultured MDAMB-231 cells are known to secrete large amounts of collagen.[6] Due to the importance of CP4H-dependent hydroxylation for collagen stability, the level of collagen secreted by MDA-MB-231 cells is dependent on the activity of this enzyme. Thus, MDA-MB-231 cells are ideal for investigations of both iron deficiency and CP4H activity.

Toward this end, MDA-MB-231 cells were treated with biheteroaryl dicarboxylates and assayed for cytotoxicity and indicators of iron deficiency. None of the esterified biheteroaryl dicarboxylates exhibited cytotoxic activity at high micromolar concentrations (The Examples). Cells treated with EDHB demonstrated a strong iron-deficient phenotype, as expected (FIGS. 8A and 8B). In contrast, cells treated with diethyl pythiDC appeared to be normal at concentrations as high as 500 µM. Interestingly, diethyl pyimDC showed an intermediate phenotype characterized by a significant decrease in ferritin levels but without an associated accumulation of TFR or HIF-1α. This phenotype was, however, not observable at diethyl pyimDC concentrations ≤56 µM. The results in MDA-MB-231 cells were replicated in HEK cells. Again, treatment with diethyl pythiDC and low levels of diethyl pyimDC (as well as simply pyim and pythi; FIGS. 9A and 9B) did not affect the level of TFR, HIF-1α, or ferritin (FIG. 10).

Next, the function of IRPs in cells treated with the esterified biheteroaryl compounds was assessed. Using a radiolabeled RNA ligand, electrophoretic mobility shift assays were performed on IRPs from treated MDA-MB-231 cells. Whereas DFO, EDHB, and bipy all caused significant increases in RNA binding by IRPs, diethyl pyimDC and diethyl pythiDC did not (FIG. 11). This result is again consistent with these compounds having little effect on cellular iron levels.

The effect of treating MDA-MB-231 cells with the esterified biheteroaryl compounds on the cellular secretion of type I collagen (FIG. 8C) was examined. Secretion of type I collagen relies on CP4H activity.[6] Treatment with either diethyl pyimDC or diethyl pythiDC reduced the level of secreted collagen significantly (FIG. 8C). Moreover, the efficacy of diethyl pyimDC or diethyl pythiDC was indistinguishable from that of diethyl bipy55'DC. No inhibition of catalysis by CP4H1 or PHD2 was observed in vitro with these diethyl esters at a concentration of 100 µM (data not shown), confirming that the inhibitory potential of these compounds is masked by esterification. Lastly, treatment with diethyl pyimDC and diethyl pythiDC did not appear to affect the levels of human CP4H1 itself (FIG. 12), consistent with the observed reduction in collagen secretion arising from inhibition of CP4H.

Detailed Experimental

I. General 2,4-Pyridinedicarboxylic acid (24PDC), 2,5-pyridinedicarboxylic acid (25PDC), 2,2'-bipyridine (bipy), 2-(1H-Imidazol-2-yl)pyridine (pyim), and 2,2'-bipyridine-5,5'-dicarboxylic acid (bipy55'DC) were obtained from Sigma-Aldrich (St. Louis, Mo.). 2,2'-bipyridine-4,4'-dicarboxylic acid (bipy44'DC) was obtained from TCI America (Portland, Oreg.). 2-(1H-pyrazol-3-yl)pyridine was from Combi-Blocks (San Diego, Calif.). Phosphine ligands and phosphonium salts were obtained from either Sigma-Aldrich or Strem (Newberryport, Mass.), stored in a dessicator, and used without further purification. Pd(OAc)$_2$ was obtained from Sigma-Aldrich, stored in a dessicator, and used without further purification. Deferroxamine mesylate was obtained from Santa Cruz Biotechnology (Dallas, Tex.). Ethyl dihydroxybenzoate (EDHB) was obtained from Combi-Blocks (San Diego, Calif.) and recrystallized from EtOAc before use in cell culture experiments. All other reagent chemicals were obtained from commercial sources (Sigma-Aldrich, Acros, Combi-Blocks, Oakwood Products, Enamine, Bachem, or Novabiochem) and used without further purification. The HIF-1α peptide$_{556-575}$ was from AnaSpec (Fremont, Calif.) and used without further purification. All glassware was flame- or oven-dried, and reactions were performed under N$_2$(g) unless indicated otherwise. DCM and toluene were dried over a column of alumina. Dimethylformamide was dried over alumina and further purified through an isocyanate scrubbing column. Other anhydrous solvents were obtained in septum-sealed bottles. Flash chromatography was performed with columns of 40-63 Å silica gel, 230-400 mesh (Silicycle, Québec City, Canada). Thin-layer chromatography (TLC) was performed on plates of EMD 250 µm silica 60-F$_{254}$ with visualization by UV light or staining with KMnO$_4$. The phrase "concentrated under reduced pressure" refers to the removal of solvents and other volatile materials using a rotary evaporator at water aspirator pressure (<20 torr) while maintaining water-bath temperature below 40° C. Residual solvent was removed from samples at high vacuum (<0.1 torr). The term "high vacuum" refers to vacuum achieved by a mechanical belt-drive oil pump. All reported yields are unoptimized. All procedures were performed at ambient temperature unless indicated otherwise.

II. Instrumentation

NMR spectra were acquired at ambient temperature with a Bruker DMX-400 Avance spectrometer or a Avance 500i spectrometer from Brucker (Billerica, Mass.) at the National Magnetic Resonance Facility at Madison (NMRFAM) and were referenced to TMS or a residual protic solvent. Some compounds exist as either mixtures of rotomers or tautomers that do not interconvert on the NMR timescale at ambient temperature and therefore exhibit multiple sets of NMR signals. Electrospray ionization (ESI) and electron ionization (EI) mass spectrometry were performed with a Micromass LCT® or Micromass AutoSpec® instruments, respectively, from Waters (Milford, Mass.) at the Mass Spectrometry Facility in the Department of Chemistry at the University of Wisconsin-Madison. The progress of reactions catalyzed by prolyl 4-hydroxylases was determined by analytical HPLC (Waters system equipped with a Waters 996 photodiode array detector, Empower 2 software). Preparative HPLC was performed using a Prominence HPLC instrument from Shimadzu (Kyoto, Japan) equipped with two LC-20AP pumps, a SPD-M20A photodiode array detector, and a CTO-20A column oven. Iron complexes with biheteroaryl ligands were analyzed by spectrophotometry using a Cary 60 UV-Vis Spectrometer from Agilent Technologies (Santa Clara, Calif.) Protein concentrations were calculated from their absorbance at 280 nm as measured with a NanoVue Plus spectrophotometer from GE Healthcare using an extinction coefficient[35] of 290,000 M$^{-1}$cm$^{-1}$ for human CP4H[1] and 36,9000 M$^{-1}$cm$^{-1}$ for human PHD2.[36] IC$_{50}$-, EC$_{50}$-, and LD$_{50}$-values were calculated from experimental data with Prism version 6.0 from GraphPad Software (La Jolla, Calif.).

III. Production of Recombinant Human CP4H1

Human CP4H containing the α(I) isoform was produced heterologously in Origami B(DE3) *Escherichia coli* cells and purified as described previously.[35]

IV. Assay of Human CP4H1 Activity in the Presence of Inhibitors

The catalytic activity of human CP4H1 was assayed as described previously.[35] Briefly, activity assays were carried out at 30° C. in 100 µL Tris-HCl buffer, pH 7.8, containing human CP4H1 (100 nM), inhibitor (0-500 µM), substrate (dansylGlyProProGlyOEt, 500 µM), FeSO$_4$ (50 µM), BSA (1 mg/mL), catalase (0.1 mg/mL), sodium ascorbate (2 mM), DTT (100 µM), and α-ketoglutarate (100 µM). Reactions were pre-incubated with or without inhibitor for 2 min at 30° C., after which the reaction was initiated by the addition of α-ketoglutarate. After 15 min, reactions were quenched by boiling for 45 s and centrifuged at 10,000 g. The supernatant (20-50 µL) was injected into a Nucleodur® C18 Gravity reversed-phase column (4.6×250 mm, 5 µm particle size) from Macherey-Nagel (Bethlehem, Pa.). The column was eluted at 1 mL/min with a gradient (20 min) of aqueous acetonitrile (20-45% v/v) containing 0.1% v/v TFA. The absorbance of the eluent was monitored at 289 nm. All assays were performed in triplicate. Data are reported as activity relative to control reactions lacking inhibitor, where catalytic activity is determined from the percent conversion of substrate to product. Dose-response curves were generated for each inhibitor by plotting the relative activity versus the log of the inhibitor concentration. IC$_{50}$-values for each inhibitor were interpolated from the data by non-linear regression using the sigmoidal dose-response function available in Prism.

V. Production of Recombinant Human PHD2

A cDNA encoding human PHD2$_{181-426}$ possessing an N-terminal hexahistidine (His$_6$) tag (NHis$_6$-PHD2$_{181-426}$) was cloned using the Gibson strategy[37] and the encoded protein was produced and purified as described previously.[36]

VI. Assay of Human PHD2 Activity in the Presence of Inhibitors

The catalytic activity of human PHD2 was assayed as described previously.[36] Briefly, activity assays were carried out at 30° C. in 100 µL Tris-HCl buffer, pH 7.8, containing human NHis$_6$-PHD2$_{181-426}$ (5 µM), inhibitor (0-50 µM), substrate (HIF-1α peptide$_{556-574}$, 50 µM), FeSO$_4$ (50 µM), BSA (1 mg/mL), catalase (0.3 mg/mL), sodium ascorbate (2 mM), DTT (1 mM), and α-ketoglutarate (35 µM). Reactions mixtures were pre-incubated with or without inhibitor for 2 min at 30° C., after which the reaction was initiated by the addition of α-ketoglutarate. After 10 minutes, reactions were quenched by boiling for 60 s and centrifuged at 10,000 g. The supernatant (50 µL) was injected into a Nucleodur® C18 Gravity reversed-phase column (4.6×250 mm, 5 µm particle size) from Macherey-Nagel (Bethlehem, Pa.). The column was eluted at 1 mL/min with a gradient (34 min) of 5-56% aqueous acetonitrile containing 0.1% v/v TFA. The absorbance of the eluent was monitored at 218 nm. All assays were performed in triplicate. Data is reported as activity relative to control reactions lacking inhibitor, where activity is determined from the percent conversion of substrate to product.

VII. Estimate of the pKa Values of Biheteroaryl Ligands

The pKa value of biheteroaryl compounds was estimated with potentiometric titration. Compounds (5-10 mM) were dissolved in water and the pH was adjusted to ~12 by adding 10 M NaOH. The pH of the solution was recorded with an Accumet™ XL500 pH meter equipped with an Orion 912600® pH electrode from Thermo Fisher Scientific while titrating the solution with HCl (1 M or 100 µM, as necessary) until a pH value of ~1.75 was achieved. Titration curves were prepared by plotting the solution pH versus the volume of 1 M HCl added, and pKa values were estimated from derivative plots of the titration curves using Prism software.

VIII. Assay of Fe(II)-Affinity for Biheteroaryl Ligands

The affinity of biheteroaryl ligands for Fe(II) was determined comparatively by measuring the half-maximal concentration ($EC_{50}$) required for binding 20 µM Fe(II) ($Fe_{20}$-$EC_{50}$) in sodium phosphate buffer at pH 7. Stock solutions of ligands were prepared in either water for high affinity ligands (typically $Fe_{20}$-$EC_{50}$<1 mM) or DMSO for low affinity ligands (typically $Fe_{20}$-$EC_{50}$>1000 µM). Stock solutions of $FeSO_4$ were prepared in $H_2O$ and used within 3 hours of preparation. Ligand solutions (3-18000 µM depending on affinity) were prepared in 10 mM sodium phosphate buffer, pH 7, after which Fe(II) stock solution was added to initiate complex formation. For high affinity ligands, solutions were allowed to equilibrate for 15 min, after which the absorbance was recorded at the $\lambda_{max}$ for the complex under study. For most low affinity ligands, the corresponding Fe(II) complexes were unstable and observed to dissociate over time. Therefore, the absorbance value was determined within 30 s of mixing, where the absorbance was measured at the $\lambda_{max}$ for the complex under study. Complexes with pyox were not observed under these conditions. Absorbance values were corrected by subtracting the absorbance value in the absence of ligand. Dose-response curves were generated for each ligand by plotting the absorbance versus the log of the ligand concentration. $Fe_{20}$-$EC_{50}$ values for each ligand were interpolated from the dose-response curves by non-linear regression using the sigmoidal dose-response function in Prism. All experiments were performed in triplicate. Experiments to study pyimDC were performed as described above, except that phosphate buffer was excluded from the assay solution, bipy was added last to a final concentration of 300 µM, and the absorbance of the $Fe(bipy)_3^{2+}$ complex was measured at 523 nm.

IX. Determination of Fe(II) Complex Stoichiometry

The stoichiometry of biheteroaryl complexes with Fe(II) was estimated via Job's method. Briefly, reactions were prepared such that the total moles of Fe(II) and ligand was kept constant, but the mole fraction of the ligand was varied from 0 to 1. The total concentration of ligand and Fe(II) used for each individual ligand was based upon the iron affinity and extinction coefficient, and ranged from 0.4 mM to 2 mM. Stock solutions of ligands were prepared in water. Stock solutions of $FeSO_4$ were prepared in water and used within 3 hours of preparation. Reactions were prepared in 10 mM sodium phosphate buffer, pH 7.0, and complex formation was initiated by the addition of Fe(II) solution. For high affinity ligands (typically $Fe_{20}$-$EC_{50}$<1 mM), solutions were allowed to equilibrate for 15 min, after which the absorbance was recorded at the $\lambda_{max}$ for the complex under study. For most low affinity ligands (typically $Fe_{20}$-$EC_{50}$>1 mM), the corresponding Fe(II) complexes were unstable and observed to dissociate over time. Therefore, the absorbance value was determined within 30 s of mixing, where the absorbance was measured at the $\lambda_{max}$ for the complex under study. Complexes with pyox were not observed under these conditions. Absorbance values were corrected by subtracting the absorbance value of a blank solution in absence of $FeSO_4$, after which the values were normalized relative to the reaction with the highest absorbance value. All experiments were performed in at least duplicate. Job's plots were constructed by plotting the normalized absorbance versus the mole fraction of biheteroaryl ligand, after which the stoichiometry of the complex was estimated from the mole fraction of the reaction with the highest absorbance value. If necessary, blank titrations using only Fe(II) were used to correct the Job's plots.

X. General Mammalian Cell Culture

The HEK293T cell line was obtained from American Type Culture Collection (ATCC, Manassas, Va.), and the MDA-MB-231 cell line was a generous gift from Dr. Beth Weaver. Cell lines were maintained according to the procedures recommended by the ATCC. Cells were grown in a cell culture incubator at 37° C. under $CO_2$ (5% v/v) in flat-bottomed culture flasks. The culture medium was DMEM supplemented with GIBCO fetal bovine serum (FBS) (10% v/v), penicillin (100 units/mL), streptomycin (100 µg/mL) and L-glutamine (2 mM). Cells were counted by hemocytometry with Trypan Blue prior to use in assays.

XI. Cytotoxicity Assays

The toxicity of esterified biheteroaryl compounds for human breast cancer cells was evaluated with the CellTiter 96® AQueous One Solution Cell Proliferation Assay (MTS) from Promega (Madison, Wis.). Briefly, MDA-MB-231 cells grown as described in Section X were plated at a concentration of 5,000 cells/well in a clear 96-well plate. The cells were allowed to adhere for 4 h, after which the medium was removed and discarded. Fresh medium was added and the cells were treated with varying concentrations of the test compound at 37° C. for 24 h. The medium was removed, and cells were washed with Dulbecco's PBS. The MTS reagent was added at a ratio of 1:5, and the cells were incubated at 37° C. for 2 h before measuring the absorbance at 490 nm. The average absorbance was measured in triplicate for each concentration tested, and the entire experiment was repeated in duplicate. The percentage of viable cells was determined by normalizing to a PBS control (100% viable), and a $H_2O_2$ control (0% viable). For all of the compounds tested, the $LD_{50}$-value could not be measured due to its being higher than the aqueous solubility limit: diethyl bipy55'DC, $LD_{50}$>100 µM; diethyl pyimDC, $LD_{50}$>1000 µM; diethyl pythiDC, $LD_{50}$>500 µM.

XII. Effect of CP4H Inhibitors on Iron Metabolism and P4HA1 Levels in Human Cells MDA-MB-231 or HEK293T cells were plated at 50,000 cells/well into 12-well plates and grown to confluence (~24 h) as described in Section X. The cells were washed, and the medium was replaced with 1.0 mL of serum-free medium. Stock solutions of all test compounds were prepared at 100× in DMSO and added to a final concentration of 1× (0.1-0.5 mM). After addition of the test compound or DMSO vehicle, cells were incubated for 24 h. The cells were then washed with 100 μL MPER solution from Thermo Fisher Scientific (Waltham, Mass.) and collected. Protein concentrations were determined by BCA assay (Thermo Fisher Scientific), and samples corresponding to 40 μg total protein were analyzed by immunoblot.

XIII. Immunoblotting

For all immunoblot analyses, protein samples where boiled in SDS-PAGE buffer, separated by electrophoresis through a Tris-glycine SDS-PAGE gel from Bio-Rad Laboratories (Hercules, Calif.), and subsequently transferred to a PVDF membrane for immunoblotting. All primary antibodies were used at the working dilution specified by the manufacturer. Primary antibodies were visualized using a complementary secondary antibody fused to horseradish peroxidase (HRP), with detection of HRP by chemiluminescence, imaging using an ImageQuant LAS 4000 (GE Healthcare), and quantification by densitometry (ImageJ software). The anti-rabbit antibody from Promega and the anti-mouse antibody from Abbiotec (San Diego, Calif.) were used at the working dilution specified by the manufacturer. Statistical comparisons were performed using Student's t-test or one-way ANOVA functions available in Prism.

For investigations of iron metabolism, protein samples (40 μg) were separated by SDS-PAGE through a 12% w/v acrylamide gel, and blots were probed with primary antibodies to human ferritin (rabbit monoclonal) from Abcam (Cambridge, Mass.), human transferrin receptor (mouse monoclonal) from Invitrogen, human HIF-1α (mouse monoclonal) from BD Biosciences, and human β-actin (rabbit monoclonal) from Cell Signaling Technology (Danvers, Mass.). Quantifications were normalized to the signal from β-actin, after which treated samples were compared to vehicle-treated controls.

For investigations of P4HA1 levels, protein samples were treated and quantified as described above for iron metabolism except that the blots were probed with primary antibodies to human P4HA1 (rabbit polyclonal) from Thermo Fisher Scientific and human β-actin.

For investigations of collagen secretion, protein samples were separated by SDS-PAGE through a 7.5% w/v acrylamide gel. Blots were first stained for total protein using Ponceau S, after which they were probed with a primary antibody to human type-I collagen (α1) (rabbit polyclonal) from Novus Biologicals (Littleton, Colo.). Quantifications were normalized to the total protein signal obtained from Ponceau S staining, after which treated samples were compared to vehicle-treated controls.

XIV. Effect of CP4H Inhibitors on the Binding of the Iron-Responsive Element by IRPs MDA-MB-231 cells were plated at $3 \times 10^6$ cells/dish into 100 mm×20 mm dishes and grown to confluence (~24 h) as described in Section X. The cells were washed, and the medium was replaced with 10 mL of serum-free medium. Stock solutions of all test compounds were prepared at 100× in DMSO and added to a final concentration of 1× (as denoted). After addition of the test compound or DMSO vehicle, cells were incubated for 24 h, after which they were harvested by trypsinization and centrifugation. The resultant pellets (~50 μL) were washed with PBS and then lysed using a protocol described previously.[41] Briefly, cell pellets were resuspended in 200 μL of cell lysis buffer, which was 20 mM Hepes-HCl buffer, pH 7.4, containing sodium pyrophosphate (10 mM), sodium fluoride (50 mM), β-glycerophosphate (50 mM), EDTA (5 mM), GTP (1 mM), sodium orthovanadate (1 mM), benzamidine hydrochloride (2 mM), Nonidet NP-40 (0.5% v/v), p-nitrophenyl p'-guanidinobenzoate-HCl (25 μg/mL), DTT (1 mM), leupeptin (40 μg/mL), pepstatin (4 μg/mL), SBTI (100 μg/mL), MG132 (10 μM), PMSF (200 μM), and BHT (5 μg/mL) by vortexing and lysed on ice by vortexing every few min. After 15 min, the lysates were centrifuged at 14,000 rpm and the supernatants aliquoted and stored at −80° C. until analysis by an electrophoretic mobility shift assay (EMSA).

XV. Electrophoretic Mobility Shift Assay for IRE-Binding by IRPs

EMSAs were performed and quantified essentially as described previously.[42] Briefly [$^{32}$P]-L-ferritin IRE (1 nM RNA, specific radioactivity ~7,000 dpm/fmol) was incubated with lysate protein (2.5 μg as determined by the Bradford assay) in binding buffer for 10 min on ice. Heparin was added (to 0.5 mg/mL), and the reaction mixture was incubated for an additional 5 min on ice before separating bound and free RNA on a nondenaturing polyacrylamide gel at ambient temperature.

XVI. Effect of CP4H Inhibitors on Collagen Production in Mammalian Cells

MDA-MB-231 cells were plated at 50,000 cells/well into 12-well plates and grown to confluence (~24 h) as described in Section X. The cells were washed, and the medium was replaced with 1.5 mL of serum-free medium containing sodium ascorbate (50 μg/mL). Stock solutions of all test compounds were prepared at 100× in DMSO and added to a final concentration of 1× (as denoted). After the addition of a test compound or vehicle (DMSO), cells were incubated for 48 h, after which 1.0 mL of conditioned medium was removed and added to 4.0 mL of chilled acetone (−20° C.). The resultant mixtures were incubated for 3 h at −20° C., after which the precipitated protein was pelleted by centrifugation at 10,000 g for 30 min. The supernatants were discarded and the pellets dried briefly in a fume hood. Pellets were stored at −20° C. prior to analysis with an immunoblot.

XVII. Synthetic Procedures

3-Methoxycarbonylpyridine N-oxide

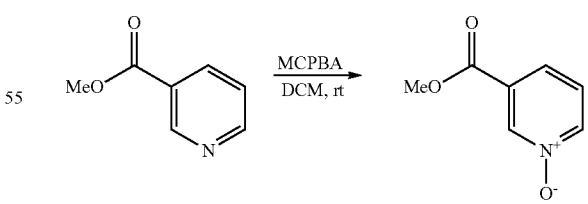

Procedure:
Methyl nicotinate (2.0 g, 14.6 mmoles) and m-chloroperoxybenzoic acid (6.5 g, 29.2 mmoles) were dissolved in dry dichloromethane (150 mL) in a flame-dried flask. The reaction was stirred at room temperature for 24 h. The solvent was evaporated under reduced pressure, and the resulting residue was purified by chromatography on silica (5-20% MeOH in acetone) to afford the title compound as a pale yellow solid (2.19 g, 98%). ¹H NMR (400 MHz, CDCl₃) δ 8.77 (s, 1H), 8.34 (d, J=6.8 Hz, 1H), 7.86 (d, J=8.0 Hz, 1H), 7.38 (dd, J=6.8, 8.0 Hz, 1H), 3.98 (s, 3H); ¹³C NMR (100 MHz, CDCl₃) δ 163.2, 142.5, 140.3, 129.9, 126.2, 125.8, 53.1; HRMS (ESI) m/z 154.0494 [calc'd for C₇H₈NO₃ (M+H)⁺ 154.0499].

Methyl pyrazine-3-carboxylate-1-oxide

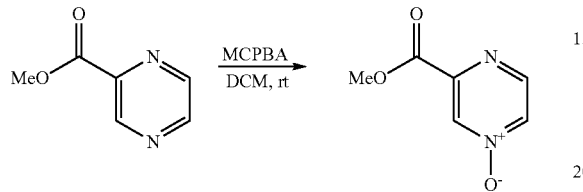

Procedure:

Methyl pyrazine-2-carboxylate (3.0 g, 21.7 mmoles) and m-chloroperoxybenzoic acid (7.3 g, 32.6 mmoles) were dissolved in dry DCM (43 mL) in a flame-dried flask. The reaction was stirred at room temperature for 48 h. The solvent was evaporated under reduced pressure, and the resulting residue was purified by chromatography on silica (40-50% acetone in hexanes followed by 80-100% EtOAc in hexanes) to afford the title compound as a white solid (751 mg, 22%). ¹H NMR (400 MHz, CDCl₃) δ8.76 (dd, J=0.8, 1.6 Hz, 1H), 8.57 (dd, J=0.4, 4.0 Hz, 1H), 8.22 (dd, J=2.0, 4.0 Hz, 1H), 4.05 (s, 3H); ¹³C NMR (100 MHz, CDCl₃) δ 162.6, 147.6, 147.3, 136.0, 135.9, 53.7; HRMS (ESI) m/z 155.0451 [calc'd for C₆H₇N₂O₃ (M+H)⁺ 155.0452].

Methyl pyridazine-3-carboxylate-1-oxide

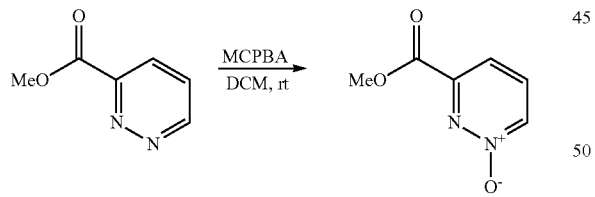

Procedure:

Methyl pyridazine-3-carboxylate (2.0 g, 14.5 mmoles) and m-chloroperoxybenzoic acid (3.9 g, 17.4 mmoles) were dissolved in dry DCM (29 mL) in a flame-dried flask. The reaction was stirred at room temperature for 5 h. The solvent was evaporated under reduced pressure, and the resulting residue was purified by chromatography on silica (30% acetone in hexanes) to afford the title compound as an off-white solid (1.97 g, 88%). ¹H NMR (400 MHz, CDCl₃) δ8.28 (dd, J=2.4, 5.2 Hz, 1H), 7.79-7.75 (m, 2H), 4.03 (s, 3H); ¹³C NMR (100 MHz, CDCl₃) δ162.2, 150.2, 136.9, 134.4, 116.8, 53.6; HRMS (ESI) m/z 155.0452 [calc'd for C₆H₇N₂O₃ (M+H)⁺ 155.0452].

Methyl 1-pivaloyloxymethyl-1H-pyrrole-3-carboxylate

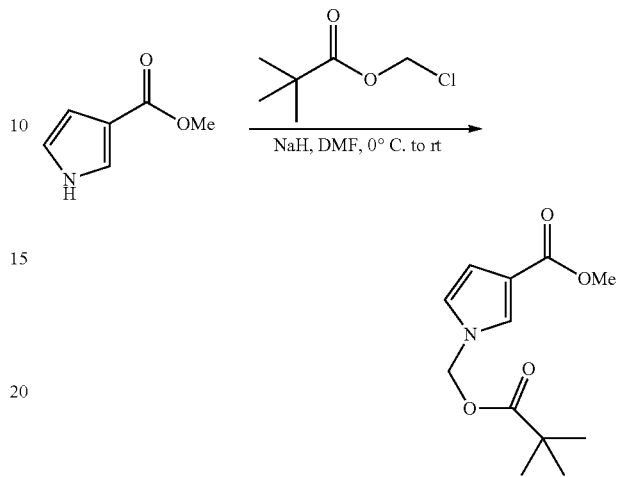

Procedure:

NaH (60% w/v in mineral oil, 267 mg, 6.7 mmoles) was added to a dry flask. The flask was evacuated and purged with nitrogen (~5 times). Dry DMF (3 mL) was added and the flask was cooled on ice. A degassed solution of methyl 1H-pyrrole-3-carboxylate (836 mg, 6.7 mmoles) in dry DMF (4 mL) was added dropwise over 5 min with stirring. The reaction was stirred on ice for 45 min until gas evolution was complete, after which chloromethyl pivalate (0.97 mL, 6.7 mmoles) was added dropwise. The reaction was allowed to come to room temperature overnight, after which the reaction was concentrated under reduced pressure to a crude oil. The oil was taken up in H₂O (25 mL) and the aqueous layer extracted with DCM (5×25 mL). The combined organics were dried over Na₂SO₄(s) and concentrated under reduced pressure, after which the crude product was purified by chromatography on silica (25% EtOAc in hexanes) to afford the title compound (1.20 g, 75%) as a golden oil.

¹H NMR (400 MHz, CDCl₃) δ7.46 (dd, J=0.4, 2.0 Hz, 1H), 6.79 (dd, J=0.4, 2.4 Hz, 1H), 6.60 (dd, J=1.2, 1.6 Hz, 1H), 5.79 (s, 2H), 3.81, (s, 3H), 1.18 (s, 9H); ¹³C NMR (100 MHz, CDCl₃) δ177.7, 164.9, 126.9, 122.6, 117.4, 111.0, 70.8, 51.2, 38.8, 26.8; HRMS (ESI) m/z 240.1233 [calc'd for C₁₂H₁₈NO₄ (M+H)⁺ 240.1231].

Ethyl 2-(2-trimethylsilylethynyl)pyridine-5-carboxylate

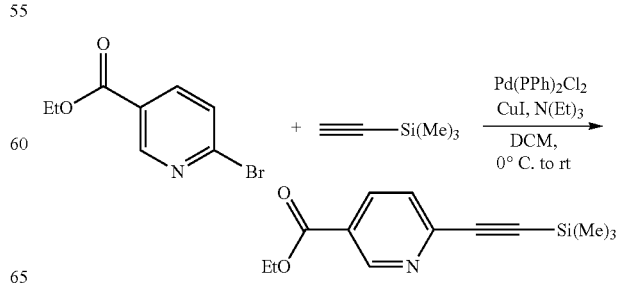

Procedure:

Pd(PPh)$_2$Cl$_2$ (21 mg, 0.030 mmoles), CuI (142 mg, 0.089 mmoles), and ethyl 2-bromonicotinate (532 mg, 2.3 mmoles) were added to a dried flask on ice. The flask was evacuated and purged with nitrogen (~5 times). A degassed solution of trimethylsilylacetylene (420 μL, 3.0 mmoles) in DCM (5 mL) was added to the flask while stirring on ice. Triethylamine (1.4 mL, 10.0 mmoles) was added the flask while stirring, after which the flask was allowed to come to room temperature overnight. The reaction mixture was diluted with hexanes (5 mL) and filtered through Celite®, and the filtrate was washed with H2O (50 mL) and brine (50 mL). The organic layer was dried over Na$_2$SO$_4$(s) and concentrated under reduced pressure to afford a crude solid, after which the crude product was purified by chromatography on silica (5% EtOAc in hexanes) to afford the title compound (544 mg, 95%) as a pale yellow solid. $^1$H NMR (500 MHz, CDCl$_3$) δ9.17 (d, J=1.6 Hz, 1H), 8.26 (dd, J=2.0, 8.0 Hz, 1H), 7.54 (d, J=7.6 Hz, 1H), 4.43 (q, J=7.2 Hz, 2H), 1.43 (t, J=7.2 Hz, 3H), 0.30 (s, 9H); $^{13}$C NMR (125 MHz, CDCl$_3$) δ167.5, 153.7, 149.2, 139.8, 129.4, 127.8, 105.8, 101.0, 64.3, 17.0, 2.3; HRMS (ESI) m/z 248.1102 [calc'd for C$_{13}$H$_{18}$NO$_2$Si (M+H)$^+$ 248.1102].

Ethyl 2-ethynylpyridine-5-carboxylate

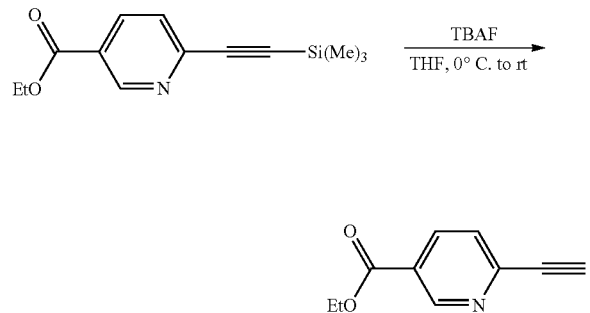

Procedure:

Ethyl 2-(2-trimethylsilylethynyl)pyridine-5-carboxylate (400 mg, 1.6 mmoles) was added to a flame dried flask. The flask was evacuated and purged with nitrogen, after which THF (1.6 mL) was added on ice. A solution of TBAF in THF (1.0 M, 1.9 mL) was added dropwise while stirring on ice, after which the reaction was allowed to come to room temperature while stirring. After 20 min, the reaction was concentrated in vacuo and the crude residue was partitioned between EtOAc (10 mL) and 10% NaHCO$_3$ (10 mL). The organic layer was collected, and the aqueous layer extracted with EtOAc (10 mL). The combined organic extracts were dried over Na$_2$SO$_4$(s) and concentrated under reduced pressure to afford a crude solid, after which the crude product was purified by chromatography on silica (20% EtOAc in hexanes) to afford the title compound (144 mg, 51%) as a pale yellow solid. $^1$H NMR (400 MHz, CDCl$_3$) δ 9.19 (d, J=1.6 Hz, 1H), 8.29 (dd, J=2.0, 8.0 Hz, 1H), 7.56 (d, J=8.4 Hz, 1H), 4.43 (q, J=7.2 Hz, 2H), 3.33 (s, 1H), 1.43 (t, J=7.2 Hz, 3H); $^{13}$C NMR (100 MHz, CDCl$_3$) δ164.6, 151.0, 145.7, 137.2, 126.9, 125.6, 82.3, 79.8, 61.7, 14.2; HRMS (ESI) m/z 176.0708 [calc'd for C$_{10}$H$_{10}$NO$_2$ (M+H)$^+$ 176.0707].

5-Methoxycarbonyl-2-(4-methoxycarbonylpyridin-2-yl)pyridine N-oxide

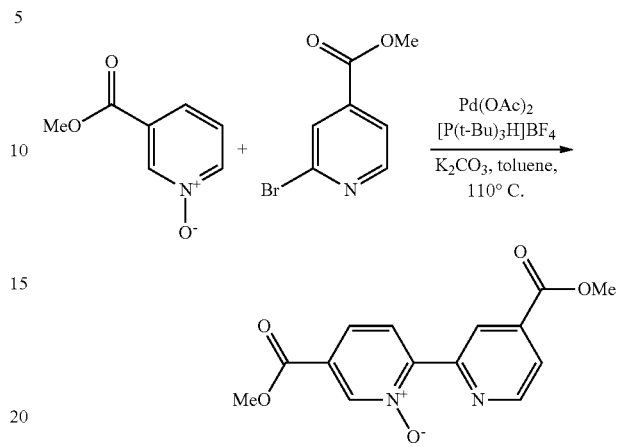

Procedure:

Pd(OAc)$_2$ (36 mg, 0.16 mmoles), [P(t-Bu)$_3$H]BF$_4$ (142 mg, 0.49 mmoles), K$_2$CO$_3$ (903 mg, 6.5 mmoles), methyl 2-bromoisonicotinate (705 mg, 3.3 mmoles), and 3-methoxycarbonylpyridine N-oxide (2000 mg, 13 mmoles) were added to a dried flask. The flask was fitted with a reflux condenser capped with a septum, evacuated, and purged with nitrogen (~5 times). Dry toluene (22 mL) was added via syringe, and the reaction was stirred at 110° C. for 18 h. The reaction mixture was cooled and filtered through Celite®, and the filtrate concentrated under reduced pressure. The crude product was then purified by chromatography on silica (15% acetone in 1:1 DCM/hexanes) to afford the title compound (537 mg, 57%) as a pale orange solid. $^1$H NMR (400 MHz, CDCl$_3$) δ9.49 (s, 1H), 8.89 (s, 1H), 8.88 (d, J=5.2 Hz, 1H), 8.30 (d, J=8.4 Hz, 1H), 7.94 (dd, J=1.2, 5.2 Hz, 1H), 7.90 (dd, J=1.2, 8.4 Hz, 1H), 3.98 (s, 3H), 3.97 (s, 3H); $^{13}$C NMR (100 MHz, CDCl$_3$) δ165.3, 163.4, 150.2, 149.9, 149.4, 141.9, 138.0, 128.9, 127.7, 125.7, 124.9, 124.1, 53.1, 52.8; HRMS (ESI) m/z 289.0826 [calc'd for C$_{14}$H$_{13}$N$_2$O$_5$ (M+H)$^+$ 289.0819].

Dimethyl 2,2'-bipyridine-4,5'-dicarboxylate

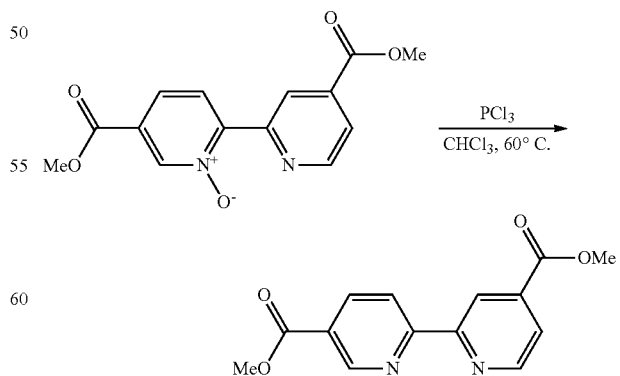

Procedure:

5-Methoxycarbonyl-2-(4-methoxycarbonylpyridin-2-yl) pyridine N-oxide (75 mg, 0.26 mmoles) was dissolved in dry CHCl$_3$ (8.7 mL), after which PCl$_3$ (30 μL, 0.31 mmoles) was added. The reaction was stirred at 60° C. until the starting material was consumed completely, as judged by TLC. The reaction was quenched by the dropwise addition of saturated Na$_2$CO$_3$ (10 mL) while stirring on ice. The product was extracted with CHCl$_3$ (4×10 mL), and the combined organics were dried over Na$_2$SO$_4$(s) and concentrated under reduced pressure to afford the title compound (69 mg, 98%) as a pale yellow solid. $^1$H NMR (400 MHz, CDCl$_3$) δ 9.30 (d, J=1.6 Hz, 1H), 9.00 (s, 1H), 8.85 (d, J=5.2 Hz, 1H), 8.52 (d, J=8.0 Hz, 1H), 8.43 (dd, J=2.0, 8.4 Hz, 1H), 7.92 (dd, J=1.6, 5.2 Hz, 1H), 4.01 (s, 3H), 3.99 (s, 1H); $^{13}$C NMR (100 MHz, CDCl$_3$) δ165.7, 165.5, 158.6, 156.2, 150.6, 150.1, 138.6, 138.1, 126.0, 123.5, 121.1, 120.6, 52.8, 52.5; HRMS (ESI) m/z 273.0882 [calc'd for C$_{14}$H$_{13}$N$_2$O$_4$ (M+H)$^+$ 273.0870].

2-(Thiazol-2-yl)pyridine

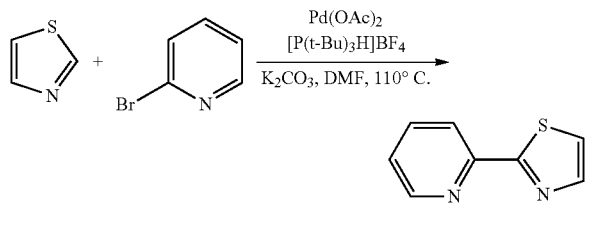

Procedure:
Pd(OAc)$_2$ (35.5 mg, 0.16 mmoles), [P(t-Bu)$_3$H]BF$_4$ (137.5 mg, 0.47 mmoles), and K$_2$CO$_3$ (874 mg, 6.3 mmoles) were added to a dried flask. The flask was fitted with a reflux condenser capped with a septum, evacuated, and purged with nitrogen (~5 times). A degassed solution of thiazole (1.08 g, 12.7 mmoles) and 2-bromopyridine (500 mg, 3.2 mmoles) in dry DMF (16 mL) was added via syringe, and the reaction was stirred at 110° C. for 24 hours. The reaction mixture was cooled, H$_2$O (60 mL) was added, and the aqueous layer was extracted with ether (4×60 mL). The combined organics were washed with H$_2$O (1×100 mL) and brine (1×100 mL), dried over Na$_2$SO$_4$(s), and concentrated under reduced pressure. The crude product was then purified by silica gel chromatography (20-40% EtOAc in hexanes followed by 2% acetone in 1:1 DCM/hexanes) to afford the title compound (142 mg, 28%) as a white solid. $^1$H NMR (400 MHz, CDCl$_3$) δ8.58 (d, J=4.8 Hz, 1H), 8.16 (d, J=8.0 Hz, 1H), 7.89 (d, J=3.2 Hz, 1H), 7.75 (td, J=1.6, 8.0 Hz, 1H), 7.41 (d, J=3.2 Hz, 1H), 7.26 (ddd, J=1.2, 4.8, 8.0 Hz, 1H); $^{13}$C NMR (100 MHz, CDCl$_3$) δ169.3, 151.3, 149.4, 144.0, 137.0, 124.4, 121.4, 119.6; HRMS (EI) m/z 162.0247 [calc'd for C$_8$H$_7$N$_2$S (M)$^+$ 162.0247].

2-(Oxazol-2-yl)pyridine

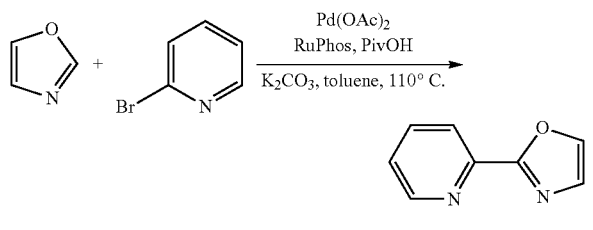

Procedure:
Pd(OAc)$_2$ (33 mg, 0.15 mmoles), RuPhos (135 mg, 0.29 mmoles), pivalic acid (119 mg, 1.2 mmoles) and K$_2$CO$_3$ (1.2 g, 8.7 mmoles) were added to a dried flask. The flask was fitted with a reflux condenser capped with a septum, evacuated, and purged with nitrogen (~5 times). A degassed solution of oxazole (400 mg, 5.8 mmoles) and 2-bromopyridine (457 mg, 2.9 mmoles) in dry toluene (14.5 mL) was added via syringe, and the reaction was stirred at 110° C. for 24 hours. The reaction mixture was cooled and filtered through Celite®, and the filtrate concentrated under reduced pressure. The crude product was then purified by chromatography on silica (20-75% EtOAc in hexanes followed by 10% acetone in DCM/hexanes) to afford the title compound (62 mg, 7%) as a golden oil. $^1$H NMR (500 MHz, CDCl$_3$) δ8.67 (d, J=5.0 Hz, 1H), 8.08 (d, J=8.0 Hz, 1H), 7.78-7.74 (m, 2H), 7.30 (ddd, J=1.0, 5.0, 8.0 Hz, 1H), 7.25 (s, 1H); $^{13}$C NMR (125 MHz, CDCl$_3$) δ160.7, 149.9, 146.0, 139.8, 137.0, 128.8, 124.7, 122.0; HRMS (EI) m/z 146.0472 [calc'd for C$_8$H$_7$N$_2$O (M)$^+$ 146.0475].

2-(Pyridin-2-yl)pyrazine-1-oxide

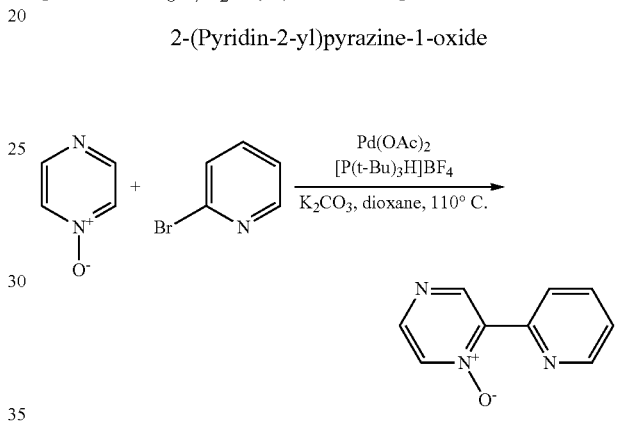

Procedure:
Pd(OAc)$_2$ (39.0 mg, 0.17 mmoles), [P(t-Bu)$_3$H]BF$_4$ (151 mg, 0.52 mmoles), pyrazine-1-oxide (1.0 g, 10.4 mmoles), and K$_2$CO$_3$ (959 mg, 6.9 mmoles) were added to a dried flask. The flask was fitted with a reflux condenser capped with a septum, evacuated, and purged with nitrogen (~5 times). A degassed solution of 2-bromopyridine (548 mg, 3.5 mmoles) in dry dioxane (17 mL) was added via syringe, and the reaction was stirred at 110° C. for 18 hours. The reaction mixture was cooled and filtered through Celite®, and the filtrate was concentrated under reduced pressure. The crude product was then purified by chromatography on silica (30% acetone in hexanes) to afford the title compound (312 mg, 52%) as a pale yellow solid. $^1$H NMR (400 MHz, CDCl$_3$) δ9.35 (s, 1H), 8.75-8.72 (m, 2H), 8.38 (d, J=4.0 Hz, 1H), 8.15 (dd, J=0.4, 4.0 Hz, 1H), 7.81 (ddd, J=1.6, 2.0, 8.0 Hz, 1H), 7.25 (ddd, J=0.8, 4.8, 8.0 Hz, 1H); $^{13}$C NMR (100 MHz, CDCl$_3$) δ149.9, 149.7, 147.3, 145.8, 142.2, 136.5, 134.5, 125.4, 124.8; HRMS (ESI) m/z 174.0662 [calc'd for C$_9$H$_8$N$_3$O (M+H)$^+$ 174.0662].

6-(Pyridin-2-yl)pyridazine-1-oxide

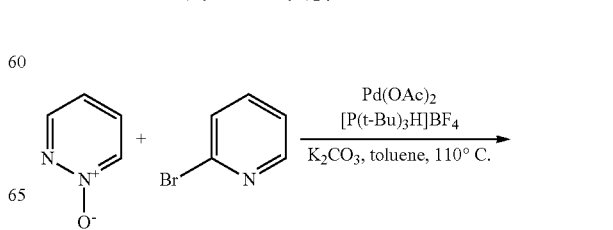

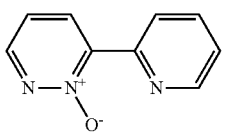

Procedure:

Pd(OAc)$_2$ (29.0 mg, 0.13 mmoles), [P(t-Bu)$_3$H]BF$_4$ (113 mg, 0.39 mmoles), pyridazine-1-oxide (500 mg, 5.2 mmoles), and K$_2$CO$_3$ (719 mg, 5.2 mmoles) were added to a dried flask. The flask was fitted with a reflux condenser capped with a septum, evacuated, and purged with nitrogen (~5 times). A degassed solution of 2-bromopyridine (411 mg, 2.6 mmoles) in dry toluene (13 mL) was added via syringe, and the reaction was stirred at 110° C. for 18 hours. The reaction mixture was cooled, filtered through Celite®, and the filtrate was concentrated under reduced pressure. The crude product was then purified by chromatography on silica (35% acetone in hexanes) to afford the title compound (206 mg, 46%) as a grey solid. $^1$H NMR (400 MHz, CDCl$_3$) δ8.90 (d, J=8.0 Hz, 1H), 8.70 (d, J=4.0 Hz, 1H), 8.63 (dd, J=1.6, 8.0 Hz, 1H), 8.47 (s, 1H), 7.84 (t, J=7.6 Hz, 1H), 7.36 (dd, J=5.2, 7.2 Hz, 1H), 7.19 (dd, J=5.2, 8.0 Hz, 1H); $^{13}$C NMR (100 MHz, CDCl$_3$) δ149.8, 149.5, 148.2, 142.5, 136.7, 135.6, 125.0, 124.7, 116.5; HRMS (ESI) m/z 174.0658 [calc'd for C$_9$H$_8$N$_3$O (M+H)$^+$ 174.0662].

2-(Pyridin-2-yl)pyrazine

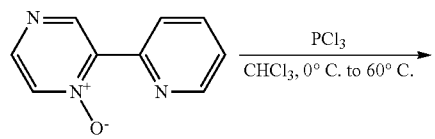

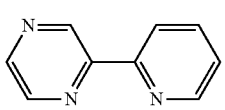

Procedure:

2-(Pyridin-2-yl)pyrazine-1-oxide (200 mg, 1.2 mmoles) was dissolved in dry CHCl$_3$ (23 mL) and cooled to 0° C. in an ice bath, after which PCl$_3$ (360 μL, 4.2 mmoles) was added dropwise with stirring. The reaction was stirred at 60° C. until the starting material was completely consumed, as judged by TLC. The reaction was quenched by the dropwise addition of saturated Na$_2$CO$_3$ (20 mL) while stirring on ice. The product was extracted with CHCl$_3$ (4×20 mL), and the combined organics were dried over Na$_2$SO$_4$(s) and concentrated under reduced pressure. The crude product was then purified by chromatography on silica (30% EtOAc in hexanes) to afford the title compound (103 mg, 57%) as a pale yellow solid. $^1$H NMR (400 MHz, CDCl$_3$) δ9.63 (d, J=1.2 Hz, 1H), 8.71-8.69 (m, 1H), 8.60-8.58 (m, 2H), 8.34 (d, J=8.0 Hz, 1H), 7.82 (ddd, J=1.6, 2.0, 8.0 Hz, 1H), 7.34 (ddd, J=1.2, 4.8, 7.6 Hz, 1H); $^{13}$C NMR (100 MHz, CDCl$_3$) δ154.2, 151.1, 149.4, 144.4, 143.5, 143.3, 137.0, 124.4, 121.4; HRMS (ESI) m/z 158.0708 [calc'd for C$_9$H$_8$N$_3$ (M+H)$^+$ 158.0713].

2-(Pyridin-2-yl)pyridazine

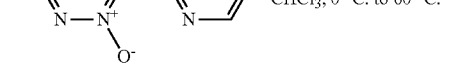

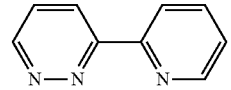

Procedure:

6-(Pyridin-2-yl)pyridazine-1-oxide (150 mg, 0.87 mmoles) was dissolved in dry CHCl$_3$ 4.3 mL) and cooled to 0° C. in an ice bath, after which PCl$_3$ (230 μL, 2.6 mmoles) was added dropwise with stirring. The reaction was stirred at 60° C. until the starting material was completely consumed, as judged by TLC. The reaction was quenched by the dropwise addition of saturated Na$_2$CO$_3$ (10 mL) while stirring on ice. The product was extracted with CHCl$_3$ (4×10 mL), and the combined organics were dried over Na$_2$SO$_4$(s) and concentrated under reduced pressure. The crude product was then purified by chromatography on silica (40% EtOAc in hexanes) to afford the title compound (50 mg, 37%) as a brown solid. $^1$H NMR (400 MHz, CDCl$_3$) δ9.19 (dd, J=1.6, 5.2 Hz, 1H), 8.70-8.67 (m, 2H), 8.55 (dd, J=1.6, 8.8 Hz, 1H), 7.87 (td, J=1.6, 8.0 Hz, 1H), 7.59 (dd, J=4.8, 8.8 Hz, 1H), 7.38 (ddd, J=1.2, 4.8, 7.6 Hz, 1H); $^{13}$C NMR (100 MHz, CDCl$_3$) δ158.6, 153.5, 151.2, 149.4, 137.2, 127.0, 124.7, 124.4, 121.6; HRMS (ESI) m/z 158.0714 [calc'd for C$_9$H$_8$N$_3$ (M+H)$^+$ 158.0713].

Methyl 2-(5-methoxycarbonylthiazol-2-yl)pyridine-5-carboxylate

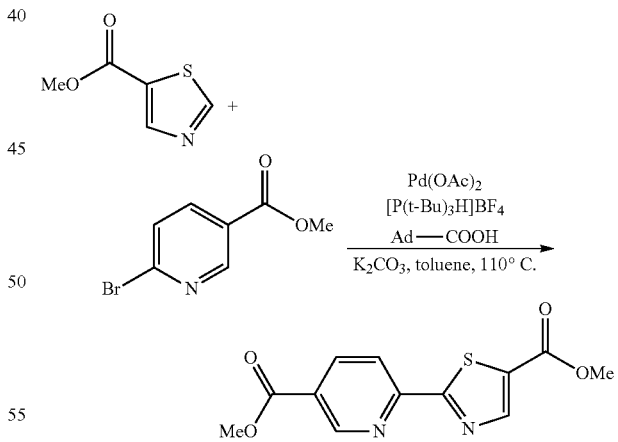

Procedure:

Pd(OAc)$_2$ (3.9 mg, 0.017 mmoles), [P(t-Bu)$_3$H]BF$_4$ (10.0 mg, 0.035 mmoles), 1-adamantanecarboxylic acid (18.4 mg, 0.10 mmoles), K$_2$CO$_3$ (96.5 mg, 0.70 mmoles), methyl thiazole-5-carboxylate (50 mg, 0.35 mmoles), and methyl 6-bromonicotinate (113 mg, 0.52 mmoles) were added to a dried flask. The flask was fitted with a reflux condenser capped with a septum, evacuated, and purged with nitrogen (~5 times). Dry toluene (1.7 mL) was added via syringe, and the reaction was stirred at 110° C. for 48 h. The reaction mixture was cooled and filtered through Celite®, and the filtrate was concentrated under reduced pressure. The crude product was then purified by chromatography on silica (3% acetone in 1:1 DCM/hexanes) to afford the title compound (28 mg, 29%) as a white solid. $^1$H NMR (400 MHz, CDCl$_3$) δ9.22 (s, 1H), 8.51 (s, 1H), 8.43 (dd, J=2.0, 8.0 Hz, 1H), 8.29 (d, J=8.0 Hz, 1H), 4.00 (s, 3H), 3.96 (s, 3H); $^{13}$C NMR (100 MHz, CDCl$_3$) δ172.7, 165.1, 161.8, 153.6, 150.9, 149.7, 138.4, 131.7, 127.1, 119.6, 52.6, 52.6; HRMS (ESI) m/z 279.0439 [calc'd for C$_{12}$H$_{11}$N$_2$O$_4$S (M+H)$^+$ 279.0435].

For experiments with mammalian cells, this compound was recrystallized from EtOAc to afford a white crystalline solid.

Methyl 2-(4-methoxycarbonylthiazol-2-yl)pyridine-5-carboxylate

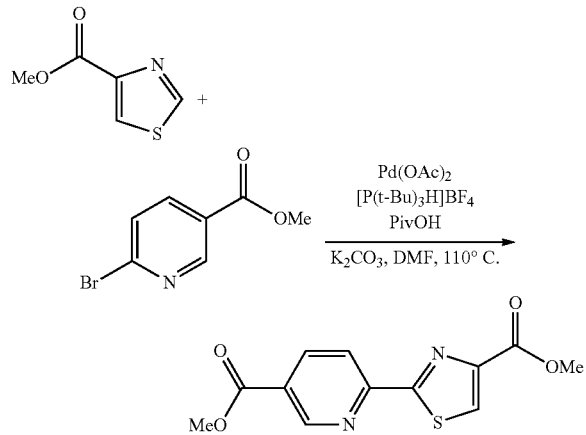

Procedure:

Pd(OAc)$_2$ (15.7 mg, 0.070 mmoles), [P(t-Bu)$_3$H]BF$_4$ (60.7 mg, 0.21 mmoles), pivalic acid (28.5 mg, 0.28 mmoles), K$_2$CO$_3$ (386 mg, 2.8 mmoles), methyl thiazole-4-carboxylate (200 mg, 1.4 mmoles), and methyl 6-bromonicotinate (603 mg, 2.8 mmoles) were added to a dried flask. The flask was fitted with a reflux condenser capped with a septum, evacuated, and purged with nitrogen (~5 times). Dry DMF (7 mL) was added via syringe, and the reaction was stirred at 110° C. for 6 h. The reaction mixture was cooled and filtered through Celite®, and the filtrate was concentrated under reduced pressure. The crude product was then purified by chromatography on silica (1% acetone in DCM) to afford the title compound (39 mg, 10%) as a white solid. $^1$H NMR (400 MHz, CDCl$_3$) δ9.18 (dd, J=0.8, 2.0 Hz, 1H), 8.41 (dd, J=2.0, 8.4 Hz, 1H), 8.38 (dd, J=0.8, 8.4 Hz, 1H), 8.33 (s, 1H), 3.99 (s, 3H), 3.98 (s, 3H); $^{13}$C NMR (100 MHz, CDCl$_3$) δ168.7, 165.1, 161.7, 153.3, 150.7, 148.3, 138.3, 130.7, 126.9, 119.6, 52.6, 52.6; HRMS (ESI) m/z 279.0423 [calc'd for C$_{12}$H$_{11}$N$_2$O$_4$S (M+H)$^+$ 279.0435].

Methyl 2-(5-ethoxycarbonyloxazol-2-yl)pyridine-5-carboxylate

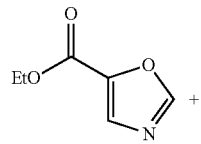

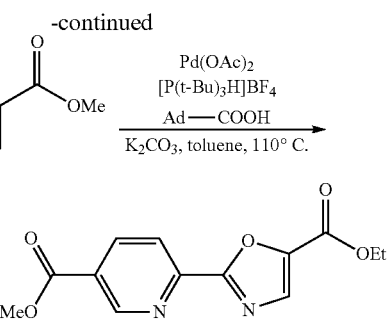

Procedure:

Pd(OAc)$_2$ (31.8 mg, 0.14 mmoles), [P(t-Bu)$_3$H]BF$_4$ (123.2 mg, 0.42 mmoles), 1-adamantanecarboxylic acid (153 mg, 0.85 mmoles), K$_2$CO$_3$ (782 mg, 5.7 mmoles), and methyl 6-bromonicotinate (918 mg, 4.3 mmoles) were added to a dried flask. The flask was fitted with a reflux condenser capped with a septum, evacuated, and purged with nitrogen (~5 times). A degassed solution of ethyl oxazole-5-carboxylate (400 mg, 2.8 mmoles) in dry toluene (7 mL) was added via syringe, and the reaction was stirred at 110° C. for 8 h. The reaction mixture was cooled and filtered through Celite®, and the filtrate was concentrated under reduced pressure. The crude product was then purified by chromatography on silica (30% EtOAc in hexanes followed by 2% acetone in 1:1 DCM:hexanes) to afford the title compound (183 mg, 23%) as a white solid. $^1$H NMR (400 MHz, CDCl$_3$) δ9.37 (dd, J=0.8, 2.0 Hz, 1H), 8.47 (dd, J=2.0, 8.0 Hz, 1H), 8.30 (dd, J=0.8, 8 Hz, 1H), 7.96 (s, 1H), 4.46 (q, J=7.2 Hz, 2H), 4.00 (s, 3H), 1.43 (t, J=7.2 Hz, 3H); $^{13}$C NMR (100 MHz, CDCl$_3$) δ164.9, 161.6, 157.5, 151.5, 148.0, 143.8, 138.3, 135.5, 127.3, 122.5, 61.9, 52.7, 14.3; HRMS (ESI) m/z 277.0823 [calc'd for C$_{13}$H$_{13}$N$_2$O$_5$ (M+H)$^+$ 279.0819]. For experiments with mammalian cells, this compound was recrystallized from EtOAc to afford a white crystalline solid Methyl 2-(4-ethoxycarbonyloxazol-2-yl)pyridine-5-carboxylate

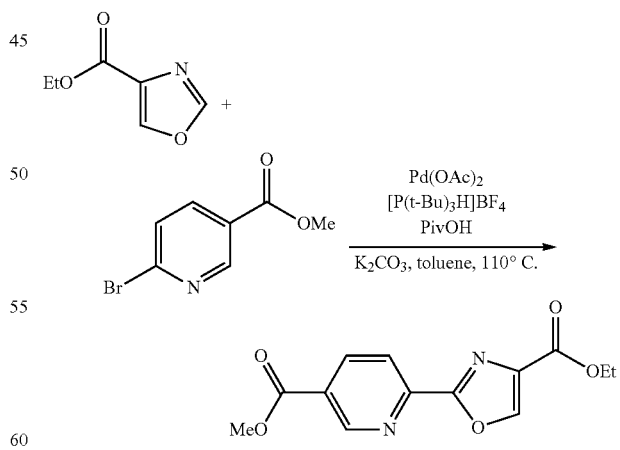

Procedure:

Pd(OAc)$_2$ (15.9 mg, 0.071 mmoles), [P(t-Bu)$_3$H]BF$_4$ (61.8 mg, 0.21 mmoles), pivalic acid (29.0 mg, 0.28 mmoles), K$_2$CO$_3$ (391 mg, 2.8 mmoles), ethyl oxazole-4-carboxylate (200 mg, 1.4 mmoles), and methyl 6-bromonicotinate (612 mg, 2.8 mmoles) were added to a dried flask.

The flask was fitted with a reflux condenser capped with a septum, evacuated, and purged with nitrogen (~5 times). Dry toluene (7 mL) was added via syringe, and the reaction was stirred at 110° C. for 24 h. The reaction mixture was cooled and filtered through Celite®, and the filtrate was concentrated under reduced pressure. The crude product was then purified via chromatography on silica (2% acetone in DCM followed by 10% acetone 1:1 DCM:hexanes) to afford the title compound (113 mg, 29%) as a white solid. $^1$H NMR (400 MHz, CDCl$_3$) δ9.31 (dd, J=0.8, 2.0 Hz, 1H), 8.46 (dd, J=2.0, 8.4 Hz, 1H), 8.42 (s, 1H), 8.38 (dd, J=0.8, 8.4 Hz, 1H), 4.45 (q, J=7.2 Hz, 2H), 4.00 (s, 3H), 1.42 (t, J=7.2 Hz, 3H); $^{13}$C NMR (100 MHz, CDCl$_3$) δ164.9, 160.8, 160.2, 151.1, 148.0, 145.2, 138.3, 135.3, 127.1, 122.3, 61.6, 52.7, 14.3; HRMS (ESI) m/z 277.0815 [calc'd for C$_{13}$H$_{13}$N$_2$O$_5$ (M+H)$^+$ 277.0823].

Methyl 2-(5-methoxycarbonyl-1-methyl-1H-imidazol-2-yl)pyridine-5-carboxylate

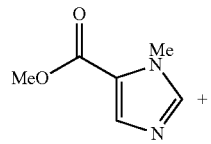
+
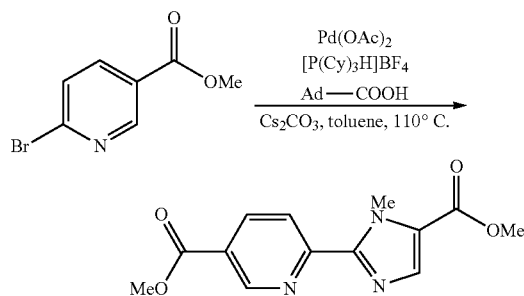

Procedure:

Pd(OAc)$_2$ (32 mg, 0.14 mmoles), [P(Cy)$_3$H]BF$_4$ (158 mg, 0.43 mmoles), 1-adamantanecarboxylic acid (258 mg, 1.4 mmoles), Cs$_2$CO$_3$ (1.9 g, 5.7 mmoles), methyl 6-bromonicotinate (618 mg, 2.9 mmoles) and methyl 1-methyl-1H-imidazole-5-carboxylate (400 mg, 2.9 mmoles) were added to a dried flask. The flask was fitted with a reflux condenser capped with a septum, evacuated, and purged with nitrogen (~5 times). Dry toluene (4.8 mL) was added via syringe, and the reaction was stirred at 110° C. for 48 h. The reaction mixture was cooled and filtered through Celite®, and the filtrate was concentrated under reduced pressure. The crude product was then purified by chromatography on silica (30% EtOAc in hexanes) to afford the title compound (40 mg, 5%) as a pale yellow solid. $^1$H NMR (400 MHz, CDCl$_3$) δ 9.23 (d, J=1.2 Hz, 1H), 8.38 (dd, J=2.0, 8.4 Hz, 1H), 8.28 (d, J=8.4 Hz, 1H), 7.84 (s, 1H), 4.43 (s, 3H), 3.98 (s, 3H), 3.89 (s, 3H); $^{13}$C NMR (100 MHz, CDCl$_3$) δ165.4, 160.8, 153.2, 149.8, 148.2, 137.6, 137.3, 125.6, 125.1, 123.8, 52.5, 51.6, 35.0; HRMS (ESI) m/z 298.0796 [calc'd for C$_{13}$H$_{13}$N$_3$O$_4$Na (M+Na)$^+$ 298.0799].

Methyl 2-(5-methoxycarbonylpyridin-2-yl)pyrazine-5-carboxylate-1-oxide

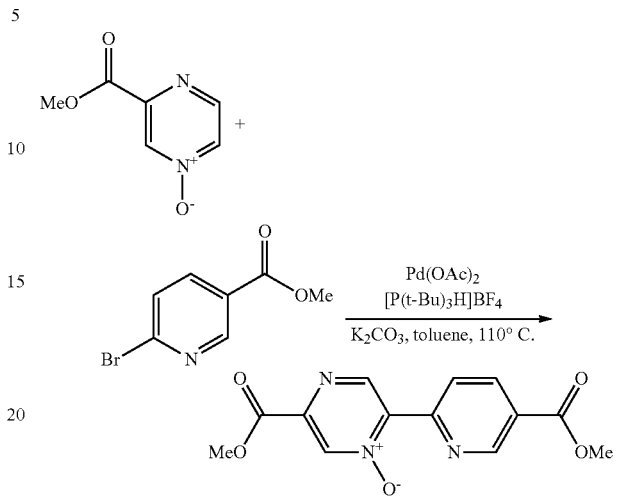

Procedure:

Pd(OAc)$_2$ (21 mg, 0.09 mmoles), [P(t-Bu)$_3$H]BF$_4$ (81 mg, 0.28 mmoles), K$_2$CO$_3$ (511 mg, 3.7 mmoles), methyl 6-bromonicotinate (400 mg, 1.9 mmoles), and methyl pyrazine-3-carboxylate-1-oxide (571 mg, 3.7 mmoles) were added to a dried flask. The flask was fitted with a reflux condenser capped with a septum, evacuated, and purged with nitrogen (~5 times). Dry toluene (9 mL) was added via syringe, and the reaction was stirred at 110° C. for 24 h. The reaction mixture was cooled and filtered through Celite®, and the filtrate was concentrated under reduced pressure. The crude product was then further purified by chromatography on silica (45% EtOAc in hexanes) to afford the title compound (100 mg) as a pale orange solid. Due to the presence of minor contaminants that were difficult to remove by chromatography or recrystallization, the slightly crude product was used directly in the next reaction before further purification and characterization. $^1$H NMR (400 MHz, CDCl$_3$) δ9.63 (s, 1H), 9.38 (dd, J=0.4, 2.0, Hz, 1H), 9.06 (dd, J=0.8, 8.4 Hz, 1H), 8.89 (d, J=0.4 Hz, 1H), 8.48 (dd, J=2.0, 8.4 Hz, 1H), 4.10 (s, 3H), 4.03 (s, 3H); HRMS (ESI) m/z 290.0770 [calc'd for C$_{13}$H$_{12}$N$_3$O$_5$ (M+H)$^+$ 290.0772].

Methyl 2-(5-methoxycarbonylpyridin-2-yl)pyrazine-5-carboxylate

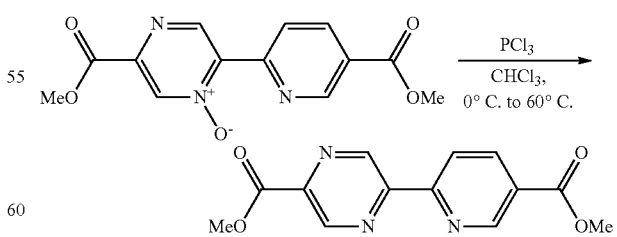

Procedure:

Methyl 2-(5-methoxycarbonylpyridin-2-yl)pyrazine-5-carboxylate-1-oxide (100 mg, 0.35 mmoles) was dissolved in dry CHCl$_3$ (1.5 mL) and cooled to 0° C. in an ice bath, after which PCl$_3$ (100 μL, 1.0 mmoles) was added dropwise with stirring. The reaction was stirred at 60° C. until the starting material was consumed completely, as judged by TLC. The reaction was quenched by the dropwise addition of saturated Na$_2$CO$_3$ (10 mL) while stirring on ice. The product was extracted with CHCl$_3$ (3×10 mL), and the combined organics were dried over Na$_2$SO$_4$(s) and concentrated under reduced pressure. The crude product was then recrystallized from CHCl$_3$ and then EtOAc to afford the title compound (28 mg, 6% over two steps) as a pale yellow solid. $^1$H NMR (500 MHz, CDCl$_3$) δ9.84 (d, J=1.5 Hz, 1H), 9.38 (d, J=1.0 Hz, 1H), 9.36 (dd, J=0.5, 2.0 Hz, 1H), 8.58 (d, J=0.5, 8.0 Hz, 1H), 8.50 (dd, J=2.0, 8.5 Hz, 1H), 4.11 (s, 3H), 4.03 (s, 3H); $^{13}$C NMR (125 MHz, CDCl$_3$) δ165.4, 164.4, 156.4, 152.4, 150.8, 145.2, 143.3, 143.0, 138.4, 126.9, 121.9, 53.3, 52.7; HRMS (ESI) m/z 274.0824 [calc'd for C$_{13}$H$_{12}$N$_3$O$_4$ (M+H)$^+$ 274.0823].

Methyl 6-(5-methoxycarbonylpyridin-2-yl)pyridazine-3-carboxylate-1-oxide

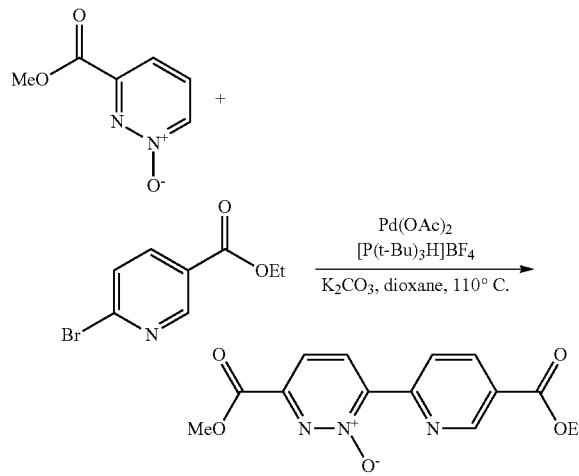

Procedure:

Pd(OAc)$_2$ (7.3 mg, 0.033 mmoles), [P(t-Bu)$_3$H]BF$_4$ (28 mg, 0.098 mmoles), K$_2$CO$_3$ (180 mg, 1.3 mmoles), ethyl 6-bromonicotinate (150 mg, 0.65 mmoles), and methyl pyridazine-3-carboxylate-1-oxide (200 mg, 1.3 mmoles) were added to a dried flask. The flask was fitted with a reflux condenser capped with a septum, evacuated, and purged with nitrogen (~5 times). Dry dioxane (4 mL) was added via syringe, and the reaction was stirred at 110° C. for 18 h. The reaction mixture was cooled and filtered through Celite®, and the filtrate concentrated under reduced pressure. The crude product was then further purified by chromatography on silica (40% EtOAc in hexanes) to afford the title compound (82 mg) as a pale orange solid. Due to the presence of minor contaminants that were difficult to remove by chromatography or recrystallization, the slightly crude product was used directly in the next reaction before further purification and characterization. $^1$H NMR (500 MHz, CDCl$_3$) δ9.26 (d, J=2.0 Hz, 1H), 9.06 (d, J=8.5, Hz, 1H), 8.85 (d, J=8.5 Hz, 1H), 8.42 (dd, J=2.0, 8.5 Hz, 1H), 7.85 (dd, J=8.5 Hz, 1H), 4.41 (q, J=7.0 Hz, 2H), 4.00 (s, 3H), 1.40 (t, J=7.0 Hz, 3H); HRMS (ESI) m/z 304.0931 [calc'd for C$_{14}$H$_{14}$N$_3$O$_5$ (M+H)$^+$ 304.0928].

Methyl 6-(5-ethoxycarbonylpyridin-2-yl)pyridazine-3-carboxylate

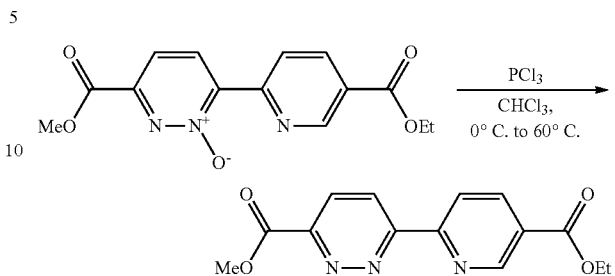

Procedure:

Methyl 6-(5-methoxycarbonylpyridin-2-yl)pyridazine-3-carboxylate-1-oxide (80 mg, 0.28 mmoles) was dissolved in dry CHCl$_3$ (1.3 mL) and cooled to 0° C. in an ice bath, after which PCl$_3$ (370 µL, 3.7 mmoles) was added dropwise with stirring. The reaction was stirred at 60° C. until the starting material was consumed completely, as judged by TLC. The reaction was quenched by the dropwise addition of saturated Na$_2$CO$_3$ (10 mL) while stirring on ice. The product was extracted with CHCl$_3$ (4×10 mL), and the combined organics were dried over Na$_2$SO$_4$(s) and concentrated under reduced pressure. The crude product was then purified by chromatography on silica (35% EtOAc in hexanes) to afford the title compound (37 mg, 20% over two steps) as a pale yellow solid. $^1$H NMR (500 MHz, CDCl$_3$) δ9.12 (d, J=1.5 Hz, 1H), 8.66 (d, J=8.0 Hz, 1H), 8.57 (d, J=8.5 Hz, 1H), 8.30 (dd, J=2.0, 8.0 Hz, 1H), 8.14 (d, J=8.5 Hz, 1H), 4.26 (q, J=7.0 Hz, 2H), 3.92 (s, 3H), 1.25 (t, J=7.0 Hz, 3H); $^{13}$C NMR (125 MHz, CDCl$_3$) δ164.7, 164.3, 158.9, 155.5, 151.1, 150.6, 138.2, 128.2, 127.2, 125.3, 121.6, 61.5, 53.3, 14.1; HRMS (ESI) m/z 288.0982 [calc'd for C$_{14}$H$_{14}$N$_3$O$_4$ (M+H)$^+$ 288.0979].

Methyl 2-(4-methoxycarbonyl-1-pivaloyloxymethyl-1H-pyrrol-2-yl)pyridine-5-carboxylate-1-oxide

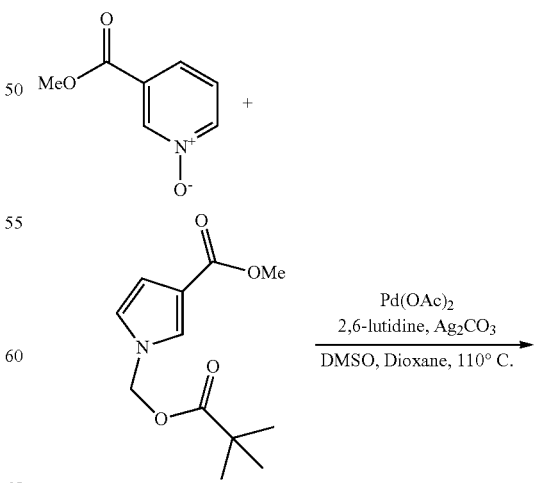

-continued

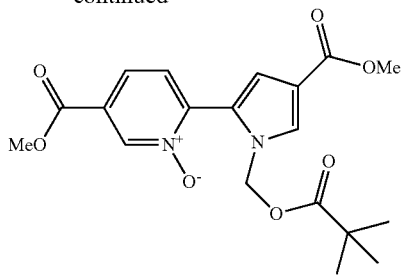

Procedure:

Pd(OAc)$_2$ (9.2 mg, 0.041 mmoles), Ag$_2$CO$_3$ (450 mg, 1.6 mmoles), and 3-methoxycarbonylpyridine-1-oxide (125 mg, 0.82 mmoles) were added to a dried flask. The flask was fitted with a reflux condenser capped with a septum, evacuated, and purged with nitrogen (~5 times). A degassed solution of methyl 1-pivaloyloxymethyl-1H-pyrrole-3-carboxylate (215 mg, 0.90 mmoles), 2,6-lutidine (29 µL, 0.25 mmoles), and DMSO (275 µL, 5% [v/v]) in dry dioxane (5.2 mL) was added via syringe, and the reaction was stirred at 110° C. for 48 h. The reaction mixture was cooled and filtered through Celite®, and the filtrate was concentrated under reduced pressure. The crude product was then purified by chromatography on silica (60-100% EtOAC in hexanes) to afford the title compound (30 mg, 9.4%) as a yellow solid. $^1$H NMR (400 MHz, CDCl$_3$) δ8.88 (d, J=1.2 Hz, 1H), 7.87 (dd, J=1.2, 8.0 Hz, 1H), 7.67 (d, J=2.0 Hz, 1H), 7.50 (d, J=8.0 Hz, 1H), 6.87 (d, J=1.6 Hz, 1H), 6.03 (s, 2H), 3.99 (s, 3H), 3.83 (s, 3H), 1.03 (s, 9H); $^{13}$C NMR (100 MHz, CDCl$_3$) δ177.1, 164.1, 163.2, 145.5, 141.2, 130.6, 128.9, 128.4, 125.9, 125.4, 117.4, 115.8, 71.5, 53.1, 51.4, 38.6, 26.7; HRMS (ESI) m/z 391.15041 [calc'd for C$_{19}$H$_{23}$N$_2$O$_7$ (M+H)$^+$ 391.1500].

Methyl 2-(4-methoxycarbonyl-1-pivaloyloxymethyl-1H-pyrrol-2-yl)pyridine-5-carboxylate

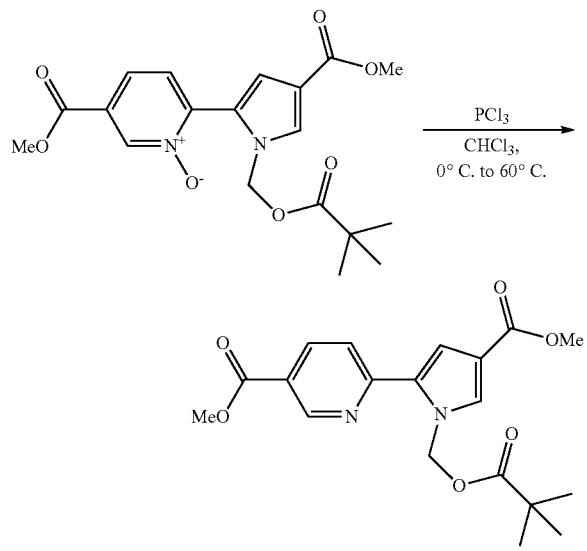

Procedure:

Methyl 2-(4-methoxycarbonyl-1-pivaloyloxymethyl-1H-pyrrol-2-yl)pyridine-5-carboxylate-1-oxide (30 mg, 0.077 mmoles) was dissolved in dry CHCl$_3$ (800 µL) and cooled to 0° C. in an ice bath, after which PCl$_3$ (8.1 µL, 0.092 mmoles) was added. The reaction was stirred at 60° C. until starting material was consumed completely, as judged by TLC. The reaction was quenched by the dropwise addition of saturated Na$_2$CO$_3$ (3 mL) while stirring on ice. The product was extracted with DCM (4×3 mL), and the combined organics were dried over Na$_2$SO$_4$(s) and concentrated under reduced pressure to afford the title compound (28 mg, 97%) as a brown solid. $^1$H NMR (400 MHz, CDCl$_3$) δ9.14 (d, J=0.8, 2.0 Hz, 1H), 8.28 (dd, J=2.4, 8.4 Hz, 1H), 7.66 (dd, J=0.8, 8.4 Hz, 1H), 7.63 (d, J=2.0 Hz, 1H), 7.19 (d, J=1.6 Hz, 1H), 6.49 (s, 2H), 3.97 (s, 3H), 3.86 (s, 3H), 1.08 (s, 9H); $^{13}$C NMR (100 MHz, CDCl$_3$) δ177.5, 165.7, 164.4, 154.2, 150.2, 137.5, 132.1, 131.6, 123.2, 120.3, 116.6, 114.3, 71.5, 52.3, 51.4, 38.7, 26.8; HRMS (ESI) m/z 375.1550 [calc'd for C$_{19}$H$_{23}$N$_2$O$_6$ (M+H)$^+$ 375.1551].

Ethyl 2-(5-ethoxycarbonyl-1H-pyrrol-3-yl)pyridine-5-carboxylate

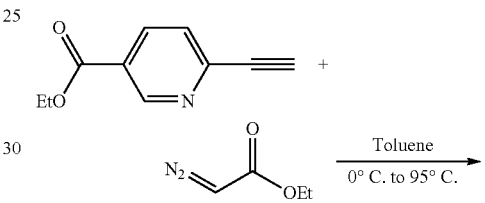

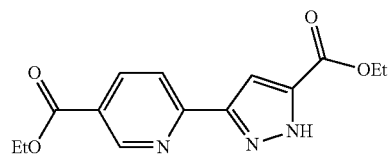

Procedure:

Ethyl 2-ethynylpyridine-5-carboxylate (91 mg, 0.52 mmoles) was dissolved in toluene (5 mL) in a glass vial and the solution was chilled on ice with stirring. A 73% (w/w) solution of ethyl diazoacetate in DCM (162 mg, 1.04 mmoles) was added dropwise, after which the vial was purged with N$_2$(g) and stirred at 95° C. After 24 h, the reaction was chilled on ice and a second portion of ethyl diazoacetate (162 mg, 1.04 mmoles) was added. The reaction was stirred at 95° C. for an addition 24 h, after which the reaction was concentrated under reduced pressure to afford a crude solid. The crude product was then purified by chromatography on silica (30% EtOAc in hexanes) to afford the title compound (125 mg, 83%) as a pale yellow solid. $^1$H NMR (500 MHz, CDCl$_3$) δ12.06 (bs, 1H), 9.29 (dd, J=0.5, 2.0 Hz, 1H), 8.43 (dd, J=2.0, 8.5 Hz, 1H), 7.91 (d, J=8.5 Hz, 1H), 7.46 (s, 1H), 4.483 (q, J=7.0 Hz, 2H), 4.480 (q, J=7.0 Hz, 2H), 1.47 (t, J=7.0 Hz, 6H); $^{13}$C NMR (125 MHz, CDCl$_3$) δ167.6, 164.0, 154.4, 153.6, 148.4, 144.8, 141.1, 128.3, 122.5, 110.2, 64.3, 64.1, 17.0 (2 signals); HRMS (ESI) m/z 312.0952 [calc'd for C$_{14}$H$_{15}$N$_3$O$_4$Na (M+Na)$^+$ 312.0955].

2,2'-Bipyridine-4,5'-dicarboxylic Acid (bipy45'DC)

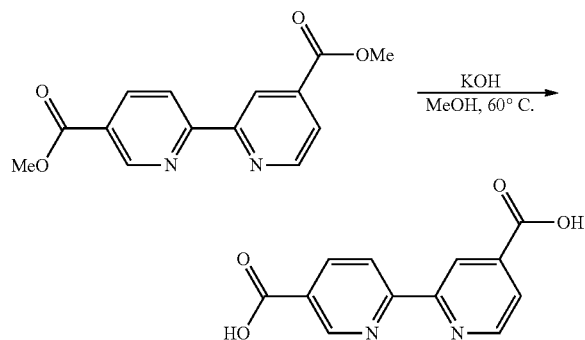

Procedure for bipy45'DC:

Dimethyl 2,2'-bipyridine-4,5'-dicarboxylate (482 mg, 1.8 mmoles) and KOH (460 mg, 7.1 mmoles) were added to a vial. MeOH (9.0 mL) was added to the vial and the reaction mixture was heated to 60° C. until the starting material was consumed completely, as judged by TLC. The reaction mixture was cooled and concentrated under reduced pressure. The crude product was dissolved in water (20 mL). The aqueous layer was washed with EtOAc (1×20 mL), after which the product was precipitated from the aqueous layer by adjusting to pH 3-4 with 1M HCl. After cooling to 4° C., the product was filtered, washed with water (3×5 mL), and dried in vacuo to afford bipy45'DC (412 mg, 95%) as an off-white solid. $^1$H NMR (400 MHz, DMSO-$d_6$) δ 13.67 (bs, 2H), 9.20 (s, 1H), 8.92 (d, J=4.8 Hz, 1H), 8.88 (s, 1H), 8.54 (d, J=8.0 Hz, 1H), 8.44 (dd, J=2.0, 8.4 Hz, 1H), 7.93 (d, J=4.8 Hz, 1H); $^{13}$C NMR (100 MHz, DMSO-$d_6$) δ 166.5, 166.5, 158.0, 155.8 151.2, 150.8, 140.0, 139.0, 127.3, 124.2, 120.9, 120.7; HRMS (ESI) m/z 243.0405 [calc'd for $C_{12}H_7N_2O_4$ (M−H)$^-$ 243.0411].

2-(5-Carboxythiazol-2-yl)pyridine-5-carboxylic Acid

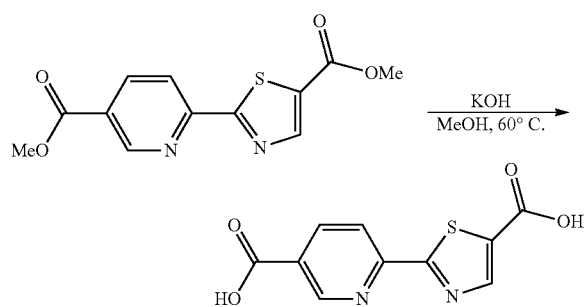

Procedure:

Methyl 2-(5-methoxycarbonylthiazol-2-yl)-pyridine-5-carboxylate (70 mg, 0.25 mmoles) and KOH (63.1 mg, 1.0 mmoles) were added to a vial. MeOH (7.0 mL) was added to the vial and the reaction mixture was heated to 60° C. with stirring until the starting material was completely consumed, as judged by TLC. The reaction mixture was cooled and concentrated under reduced pressure. The crude product was dissolved in water (4 mL). The aqueous layer was washed with EtOAc (1×4 mL), after which the product was precipitated from the aqueous layer by adjusting to pH 2 with 1M HCl. After cooling to 4° C., the product was filtered, washed with water (3×1 mL), and dried in vacuo to afford the title compound (38 mg, 61%) as a pale yellow solid. $^1$H NMR (500 MHz, DMSO-$d_6$) δ 13.80 (bs, 1H), 13.73 (bs, 1H), 9.15 (dd, J=0.5, 2.0 Hz, 1H), 8.56 (s, 1H), 8.48 (dd, J=2.0, 8.0 Hz, 1H), 8.31 (dd, J=0.5, 8.0 Hz, 1H); $^{13}$C NMR (125 MHz, DMSO-$d_6$) δ 172.1, 166.1, 162.6, 153.1, 151.2, 149.9, 139.5, 133.6, 128.6, 120.1; HRMS (ESI) m/z 248.9977 [calc'd for $C_{10}H_5N_2O_4S$ (M−H)$^-$ 248.9975].

2-(4-Carboxythiazol-2-yl)pyridine-5-carboxylic Acid

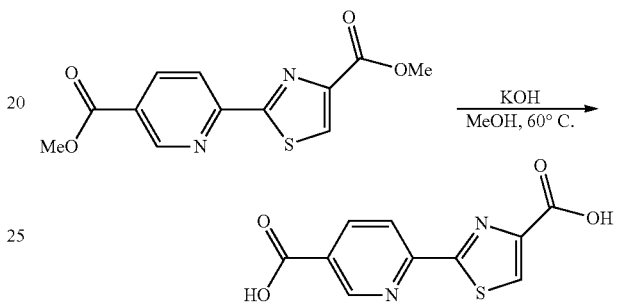

Procedure:

Methyl 2-(4-methoxycarbonylthiazol-2-yl)-pyridine-5-carboxylate (30 mg, 011 mmoles) and KOH (27.8 mg, 0.43 mmoles) were added to a vial. MeOH (3.1 mL) was added to the vial and the reaction mixture was heated to 60° C. with stirring until the starting material was completely consumed, judged by TLC. The reaction mixture was cooled and concentrated under reduced pressure. The crude product was dissolved in water (2 mL). The aqueous layer was washed with EtOAc (1×2 mL), after which the product was precipitated from the aqueous layer by adjusting to pH 3-4 with 1M HCl. After cooling to 4° C., the product was filtered, washed with water (3×1 mL), and dried in vacuo to afford the title compound (21 mg, 78%) as a white solid. $^1$H NMR (500 MHz, DMSO-$d_6$) δ 13.51 (bs, 2H), 9.13 (dd, J=0.5, 2.0 Hz, 1H), 8.67 (s, 1H), 8.47 (dd, J=2.0, 8.5 Hz, 1H), 8.28 (dd, J=0.5, 8.5 Hz, 1H); $^{13}$C NMR (125 MHz, DMSO-$d_6$) δ 168.0, 166.2, 162.5, 153.0, 151.1, 149.4, 139.4, 132.2, 128.6, 119.8; HRMS (ESI) m/z 248.9975 [calc'd for $C_{10}H_5N_2O_4S$ (M−H)$^-$ 248.9975].

2-(5-Carboxyoxazol-2-yl)pyridine-5-carboxylic Acid

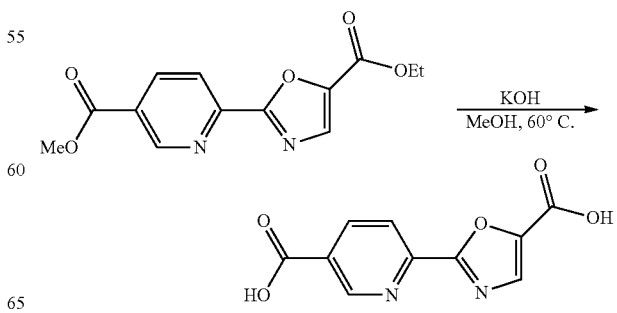

Procedure:

Methyl 2-(5-ethoxycarbonyloxazol-2-yl)-pyridine-5-carboxylate (45 mg, 0.16 mmoles) and KOH (42 mg, 0.65 mmoles). MeOH (4.7 mL) was added to the vial and the reaction mixture was heated to 60° C. with stirring until the starting material was completely consumed, as judged by TLC. The reaction mixture was cooled and concentrated under reduced pressure. The crude product was dissolved in water (2 mL). The aqueous layer was washed with EtOAc (1×2 mL), after which the product was precipitated from the aqueous layer by adjusting to pH 3-4 with 1M HCl. After cooling to 4° C., the product was filtered, washed with water (3×1 mL), and dried in vacuo to afford the title compound (24.6 mg, 64%) as a light green solid. $^1$H NMR (500 MHz, DMSO-d$_6$) δ 13.96 (bs, 1H), 13.78 (bs, 1H), 9.22 (dd, J=1.0, 2.0 Hz, 1H), 8.48 (dd, J=2.0, 8.5 Hz, 1H), 8.23 (dd, J=1.0, 8.5 Hz, 1H), 8.16 (s, 1H); $^{13}$C NMR (125 MHz, DMSO-d$_6$) δ 166.1, 161.6, 158.9, 151.2, 147.9, 144.6, 139.1, 135.7, 128.4, 123.3; HRMS (ESI) m/z 233.0203 [calc'd for C$_{10}$H$_5$N$_2$O$_5$ (M−H)$^-$ 233.0203].

2-(4-Carboxyoxazol-2-yl)pyridine-5-carboxylic Acid

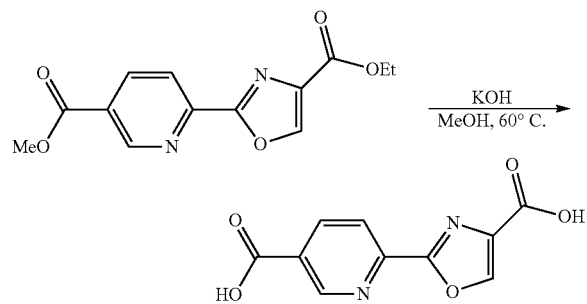

Procedure:

Methyl 2-(4-ethoxycarbonyloxazol-2-yl)-pyridine-5-carboxylate (50 mg, 0.18 mmoles) and KOH (46.7 mg, 0.72 mmoles) were added to a vial. MeOH (5.0 mL) was added to the vial and the reaction mixture was heated to 60° C. with stirring until the starting material was completely consumed, as judged by TLC. The reaction mixture was cooled and concentrated under reduced pressure, after which the crude product was dissolved in water (2 mL). The aqueous layer was washed with EtOAc (1×2 mL), after which the product was precipitated from the aqueous layer by adjusting to pH 3-4 with 1M HCl. After cooling to 4° C., the product was filtered, washed with water (3×1 mL), and dried in vacuo to afford the title compound (30 mg, 71%) as a white solid. $^1$H NMR (500 MHz, DMSO-d$_6$) δ 13.72 (bs, 1H), 13.40 (bs, 1H), 9.19 (dd, J=0.5, 2.0 Hz, 1H), 9.02 (s, 1H), 8.47 (dd J=2.0, 8.5 Hz, 1H), 8.28 (dd, J=0.5, 8.5 Hz, 1H); $^{13}$C NMR (125 MHz, DMSO-d$_6$) δ 166.1, 162.2, 160.1, 151.1, 148.0, 147.4, 139.1, 135.4, 128.2, 122.8; HRMS (ESI) m/z 233.0195 [calc'd for C$_{10}$H$_5$N$_2$O$_5$ (M−H)$^-$ 233.0203].

2-(5-Carboxy-1-methyl-1H-imidazol-2-yl)pyridine-5-carboxylic Acid

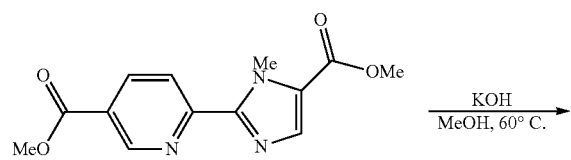

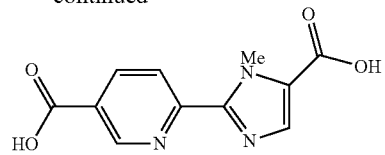

Procedure:

Methyl 2-(5-methoxycarbonyl-1-methyl-1H-imidazol-2-yl)pyridine-5-carboxylate (30 mg, 0.11 mmoles) and KOH (28 mg, 0.44 mmoles) were added to a vial. MeOH (3 mL) was added to the vial and the reaction mixture was heated to 60° C. with stirring until the starting material was completely consumed, as judged by TLC. The reaction mixture was cooled and concentrated under reduced pressure, after which the crude product was dissolved in water (2 mL). The aqueous layer was washed with EtOAc (1×2 mL), after which the product was precipitated from the aqueous layer by adjusting to pH 3-4 with 1M HCl. After cooling to 4° C., the product was filtered, washed with water (3×1 mL), and dried in vacuo to afford the title compound (16 mg, 58%) as a pale yellow solid. $^1$H NMR (500 MHz, DMSO-d$_6$) δ 13.49 (bs, 1H), 13.2 (bs, 1H), 9.16 (d, J=2.0 Hz, 1H), 8.41 (dd, J=2.0, 8.5 Hz, 1H), 8.25 (d, J=8.5 Hz, 1H), 7.79 (s, 1H), 4.33 (s, 3H); $^{13}$C NMR (125 MHz, DMSO-d$_6$) δ 166.4, 161.7, 153.1, 149.9, 148.0, 138.5, 137.2, 126.7, 126.3, 124.3, 35.1; HRMS (EI) m/z 247.0583 [calc'd for C$_{11}$H$_9$N$_3$O$_4$ (M)$^+$ 247.0588].

2-(5-Carboxypyridin-2-yl)pyrazine-5-carboxylic Acid

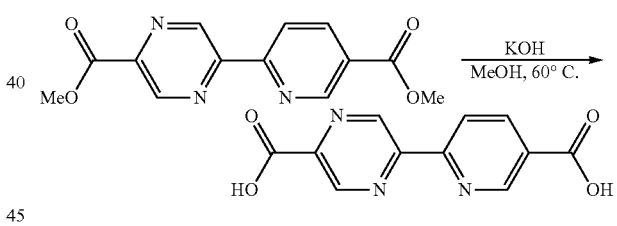

Procedure:

Methyl 2-(5-methoxycarbonylpyridin-2-yl)pyrazine-5-carboxylate (28 mg, 0.10 mmoles) and KOH (26 mg, 0.41 mmoles) were added to a vial. MeOH (3 mL) was added to the vial and the reaction mixture was heated to 60° C. with stirring until the starting material was completely consumed, as judged by TLC. The reaction mixture was cooled and concentrated under reduced pressure. The crude product was dissolved in water (2 mL). The aqueous layer was washed with EtOAc (1×2 mL), after which the product was precipitated from the aqueous layer by adjusting to pH 3-4 with 1M HCl. After cooling to 4° C., the product was filtered, washed with water (3×1 mL), and dried in vacuo to afford the title compound (17 mg, 68%) as a light brown solid. $^1$H NMR (500 MHz, DMSO-d$_6$) δ 13.84 (bs, 2H), 9.69 (d, J=1.5 Hz, 1H), 9.30 (d, J=1.0 Hz, 1H), 9.25 (dd, J=0.5, 2.0 Hz, 1H), 8.54 (d, J=7.5 Hz, 1H), 8.50 (dd, J=2.0, 8.0 Hz, 1H); $^{13}$C NMR (125 MHz, DMSO-d$_6$) δ 168.8, 165.9, 156.8, 152.1, 151.4, 146.0, 145.3, 143.3, 139.7, 128.7, 122.7; HRMS (ESI) m/z 246.0505 [calc'd for C$_{11}$H$_8$N$_3$O$_4$ (M+H)$^+$ 246.0510].

6-(5-Carboxypyridin-2-yl)pyridazine-3-carboxylic Acid

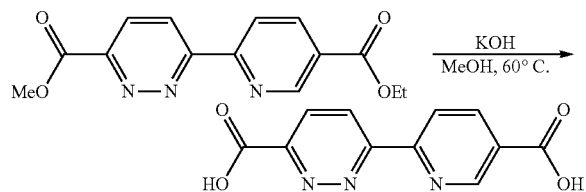

Procedure:

Methyl 6-(5-ethoxycarbonylpyridin-2-yl)pyridazine-3-carboxylate (37 mg, 0.13 mmoles) and KOH (34 mg, 0.52 mmoles) were added to a vial. MeOH (1.3 mL) was added to the vial and the reaction mixture was heated to 60° C. with stirring until the starting material was completely consumed, as judged by TLC. The reaction mixture was cooled and concentrated under reduced pressure. The crude product was dissolved in water (2 mL). The aqueous layer was washed with EtOAc (1×2 mL), after which the product was precipitated from the aqueous layer by adjusting to pH 3-4 with 1M HCl. After cooling to 4° C., the product was filtered, washed with water (3×1 mL), and dried in vacuo to afford the title compound (23 mg, 73%) as a pale yellow solid. $^1$H NMR (500 MHz, DMSO-$d_6$) δ 13.73 (bs, 2H), 9.11 (dd, J=1.0, 2.0 Hz, 1H), 8.63 (dd, J=1.0, 8.5 Hz, 1H), 8.60 (d, J=9.0 Hz, 1H), 8.40 (dd, J=2.0, 8.5 Hz, 1H), 8.24 (d, J=9.0 Hz, 1H); $^{13}$C NMR (125 MHz, DMSO-$d_6$) δ 166.2, 165.3, 158.8, 155.7, 152.5, 150.9, 139.1, 129.2, 128.2, 126.0, 121.9; HRMS (ESI) m/z 246.0517 [calc'd for $C_{11}H_8N_3O_4$ (M+H)$^+$ 246.0510].

2-(4-Carboxy-1H-pyrrol-2-yl)pyridine-5-carboxylic Acid

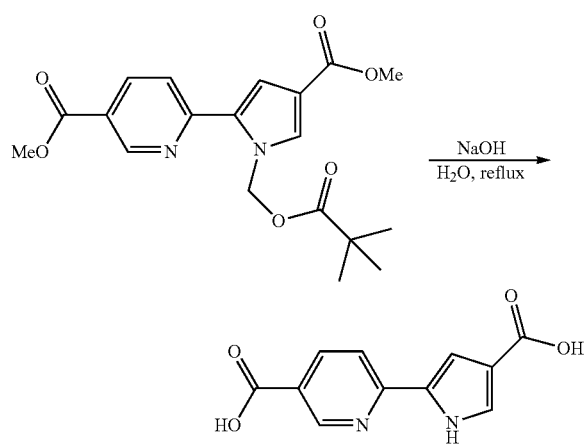

Procedure:

Methyl 2-(4-methoxycarbonyl-1-pivaloyloxymethyl-1H-pyrrol-2-yl)pyridine-5-carboxylate (28 mg, 0.075 mmoles) and 2 M NaOH (1.0 mL) were added to a vial. The reaction mixture was heated to reflux with stirring until the starting material was completely consumed, as judged by TLC. The reaction mixture was cooled and concentrated under reduced pressure. The crude product was dissolved in water (2 mL). The aqueous layer was washed with EtOAc (1×2 mL), after which the product was precipitated from the aqueous layer by adjusting to pH 3-4 with 1M HCl. After cooling to 4° C., the product was filtered, washed with water (3×1 mL), and dried in vacuo to afford the title compound (20 mg, 78%) as a grey solid. $^1$H NMR (500 MHz, DMSO-$d_6$) δ 13.23 (bs, 1H), 12.30 (s, 1H), 12.13, (bs, 1H), 9.00 (dd, J=1.0, 2.5 Hz, 1H), 8.21 (dd, J=2.5, 8.5 Hz, 1H), 7.91 (d, J=8.5 Hz, 1H), 7.46 (dd, J=2.5, 3.5 Hz, 1H), 7.26 (dd, J=1.5, 2.5 Hz, 1H); $^{13}$C NMR (125 MHz, DMSO-$d_6$) δ 169.3, 168.4, 156.1, 153.3, 140.8, 134.7, 129.9, 126.8, 121.1 (2 signals), 114.0; HRMS (EI) m/z 232.0474 [calc'd for $C_{11}H_8N_2O_4$ (M)$^+$ 232.0479].

2-(5-Carboxy-1H-pyrazol-3-yl)pyridine-5-carboxylic Acid

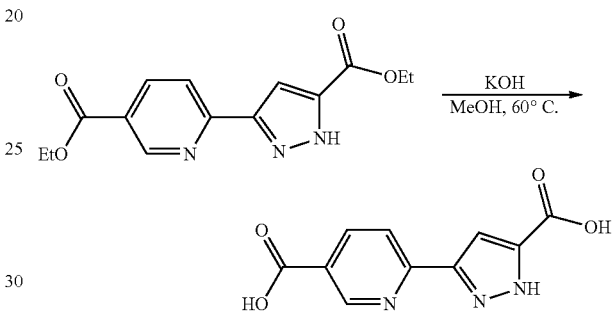

Procedure:

Ethyl 2-(5-ethoxycarbonyl-1H-pyrazol-3-yl)pyridine-5-carboxylate (78 mg, 0.27 mmoles) and KOH (70 mg, 1.08 mmoles) were added to a vial. MeOH (2.7 mL) was added to the vial and the reaction mixture was heated to 60° C. with stirring until the starting material was completely consumed, as judged by TLC. The reaction mixture was cooled and concentrated under reduced pressure. The crude product was dissolved in water (4 mL). The aqueous layer was washed with EtOAc (1×4 mL), after which the product was precipitated from the aqueous layer by adjusting to pH 3-4 with 1M HCl. After cooling to 4° C., the product was filtered, washed with water (3×2 mL), and dried in vacuo to afford the title compound (45 mg, 72%) as a pale yellow solid.

Dimethyl 2,2'-bipyridine-5,5'-dicarboxylate

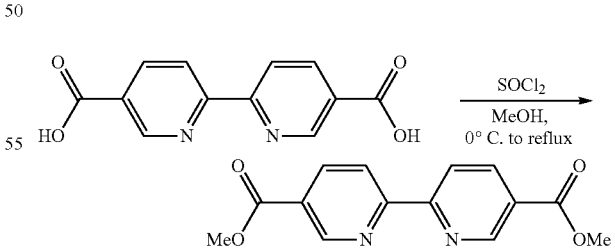

Procedure:

Bipy55'DC (200 mg, 0.82 mmoles) and MeOH (13 mL) were added to a dried flask and stirred on ice. Thionyl chloride (1.3 mL) was added dropwise on ice, after which the flask was fitted with a reflux condenser and heated at reflux. After 24 hr, the reaction was cooled on ice and quenched by the dropwise addition of saturated NaHCO$_3$ (20 mL). The aqueous layer was extracted with CHCl$_3$ (3×30 mL) and the combined organics were washed with saturated NaHCO$_3$ (1×30 mL), dried over Na$_2$SO$_4$(s), and concentrated under reduced pressure. The crude product was then purified by chromatography on silica (25-90% EtOAc in hexanes) and recrystallized from CHCl$_3$ to afford the title compound (56 mg, 25%) as a pale yellow crystalline solid. $^1$H NMR (500 MHz, CDCl$_3$) δ9.32 (s, 1H), 8.61 (d, J=8.0 Hz, 1H), 8.47 (dd, J=1.5, 8.0 Hz, 1H), 4.02 (s, 3H); $^{13}$C NMR (125 MHz, CDCl$_3$) δ 165.7, 158.3, 150.6, 138.2, 129.3, 121.4, 52.6; HRMS (ESI) m/z 273.0863 [calc'd for C$_{14}$H$_{13}$N$_2$O$_4$ (M+H)$^+$ 273.0870].

Diethyl 2,2'-bipyridine-5,5'-dicarboxylate

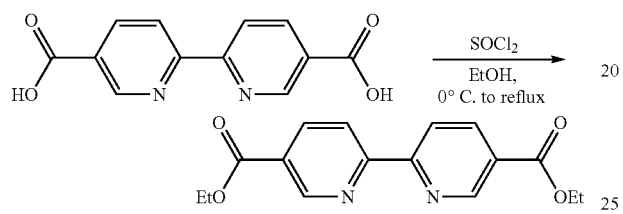

Procedure:

Bipy55'DC (200 mg, 0.82 mmoles) and EtOH (13 mL) were added to a dried flask and stirred on ice. Thionyl chloride (1.3 mL) was added dropwise on ice, after which the flask was fitted with a reflux condenser and heated at reflux. After 24 hr, the reaction was cooled on ice and quenched by the dropwise addition of saturated Na$_2$CO$_3$ (20 mL). The aqueous layer was extracted with CH$_2$Cl$_2$ (4×20 mL) and the combined organics were dried over Na$_2$SO$_4$(s), and concentrated under reduced pressure. The crude product was then purified by chromatography on silica (3% acetone in 1:1 DCM/hexanes) to afford the title compound (190 mg, 77%) as a white solid. $^1$H NMR (500 MHz, CDCl$_3$) δ 9.32 (dd, J=0.5, 2.0 Hz, 1H), 8.59 (dd, J=0.5, 8.5 Hz, 1H), 8.46 (dd, J=2.0, 8.5 Hz, 1H), 4.47 (q, J=7.5 Hz, 2H), 1.46 (t, J=7.5 Hz, 3H); $^{13}$C NMR (125 MHz, CDCl$_3$) δ 165.2, 158.3, 150.6, 138.1, 126.6, 121.3, 61.6, 14.3; HRMS (ESI) m/z 301.1193 [calc'd for C$_{16}$H$_{17}$N$_2$O$_4$ (M+H)$^+$ 301.1183].

Diethyl 2,2'-bipyridine-4,5'-dicarboxylate

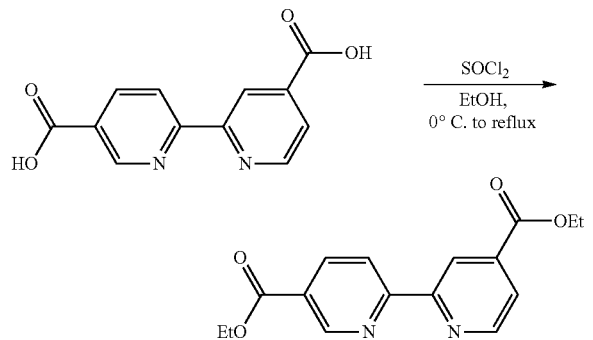

Procedure:

Bipy45'DC (200 mg, 0.82 mmoles) and EtOH (13 mL) were added to a dried flask and stirred on ice. Thionyl chloride (1.3 mL) was added dropwise on ice, after which the flask was fitted with a reflux condenser and heated at reflux. After 24 hr, the reaction was cooled on ice and quenched by the dropwise addition of saturated Na$_2$CO$_3$ (20 mL). The aqueous layer was extracted with CH$_2$Cl$_2$ (4×20 mL) and the combined organics were dried over Na$_2$SO$_4$(s), and concentrated under reduced pressure. The crude product was then purified by chromatography on silica (3% acetone in 1:1 DCM/hexanes) to afford the title compound (189 mg, 77%) as a white solid. $^1$H NMR (400 MHz, CDCl$_3$) δ9.28 (dd, J=1.2, 2.0 Hz, 1H), 8.96 (dd, J=0.5, 1.2 Hz, 1H), 8.81 (dd, J=0.5, 5.2 Hz, 1H), 8.48 (dd, J=0.5, 8.0 Hz, 1H), 8.39 (dd, J=2.0, 8.0 Hz, 1H), 7.89 (dd, J=1.6, 5.2 Hz, 1H), 4.44 (q, J=7.2 Hz, 2H), 4.42 (q, J=7.2 Hz, 2H), 1.43 (t, J=7.2 Hz, 3H), 1.42 (t, J=7.2 Hz, 3H); $^{13}$C NMR (100 MHz, CDCl$_3$) δ165.1, 165.0, 158.5, 156.2, 150.5, 150.0, 138.9, 137.96, 126.2, 123.5, 121.0, 120.6, 61.9, 61.4, 14.3 (2 signals); HRMS (ESI) m/z 301.1183 [calc'd for C$_{16}$H$_{17}$N$_2$O$_4$ (M+H)$^+$ 301.1183].

Ethyl 2-(5-ethoxycarbonylthiazol-2-yl)pyridine-5-carboxylate

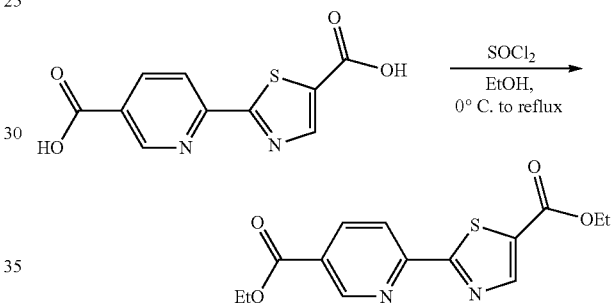

Procedure:

2-(5-Carboxythiazol-2-yl)pyridine-5-carboxylic acid (38 mg, 0.15 mmoles) and EtOH (7 mL) were added to a dried flask and stirred on ice. Thionyl chloride (300 μL) was added dropwise on ice, after which the flask was fitted with a reflux condenser and heated at reflux. After 24 hr, the reaction was cooled on ice and quenched by the dropwise addition of saturated Na$_2$CO$_3$ (10 mL). The aqueous layer was extracted with CH$_2$Cl$_2$ (3×10 mL) and the combined organics were dried over Na$_2$SO$_4$(s) and concentrated under reduced pressure. The crude product was then purified by chromatography on silica (2% acetone in 1:1 DCM/hexanes) to afford the title compound (40 mg, 86%) as a pale yellow solid. $^1$H NMR (400 MHz, CDCl$_3$) δ9.22 (dd, J=0.8, 2.0 Hz, 1H), 8.5 (s, 1H), 8.43 (dd, J=2.0, 8.4 Hz, 1H), 8.29 (dd, J=0.8, 8.4 Hz, 1H), 4.48-4.39 (m, 4H), 1.46-1.40 (m, 6H); $^{13}$C NMR (100 MHz, CDCl$_3$) δ172.6, 164.6, 161.3, 153.6, 150.9, 149.5, 138.3, 132.1, 127.4, 119.5, 61.8, 61.7, 14.27 (2 signals); HRMS (ESI) m/z 307.0752 [calc'd for C$_{14}$H$_{15}$N$_2$O$_4$S (M+H)$^+$ 307.0748].

Dimethyl 2,5-pyridinedicarboxylate

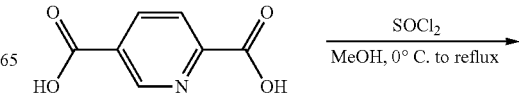

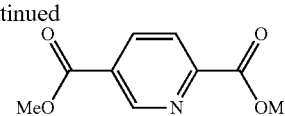

Procedure:

Thionyl chloride (2.2 mL) was added dropwise to MeOH (14 mL) while stirring on ice. 2,5-Pyridinedicarboxylic acid (1.0 g, 6.0 mmoles) was added and the reaction heated at reflux for 3 hr. The reaction was cooled and the solvent removed under reduced pressure. The resulting residue was dissolved in DCM (15 mL), after which saturated $Na_2CO_3$ (15 mL) was added while stirring on ice. The aqueous layer was extracted with DCM (3×15 mL), and the combined organics were washed with saturated $Na_2CO_3$ (2×40 mL), dried over $Na_2SO_4$(s), and concentrated under reduced pressure to afford the title compound (915 mg, 78%) as a pale yellow solid. $^1$H NMR (500 MHz, $CDCl_3$) δ9.32 (dd, J=0.5, 2.0 Hz, 1H), 8.47 (dd, J=2.0, 8.0 Hz, 1H), 8.23 (dd, J=0.5, 8.0 Hz, 1H), 4.06 (s, 3H), 4.01 (s, 3H); $^{13}$C NMR (125 MHz, $CDCl_3$) δ165.0, 164.9, 150.8, 150.8, 138.4, 128.6, 124.7, 53.3, 52.8; HRMS (ESI) m/z 196.0600 [calc'd for $C_9H_{10}NO_4$ (M+H)$^+$ 196.0605].

Methyl 6-formylnicotinate

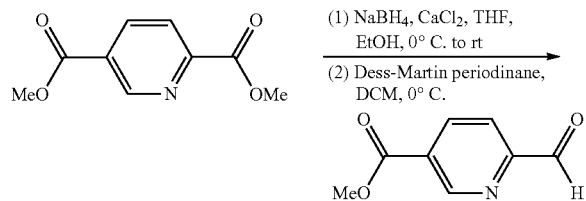

Procedure:

Dimethyl-2,5-pyridinedicarboxylate (960 mg, 4.9 mmoles) and $CaCl_2$ (2.198 g, 19.7 mmoles) were added to a dried flask. THF (11 mL) and EtOH (12 mL) were added, and the resulting suspension was stirred on ice for 30 minutes. $NaBH_4$ (465 mg, 12.3 mmoles) was added portion wise with stirring. The reaction was allowed to come to room temperature overnight. After 18 h, the reaction was quenched by the dropwise addition of an aqueous solution of $NH_4Cl$ (saturated aqueous $NH_4Cl$ [20 mL] plus $H_2O$ [40 mL]) while stirring on ice. The aqueous layer was extracted with DCM (4×30 mL) and the combined organics were dried over $Na_2SO_4$(s) and concentrated under reduced pressure to afford the crude alcohol (678 mg) as a pale yellow solid. The crude alcohol was dissolved in dry DCM (45 mL), after which Dess-Martin periodinane (2.6 g, 6.1 mmoles) was added portion wise while stirring on ice. After 6 h, the reaction was quenched by the dropwise addition of a solution of 5% $Na_2S_2O_3$ in half saturated $NaHCO_3$ (80 mL). The aqueous layer was extracted with DCM (3×40 mL). The combined organics were dried over $Na_2SO_4$(s) and concentrated under reduced pressure to afford the title compound (504 mg, 62%) as a pale yellow solid. $^1$H NMR (400 MHz, $CDCl_3$) δ10.16 (s, 1H), 9.38 (dd, J=0.5, 2.0 Hz, 1H), 8.49 (dd, J=2.0, 8.0 Hz, 1H), 8.05 (dd, J=0.5, 8.0 Hz, 1H), 4.02 (s, 1H); $^{13}$C NMR (100 MHz, $CDCl_3$) δ192.6, 164.8, 154.9, 151.2, 138.3, 121.1, 52.9; HRMS (EI) m/z 165.0415 [calc'd for $C_8H_7NO_3$ (M$^+$) 165.0421]

Methyl 2-(5-trifluoromethyl-1H-imidazol-2-yl)pyridine-5-carboxylate

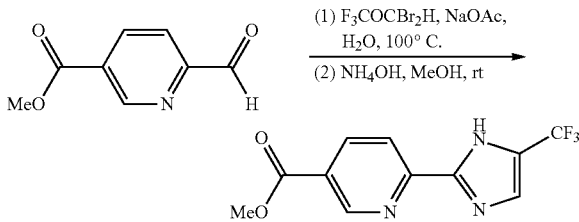

Procedure:

NaOAc (277 mg, 3.4 mmoles) and 2,2-dibromo-1,1,1-trifluoroacetone (454 mg, 1.7 mmoles) were dissolved in $H_2O$ (770 μL) and stirred at 100° C. for 30 min. The reaction was cooled to room temperature, after which a solution of methyl 6-formylnicotinate (250 mg, 1.5 mmoles) and concentrated $NH_4OH$ (1.5 mL) in MeOH (4.6 mL), was added dropwise while stirring. The reaction was stirred overnight, after which the solvent was removed under reduced pressure. $CHCl_3$ (25 mL) and 10% $NaHCO_3$ (25 mL) were added to the residue. The aqueous layer was extracted with $CHCl_3$ (2×25 mL), and the combined organics were dried over $Na_2SO_4$(s) and concentrated under reduced pressure. The crude product was then purified by chromatography on silica (25% EtOAc in hexanes) and recrystallized from 1:1 hexanes/EtOAc to afford the title compound (128 mg, 47%) as a pale yellow crystalline solid. $^1$H NMR (500 MHz, $CD_3OD$) δ9.13 (dd, J=1.0, 2.0 Hz, 1H), 8.38 (dd, J=2.0, 8.5 Hz, 1H), 8.15 (dd, J=1.0, 8.5 Hz, 1H), 7.72 (d, J=1.0 Hz, 1H), 3.96 (s, 3H); $^{13}$C NMR (125 MHz, $CD_3OD$) δ 165.2, 150.5, 150.2, 146.7, 137.9, 132.6 (q, J=155 Hz), 125.7, 121.7 (q, J=1059 Hz), 119.3, 119.1, 51.6; HRMS (ESI) m/z 272.0630 [calc'd for $C_{11}H_9F_3N_3O_2$ (M+H)$^+$ 272.0642].

2-(5-Methoxycarbonyl-1-H-imidazol-2-yl)pyridine-5-carboxylic Acid

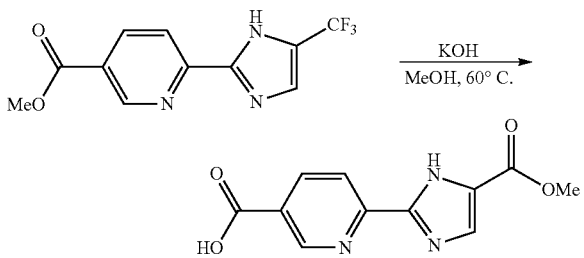

Procedure:

Methyl 2-(5-trifluoromethyl-1H-imidazol-2-yl)pyridine-5-carboxylate (103 mg, 0.38 mmoles) and KOH (147 mg, 2.28 mmoles) were added to a vial. MeOH (11 mL) was added to the vial and the reaction mixture was heated to 60° C. until the starting material was completely consumed, as judged by TLC. The reaction mixture was cooled and concentrated under reduced pressure. The crude product was dissolved in water (3 mL). The aqueous layer was washed with EtOAc (1×3 mL), after which the product was precipitated from the aqueous layer by adjusting to pH 3-4 with 1M HCl. After cooling to 4° C., the product was filtered, washed with water (3×1 mL), and dried in vacuo to afford the title compound (84 mg, 94%) as a white solid. $^1$H NMR (500 MHz, DMSO-$d_6$) δ13.74 (s, 1H), 13.56 (s, 1H), 9.12 (d, J=2.0 Hz, 1H), 8.40 (dd, J=2.0, 8.0 Hz, 1H), 8.22 (d, J=8.0 Hz, 1H), 7.99 (d, J=2.5 Hz, 1H), 3.81 (s, 3H); $^{13}$C NMR (125 MHz, DMSO-$d_6$) δ166.4, 163.1, 151.4, 150.5, 146.4, 138.9, 134.2, 126.6 (2 signals), 120.3, 51.7; HRMS (ESI) m/z 248.0671 [calc'd for $C_{11}H_{10}N_3O_4$ (M+H)$^+$ 248.0666].

2-(5-Carboxy-1-H-imidazol-2-yl)pyridine-5-carboxylic Acid

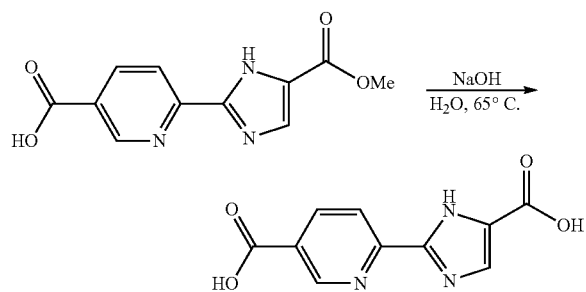

Procedure:
2-(5-Methoxycarbonyl-1H-imidazol-2-yl)pyridine-5-carboxylic acid (50 mg, 0.20 mmoles), 1M NaOH (400 µL), and water (3.6 mL) were added to a vial. The reaction mixture was heated to 65° C. with stirring. After 24 hr, the reaction mixture was cooled and washed with EtOAc (1×3 mL), after which the product was precipitated from the aqueous layer by adjusting to pH 3-4 with 1M HCl. After cooling to 4° C., the product was filtered, washed with water (3×1 mL), and dried in vacuo to afford the title compound (44 mg, 93%) as a pale yellow solid. $^1$H NMR (500 MHz, DMSO-$d_6$) δ13.62 (s, 1H), 13.30 (bs, 1H), 12.74 (bs, 1H), 9.11 (dd, J=0.5, 1.0 Hz, 1H), 8.39 (dd, J=2.0, 8.5 Hz, 1H), 8.20 (d, J=8.0 Hz, 1H), 7.88 (d, J=2.5 Hz, 1H); $^{13}$C NMR (125 MHz, DMSO-$d_6$) δ166.4, 164.0, 151.5, 150.5, 146.1, 138.9, 135.3, 126.5, 126.2, 120.2; HRMS (EI) m/z 233.0432 [calc'd for $C_{10}H_7N_3O_4$ (M)$^+$ 233.18].

Methyl 2-(5-methoxycarbonyl-1H-imidazol-2-yl)pyridine-5-carboxylate

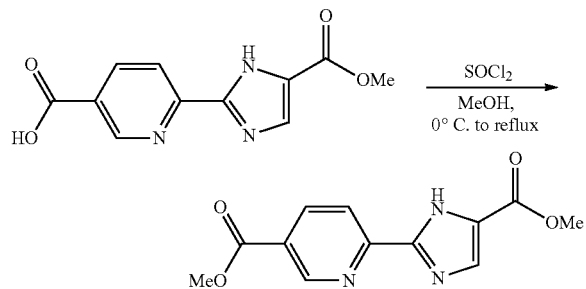

Procedure:
2-(5-Methoxycarbonyl-1H-imidazol-2-yl)pyridine-5-carboxylic acid (100 mg, 0.41 mmoles) and MeOH (7.0 mL) was added to a round bottom flask and stirred on ice. Thionyl chloride (750 µL) was added dropwise on ice, after which the flask was fitted with a reflux condenser and heated at reflux. After 24 hr, the reaction was cooled on ice and quenched by the dropwise addition of saturated $Na_2CO_3$ (20 mL). The aqueous layer was extracted with $CH_2Cl_2$ (5×20 mL) and the combined organics were dried over $Na_2SO_4$(s), and concentrated under reduced pressure. The crude product was then purified by chromatography on silica (50% EtOAc in hexanes), to afford a pale yellow solid. The solid was dissolved in minimal DCM, precipitated by the dropwise addition of cold hexanes, and filtered in vacuo to afford the title compound (50 mg, 48%) as a white solid. $^1$H NMR (500 MHz, CDCl$_3$, ~5:2 ratio of 2 tautomers) δ 11.01 (bs, 1.4H), 9.18-9.15 (m, 1.4H), 8.44-8.38 (m, 2.4H), 8.29 (d, J=8 Hz, 0.4H), 7.91 (s, 1H), 7.84 (s, 0.4H), 3.99-3.94 (m, 8.4H); $^{13}$C NMR (125 MHz, CDCl$_3$, ~5:2 ratio of 2 tautomers) δ 165.3 (2 signals), 163.2, 160.2, 150.7, 150.4 (2 signals), 150.3, 147.8, 146.2, 138.4 (2 signals), 136.7, 135.4, 126.1, 125.9, 124.3 (2 signals), 120.2, 120.0, 52.6 (2 signals), 52.1 (2 signals); HRMS (ESI) m/z 262.0829 [calc'd for $C_{12}H_{12}N_3O_4$ (M+H)$^+$ 262.0823].

Ethyl 2-(5-ethoxycarbonyl-1H-imidazol-2-yl)pyridine-5-carboxylate

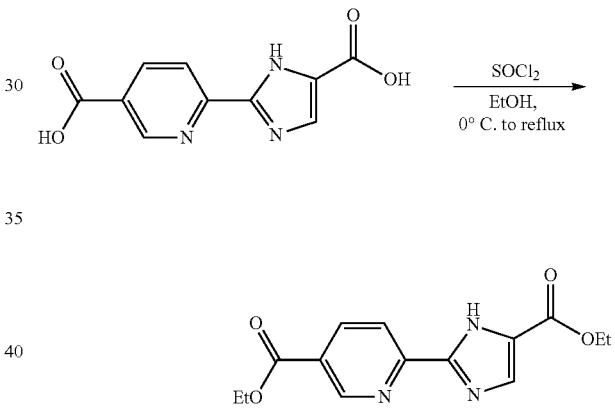

Procedure:
2-(5-Carboxy-1H-imidazol-2-yl)pyridine-5-carboxylic acid (85 mg, 0.36 mmoles) and EtOH (6.3 mL) were added to a round bottom flask and stirred on ice. Thionyl chloride (710 µL) was added dropwise on ice, after which the flask was fitted with a reflux condenser and heated at reflux. After 24 hr, the reaction was cooled on ice and quenched by the dropwise addition of saturated $Na_2CO_3$ (10 mL). The aqueous layer was extracted with $CH_2Cl_2$ (6×10 mL) and the combined organics were dried over $Na_2SO_4$(s) and concentrated under reduced pressure. The crude product was then purified by chromatography on silica (2% MeOH in 1:1 DCM/hexanes) to afford the title compound (95 mg, 90%) as a pale yellow solid. $^1$H NMR (500 MHz, CDCl$_3$, ~5:4 ratio of two tautomers) δ11.16 (bs, 1H), 11.02 (bs, 0.8H), 9.19 (dd, J=1.0, 2.0 Hz, 0.8H); 9.15-9.14 (m, 1H), 8.44-8.38 (m, 2.8H), 8.28 (dd, J=1.0, 8.0 Hz, 0.8H), 7.90-7.86 (m, 1.8H), 4.48-4.38 (m, 7.2H), 1.46-1.39 (m, 10.8H); $^{13}$C NMR (125 MHz, CDCl$_3$) δ164.9, 164.8 162.8, 159.8, 150.7, 150.4 (2 signals), 150.3, 147.8, 146.3, 138.4, 138.3, 136.5, 135.7, 126.3, 126.1, 124.7, 124.1, 120.1, 120.0, 61.7 (2 signals), 61.3, 61.0, 14.5, 14.4, 14.3 (2 signals); HRMS (ESI) m/z 290.1136 [calc'd for $C_{14}H_{16}N_3O_4$ (M+H)$^+$ 290.1132].

N-(Methoxyoxalyl)glycine ethyl ester

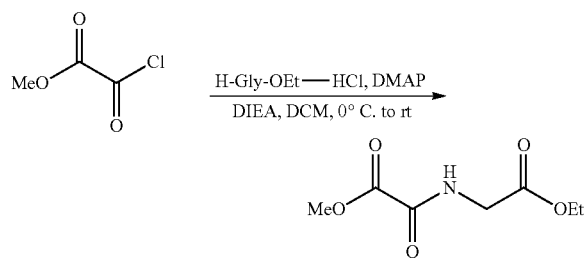

Procedure for:

HGlyOEt.HCl (333 mg, 2.4 mmoles) and DMAP (29.1 mg, 0.24 mmoles) were added to a dried flask. The flask was capped with a septum and purged with nitrogen (~5 times). DCM (6 mL) was added and the reaction was cooled in an ice bath. DIEA (750 μL, 4.3 mmoles) and monomethyl oxalyl chloride (200 μL, 2.2 mmoles) were added via syringe, and the reaction was stirred and allowed to come to room temperature. After 6 hr, the reaction was quenched on ice by the dropwise addition of saturated ammonium chloride (10 mL). The organic layer was collected, and the aqueous layer was extracted with EtOAc (3×10 mL). The combined organic extracts were dried over $Na_2SO_4$(s), and concentrated under reduced pressure to afford a crude yellow oil. The crude product was then purified by chromatography on silica (70% EtOAc in hexanes) to afford the title compound (416 mg, 92%) as a white solid. $^1$H NMR (400 MHz, $CDCl_3$) δ7.65 (bs, 1H), 4.23 (q, J=7.2 Hz, 2H), 4.11 (d, J=5.6 Hz, 2H), 3.90 (s, 3H), 1.28 (t, J=7.2 Hz, 3H); $^{13}$C NMR (100 MHz, $CDCl_3$) δ168.6, 160.4, 156.4, 61.9, 53.7, 41.5, 14.1; HRMS (ESI) m/z 212.0535 [calc'd for $C_7H_{11}NO_5Na$ $(M+Na)^+$ 212.0530].

N-Oxalylglycine

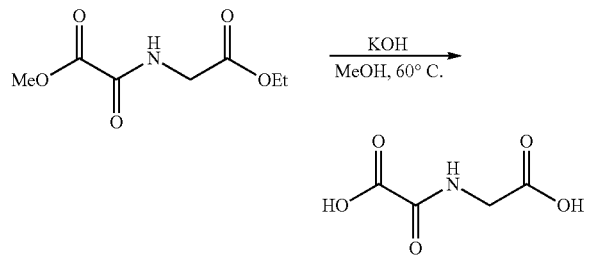

Preparation:

N-(Methoxyoxalyl)glycine ethyl ester (100 mg, 0.53 mmoles) and KOH (88 mg, 1.6 mmoles) were added to a vial. MeOH (5.0 mL) was added to the vial and the reaction mixture was heated to 60° C. with stirring until the starting material was completely consumed, as judged by TLC. The reaction mixture was cooled and concentrated under reduced pressure. The crude product was dissolved in water (2 mL), and the pH adjusted to 3-4 with 1M HCl. The aqueous solution was concentrated under reduced pressure and the residue dissolved in boiling EtOAc. The solution was cooled, filtered, and concentrated under reduced pressure to a viscous oil. The oil was dissolved in a minimal amount of DCM, diluted with Hexanes, and concentrated under reduced pressure. This procedure was repeated 3 times, after which the product was dried in vacuo to afford the title compound (77 mg, 99%) as a white solid. $^1$H NMR (500 MHz, DMSO-$d_6$) δ14.03 (bs, 1H), 12.76 (bs, 1H), 9.04 (t, J=6.0 Hz, 1H), 3.79 (d, J=6.5 Hz, 2H); $^{13}$C NMR (125 MHz, DMSO-$d_6$) δ170.8, 162.1, 158.9, 41.4; HRMS (ESI) m/z 165.0506 [calc'd for $C_4H_9N_2O_2$ $(M+NH_4)^+$ 165.0506].

N-Benzyloxycarbonyl-(2S)-prolyl-(2S)-prolylglycine ethyl ester (CbzProProGlyOEt)

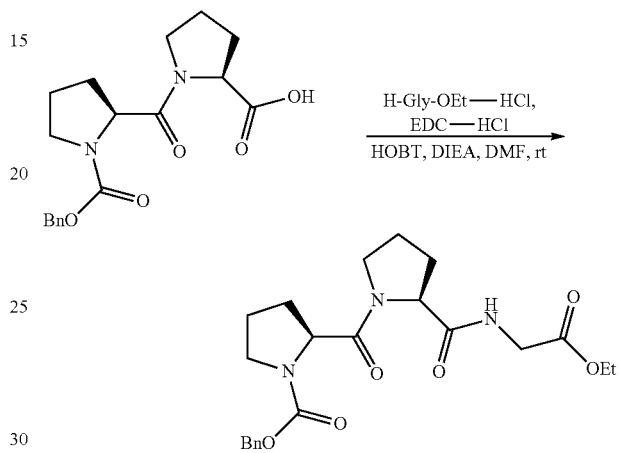

Procedure:

N-Benzyloxycarbonyl-(2S)-prolyl-(2S)-proline (CbzProProOH, 967 mg, 2.8 mmoles), HGlyOEt.HCl (428 mg, 3.1 mmoles), EDC.HCl (590 mg, 3.1 mmoles), and HOBT (415 mg, 3.1 mmoles) were added to a dried flask. The flask was capped with a septum and purged with nitrogen (~5 times). DMF (28 mL) and DIEA (1.9 mL, 11.2 mmoles) were added via syringe, and the reaction was stirred at room temperature until the reaction was judged to be complete by TLC (approximately 48 hr). The reaction was concentrated under reduced pressure, and the resulting residue was dissolved in EtOAc (50 mL). The organic layer was washed with 5% w/v $KHCO_3$ (2×25 mL), 5% w/v $KHSO_4$ (2×25 mL), and brine (1×25 mL). The combined organics were dried over $Na_2SO_4$(s) and concentrated under reduced pressure to a crude yellow oil. The crude product was then purified by chromatography on silica (0-2% MeOH in EtOAc) to yield the title compound (755 mg, 63%) as a pale yellow oil. $^1$H NMR (400 MHz, $CDCl_3$, mixture of 3 or more rotamers, integrations are approximate) δ8.29 (t, J=6.0 Hz, 0.7H), 7.40-7.20 (m, 15.4H+$CHCl_3$), 7.15-7.11 (m, 0.4H), 5.94 (t, J=6.0 Hz, 0.1H), 5.31 (d, J=12.4 Hz, 0.1H), 5.18-4.93 (m, 5.0H), 4.77 (d, J=12.4 Hz, 0.1H), 4.69 (app dd, J=2.4, 8.0 Hz, 1.0H), 4.54 (app dd, J=4.0, 4.0 Hz, 1.0H), 4.49-4.20 (m, 3.4H), 4.17-3.80 (m, 10.4H), 3.76-3.39 (m, 10.0H), 3.31-3.23 (m, 0.9H), 2.99 (app dd, J=6.0, 17.6 Hz, 0.1H), 2.53 (app dd, J=5.6, 12.4 Hz, 0.7H), 2.35-1.65 (m, 21.4H), 1.44-1.01 (m, 9.6H); $^{13}$C NMR (100 MHz, $CDCl_3$, mixture of 3 or more rotamers) δ172.9, 172.5, 171.7, 171.6, 171.5, 171.4, 171.3, 169.7, 169.6, 169.3, 168.7, 155.2, 154.9, 154.0, 136.7, 136.5 (multiple signals), 129.0, 128.8, 128.6, 128.4 (multiple signals), 128.1 (2 signals), 127.9 (2 signals), 127.7 (multiple signals), 125.3, 67.3, 67.2, 67.1, 66.9, 61.2 (multiple signals), 61.1, 61.0, 59.7, 59.4, 58.5, 58.3 (multiple signals), 57.4, 47.7, 47.3 (2 signals), 47.1 (multiple signals), 46.9

(multiple signals), 46.7 (multiple signals), 41.5, 41.2, 40.5, 33.9, 31.2, 31.8, 30.4 (multiple signals), 29.4 (2 signals), 26.9, 26.5 (multiple signals), 25.7, 25.2 (multiple signals), 25.0, 24.7, 24.3, 23.7, 23.4, 22.1, 22.0, 14.1 (2 signals); HRMS (ESI) m/z 449.2374 [calc'd for $C_{22}H_{29}N_3O_6Na$ (M+Na)$^+$ 449.2395].

N-Dansylglycyl-(2S)-prolyl-(2S)-prolylglycine ethyl ester (DansylGlyProProGlyOEt)

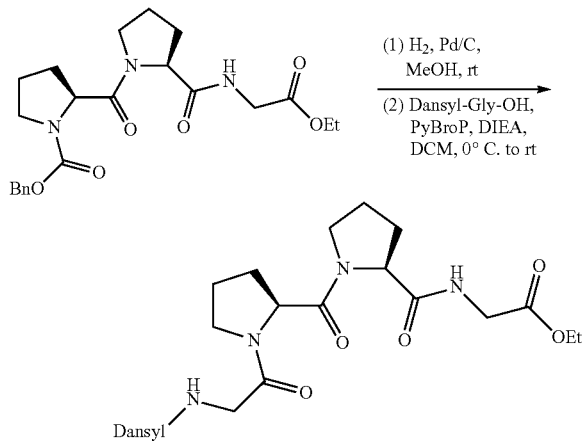

Procedure:

A suspension of CbzProProGly-OEt (755 mg, 1.8 mmoles) and Pd/C (76 mg) in MeOH (18 mL) was stirred under an atmosphere of $H_2$(g) for 3 h. The mixture was filtered through a pad of Celite®, and concentrated under reduced pressure to a pale yellow viscous oil (553 mg). The oil was dissolved in DCM (5.9 mL) and cooled to 0° C., after which DansylGlyOH (586 mg, 2.0 mmoles) and PyBroP® (973 mg, 2.3 mmoles) were added. The flask was capped with a septum and purged with $N_2$(g). DIEA (0.63 mL) was added via syringe and the reaction stirred at 0° C. for 5 min. The reaction was allowed to come to room temperature and stirred for an additional 6 h. The reaction was concentrated under reduced pressure, and the crude product was purified by chromatography on silica (2% MeOH in EtOAc) and HPLC (25-55% v/v acetonitrile in $H_2O$ with 0.1% v/v TFA) to afford the title compound (950 mg, 92%) as a yellow solid. This synthesis was previously reported.[38] $^1$H NMR (500 MHz, CDCl$_3$, mixture of 2 or more rotomers, integrations are approximate) δ8.59 (d, J=8.5 Hz, 1.0H), 8.37 (dd, J=8.5, 14.5 Hz, 1.1H), 8.25 (ddd, J=1.0, 7.0, 9.5 Hz, 1.0H), 8.20-8.14 (m, 0.7H), 7.65-7.55 (m, 2.1H), 7.26 (d, J=7.5 Hz, 1.0H), 7.18 (t, J=5.0 Hz, 0.7H), 5.76 (dd, J=3.5, 5.0 Hz, 0.7H), 5.67 (dd, J=3.5, 5.0 Hz, 0.6H), 4.58 (app dd, J=2.5, 8.0 Hz, 1.2H), 4.45 (t, J=6.5 Hz, 0.7H), 4.31 (d, J=8.5 Hz, 0.6H), 4.24-4.13 (m, 2.1H), 4.09-4.04 (m, 0.8H), 3.94-3.80 (m, 2.6H), 3.74-3.61 (m, 2.3H), 3.55-3.35 (m, 3.4H), 2.97-2.95 (m, 4.9H), 2.56 (app dd, J=6.0, 12.5 Hz, 0.7H), 2.36-2.31 (m, 0.8H), 2.24-1.80 (m, 11.9H), 1.33-1.26 (m, 2.9H); $^{13}$C NMR (100 MHz, CDCl$_3$, mixture of 2 or more rotomers) δ171.5, 171.4, 170.3, 169.7, 169.4, 165.8, 165.4, 151.3, 150.9, 134.3, 134.2, 130.5, 130.4, 129.8 (2 signals), 129.7 (2 signals), 129.5, 129.4, 128.5, 128.4, 123.4, 123.3, 119.8 (multiple signals), 119.5 (multiple signals), 115.6 (2 signals), 61.4, 61.3, 61.1, 59.7, 59.1, 58.2, 47.2, 47.1, 46.6, 46.2, 45.6, 45.5, 44.6, 44.5, 41.5, 41.3, 31.8, 28.5, 28.4, 27.0, 25.2, 24.9, 24.5, 22.1, 14.2 (2 signals); HRMS (ESI) m/z 610.2325 [calc'd for $C_{28}H_{37}N_5O_7SNa$ (M+Na)$^+$ 610.2306].

XVIII. Determination of Compound Purity

Compounds were analyzed by HPLC to assess their purity. Analyses were performed with a Waters HPLC system equipped with a Nucleodur® C18 Gravity reversed-phase column (4.6×250 mm, 5 µm particle size) from Macherey-Nagel. Compounds dissolved in 50 µL of $H_2O$ were injected onto the column and eluted at 1 mL/min over 20 min with a gradient of aqueous acetonitrile (5-95% v/v containing 0.1% v/v TFA). The maximal absorbance in the range of 210-400 nm was used as the detection wavelength.

REFERENCES (1) Shoulders, M. D.; Raines, R. T. *Annu. Rev. Biochem.* 2009, 78, 929.
(2) Rosenbloom, J.; Castro, S. V.; Jimenez, S. A. *Ann. Intern. Med.* 2010, 152, 159.
(3) Conklin, M. W.; Eickhoff, J. C.; Riching, K. M.; Pehlke, C. A.; Eliceiri, K. W.; Provenzano, P. P.; Friedl, A.; Keely, P. J. *Am. J. Pathol.* 2010, 178, 1221.
(4) Cox, T. R.; Bird, D.; Baker, A.-M.; Barker, H. E.; Ho, M. W.-Y.; Lang, G.; Erler, J. T. *Cancer Res.* 2014, 73, 1721.
(5) Eisinger-Mathason, T. S.; Zhang, M.; Qiu, Q.; Skuli, N.; Nakazawa, M. S.; Karakasheva, T.; Mucaj, V.; Shay, J. E. S.; Stangenberg, L.; Sadri, N.; Puré, E.; Yoon, S. S.; Kirsch, D. G.; Simon, M. C. *Cancer Discov.* 2013, 3, 1190.
(6) Gilkes, D. M.; Chaturvedi, P.; Bajpai, S.; Wong, C. C.; Wei, H.; Pitcairn, S.; Hubbi, M. E.; Wirtz, D.; Semenza, G. L. *Cancer Res.* 2013, 73, 3285.
(7) Provenzano, P. P.; Inman, D. R.; Eliceiri, K. W.; Knittel, J. G.; Yan, L.; Rueden, C. T.; White, J. G.; Keely, P. J. *BMC Med.* 2008, 6, 11.
(8) Myllyharju, J.; Kivirikko, K. I. *Trends Genet.* 2004, 20, 33.
(9) Gorres, K. L.; Raines, R. T. *Crit. Rev. Biochem. Mol.* 2010, 45, 106.
(10) Berg, R. A.; Prockop, D. *J. Biochem. Biophys. Res. Comm.* 1973, 52, 115.
(11) Myllyharju, J. *Ann. Med.* 2008, 40, 402.
(12) Hausinger, R. P. *Crit. Rev. Biochem. Mol.* 2004, 39, 21.
(13) Abraham, R. J.; McLauchlan, K. A. *Mol. Phys.* 1962, 5, 195.
(14) Anantharajan, J.; Koski, M. K.; Kursula, P.; Hieta, R.; Bergmann, U.; Myllyharju, J.; Wierenga, R. K. *Structure* 2013, 21, 2107.
(15) Hieta, R.; Kukkola, L.; Permi, P.; Pirilä, P.; Kivirikko, K. I.; Kilpeläinen, I.; Myllyharju, J. *J. Biol. Chem.* 2003, 278, 34966.
(16) Pekkala, M.; Hieta, R.; Bergmann, U.; Kivirikko, K. I.; Wierenga, R. K.; Myllyharju, J. *J. Biol. Chem.* 2004, 279, 52255.
(17) Rose, N. R.; Mcdonough, M. A.; King, O. N. F.; Kawamura, A.; Schofield, C. J. *Chem. Soc. Rev.* 2011, 40, 4364.
(18) Myllylä, R.; Tuderman, L.; Kivirikko, K. I. *Eur. J. Biochem.* 1977, 80, 349.
(19) Dowell, R. I.; Hadley, E. M. *J. Med. Chem.* 1992, 35, 800.
(20) Franklin, T. J.; Morris, W. P.; Edwards, P. N.; Large, M. S.; Stephenson, R. *Biochem. J.* 2001, 353, 333.
(21) Hales, N. J.; Beattie, J. F. *J. Med. Chem.* 1993, 36, 3853.

(22) Wang, J.; Buss, J. L.; Chen, G.; Ponka, P.; Pantopoulos, K. *FEBS Lett.* 2002, 529, 309.
(23) Baldwin, J. J.; Kasinger, P. A.; Novello, F. C.; Sprague, J. M.; Duggan, D. E. *J. Med. Chem.* 1975, 18, 895.
(24) Campeau, L.-C.; Rosseaux, S.; Fagnou, K. *J. Am. Chem. Soc.* 2005, 127, 18020.
(25) Campeau, L.-C.; Stuart, D. R.; Leclerc, J.-P.; Bertrand-Laperle, M.; Villemure, E.; Sun, H.-Y.; Lasserre, S.; Guimond, N.; Lecavallier, M.; Fagnou, K. *J. Am. Chem. Soc.* 2009, 131, 3291.
(26) Duric, S.; Tzschucke, C. C. *Org. Lett.* 2011, 13, 2310.
(27) Martin, T.; Verrier, C.; Hoarau, C.; Marsais, F. *Org Lett* 2008, 10, 2909.
(28) Strotman, N. A.; Chobanian, H. R.; Guo, Y.; He, J.; Wilson, J. E. *Org Lett* 2010, 12, 3578.
(29) Liu, W.; Yu, X.; Li, Y.; Kuang, C. *Chem. Commun.* 2014, 50, 9291.
(30) Baell, J.; Walters, M. A. *Nature* 2014, 513, 481.
(31) Sasaki, T.; Majamaa, K.; Uitto, J. *J. Biol. Chem.* 1987, 262, 9397.
(32) Tucker, H.; Thomas, D. F. *J. Med. Chem.* 1992, 35, 804.
(33) Cunliffe, C. J. et al. *J. Med. Chem.* 1992, 35, 2652-2658.
(34) Dowell, R. I; Hadley E. M. *Eur. J. Med. Chem.* 1993, 28, 513-516.
(35) Kersteen, E. A.; Higgin, J. J.; Raines, R. T. *Protein Exp. Purif.* 2004, 38, 279.
(36) Hewitson, K. S.; Schofield, C. J.; Ratcliffe, P. J. *Method Enzymol* 2007, 435, 25.
(37) Gibson, D. G. *Method Enzymol* 2011, 498, 349.
(38) Vasta, J. et al. "Selective Inhibition of Prolyl 4-Hydroxylases by Bipyridenedicarboxylates," *Biorg. Med. Chem.* 2015, 23(13), 3081.
(39) Hanauske-Abel, H. M., and Günzler, V. "A stereochemical concept for the catalytic mechanism of prolylhydroxylase: Applicability to classification and design of inhibitors," *J. Theor. Biol.* 1982, 94, 421-455.
(40) Costas, M., Mehn, M. P., Jensen, M. P., and Que, L. J. "Dioxygen activation at mononuclear nonheme iron active sites: Enzymes, models, and intermediates. *Chem. Rev.* 2004, 104, 939-986.
(41) Eisenstein, R. S., Tuazon, P. T., Schalinske, K. L., Anderson, S. A., and Traugh, J. A. (1993) Iron-responsive element-binding protein. Phosphorylation by protein kinase C. *J. Biol. Chem.* 268, 27363-27370.
(42) Goforth, J. B., Anderson, S. A., Nizzi, C. P., and Eisenstein, R. S. (2010) Multiple determinants within iron-responsive elements dictate iron regulatory protein binding and regulatory hierarchy. *RNA* 16, 154-169.
(43) Begtrup, M., Boyer, G., Cabildo, P., Cativiela, C., Claramunt, R. M., Elguero, J., García, J. I., Toiron, C., and Vedsø, P. (1993) $^{13}$C NMR of pyrazoles. *Magn. Reson. Chem.* 31, 107-168.
(44) Muckenthaler, M. U., Galy, B., and Hentze, M. W. "Systemic iron homeostasis and the iron-responsive element/ironregulatory protein (IRE/IRP) regulatory network," 2008, Annu. Rev. Nutr. 28, 197-213.
(45) Anderson, C. P., Shen, L., Eisenstein, R. S., and Leibold, E. A. "Mammalian iron metabolism and its control by iron regulatory proteins. Biochim. Biophys. 2012, Acta, Mol. Cell Res. 1823, 1468-1483.
(46) Testa, B., and Mayer, J. M. *Hydrolysis in Drug and Prodrug Metabolism: Chemistry, Biochemistry, and Enzymology,* 2003, Academic Press, New York, N.Y.
(47) Rautio, J. Prodrugs and Targeted Delivery: Towards Better ADME Properties, 2011, Wiley-VCH Verlag, Weinheim, Germany.
(48) Pearson, R. G., and Williams, F. V. "Rates of ionization of pseudo acids. V. Steric effects in the base-catalyzed ionization of nitroethane," 1953 *J. Am. Chem. Soc.* 75, 3073-3075.
(49) Albert, A., Goldacre, R., and Phillips, J. "The strength of heterocyclic base," 1948, *J. Chem. Soc.*, 2240-2249.
(50) Ford, P. C., DeForest, P. R., Gaunder, R., and Taube, H. (1968)"Synthesis and properties of pentaamminepyridineruthenium(II) and related pentaammineruthenium complexes of aromatic nitrogen heterocycles, 1968, *J. Am. Chem. Soc.* 90, 1187-1194.
(51) Walba, H., and Isensee, R. W. "Acidity constants of some arylimidazoles and their cations," 1961, *J. Org. Chem.* 26, 2789-2791.
(52) Catalan, J., and Elguero, J. "Basicity and acidity of azoles," 1987, Adv. Heterocycl. Chem. 41, 187-274.
(53) Zoltewicz, J. A., and Deady, L. W. (1978) Quaternization of heteroaromatic compounds: Quantitative aspects," 1978, Adv. Heterocycl. Chem. 22, 71-121.
(54) Brown, D. J., and Ghosh, P. B. "The spectra, ionization, and deuteriation of oxazoles and related compounds," 1969, *J. Chem. Soc.* B, 270-276.
(55) Krumholz, P. "Ferrous mono-α,α'-dipyridyl," 1949, *J. Am. Chem. Soc.* 71, 3654-3656.
(56) Job, P. "Formation and stability of inorganic complexes in solution," 1928, Annali di Chimica Applicata 9, 113-203.
(57) Huang, C. Y. "Determination of binding stoichiometry by the continuous variation method: The Job plot," 1982, Methods Enzymol. 87, 509-525.
(58) Vasta, J. D., Anderson, K. A., Deck, K. M., Nizzi, C. P. Eisenstein, R. S. and Raines, R. T. "Selective Inhibition of Collagen Prolyl 4-Hydroxylase in Human Cells," ACS Chemical Biol. 2016, 11, 193-199.

We claim:
1. A compound of formula:

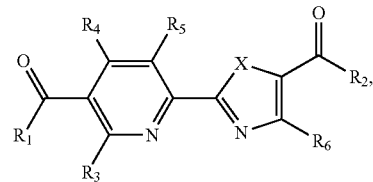

or salts thereof,
where:
X is S, O, NH, or NR,
where R is an alkyl group having 1-3 carbon atoms;
$R_1$ and $R_2$ independently are —$OR_7$, or —$NHSO_2R_8$,
where $R_7$ is selected from:
hydrogen, alkyl, alkoxyalkyl, —R'—CO—R", —R'—CO—O—R", —CO—R", —R'—O—CO—R", —R'—CO—NR", —CO—NR", —R'—O—CO—NR", and
$R_8$ is selected from hydrogen, alkyl, aryl or arylalkyl;
$R_3$, $R_4$ and $R_6$ independently are hydrogen, alkyl, alkoxy, alkenyl, alkenoxy, haloalkyl, haloalkenyl, halogen, hydroxyl, hydroxyalkyl, hydroxyalkenyl, aryl, aryloxy, arylalkyl or arylalkyoxy;
$R_5$ is hydrogen, an alkyl having 1-3 carbon atoms or an alkoxy having 1-3 carbon atoms;
—R'— is a divalent straight chain or branched alkylene, and
—R" is an alkyl, aryl or arylalkyl.

2. The compound of claim 1, where X is S.
3. The compound of claim 1, where X is O.
4. The compound of claim 1, where X is NH.
5. The compound of claim 1, where X is $NCH_3$.
6. The compound of claim 1, wherein $R_3$, $R_4$ and $R_6$ are all hydrogens.
7. The compound of claim 1, wherein $R_3$, $R_4$ and $R_6$ are selected from hydrogen, alkyl, alkoxy or halogen.
8. The compound of claim 1, wherein $R_3$, $R_4$, and $R_6$ are hydrogen or alkyl groups having 1-3 carbon atoms.
9. The compound of claim 1, wherein $R_3$, $R_4$ and $R_6$ independently are hydrogen, alkyl, alkoxy, halogen, hydroxyl, phenyl or benzyl.
10. The compound of claim 1, wherein $R_1$ and $R_2$ are independently —$OR_7$ groups where $R_7$ is an alkyl group having 1-8 carbon atoms.
11. The compound of claim 1, wherein $R_1$ and $R_2$ are —$OR_7$ groups where $R_7$ is a methyl or an ethyl group.
12. The compound of claim 1, wherein $R_1$ and $R_2$ are —$OR_7$ groups where $R_7$ is an alkoxyalkyl group.
13. The compound of claim 1, wherein at least one of $R_1$ or $R_2$ is —$NHSO_2R_8$.
14. A compound of formula:

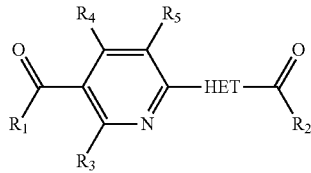

or salts thereof,
where:
$R_1$ and $R_2$ independently are —$OR_7$, or —$NHSO_2R_8$, where $R_7$ is selected from:
hydrogen, alkyl, alkoxyalkyl, —R'—CO—R", —R'—CO—O—R", —CO—R", —R'—O—CO—R", —R'—CO—NR", —CO—NR", —R'—O—CO—NR", and
$R_8$ is selected from hydrogen, alkyl, aryl or arylalkyl;
$R_3$, $R_4$ and $R_6$ independently are hydrogen, alkyl, alkoxy, alkenyl, alkenoxy, haloalkyl, haloalkenyl, halogen, hydroxyl, hydroxyalkyl, hydroxyalkenyl, aryl, aryloxy, arylalkyl or arylalkyoxy;
$R_5$ is hydrogen, an alkyl having 1-3 carbon atoms or an alkoxy having 1-3 carbon atoms;
—R'— is a divalent straight chain or branched alkylene;
—R" is an alkyl, aryl or arylalkyl; and
HET is selected from:

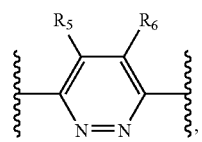
A1

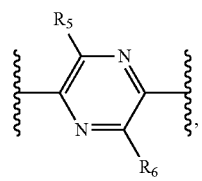
A2

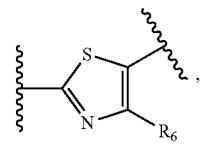
B1

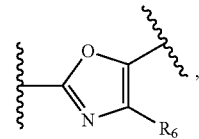
B2

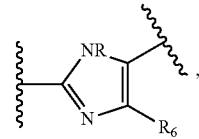
B3

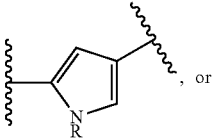
C1

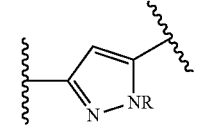
C2 where R is hydrogen or an alkyl group.

15. The compound of claim 14, wherein Het is

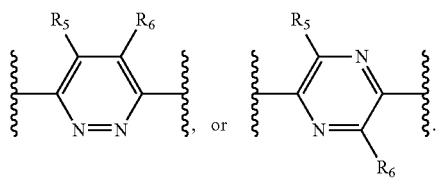

16. A pharmaceutical composition comprising a therapeutically effective amount of one or more compounds or salts of claim 1 and a pharmaceutically acceptable carrier.

17. The compound of claim 14, wherein R is hydrogen, $R_3$-$R_6$ are each hydrogen, $R_1$ and $R_2$ are —$OR_7$ and $R_7$ is an alkyl group having 1-8 carbon atoms.

18. The compound of claim 17, wherein Het is

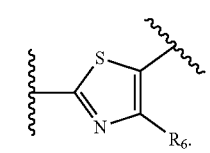

19. The compound of claim 18, wherein $R_7$ is ethyl.
20. The compound of claim 17, wherein Het is
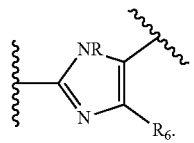
21. A pharmaceutical composition comprising a therapeutically effective amount of one or more compounds or salts of claim 17 and a pharmaceutically acceptable carrier.
* * * * *